(12) United States Patent
Ueno et al.

(10) Patent No.: US 6,964,975 B2
(45) Date of Patent: Nov. 15, 2005

(54) ISOXAZOLE AND THIAZOLE COMPOUNDS AND USE THEREOF AS MEDICINE

(75) Inventors: Akihiro Ueno, Gunma (JP); Rika Nagao, Gunma (JP); Tomoko Watanabe, Gunma (JP); Hideo Ohta, Tokyo (JP); Mikio Yagi, Gunma (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/204,173

(22) PCT Filed: Feb. 19, 2001

(86) PCT No.: PCT/JP01/01173

§ 371 (c)(1),
(2), (4) Date: Aug. 19, 2002

(87) PCT Pub. No.: WO01/60819

PCT Pub. Date: Aug. 23, 2001

(65) Prior Publication Data

US 2003/0114505 A1 Jun. 19, 2003

(30) Foreign Application Priority Data

Feb. 18, 2000 (JP) .......................... 2000-041922

(51) Int. Cl.[7] ................. A61K 31/42; A61K 31/422; C07D 261/14; C07D 413/04
(52) U.S. Cl. ................. 514/372; 514/380; 514/340; 514/236.8; 546/272.1; 544/137; 548/214; 548/245
(58) Field of Search ................. 548/214, 245; 514/380, 372

(56) References Cited

U.S. PATENT DOCUMENTS 5,861,359 A * 1/1999 Theodoridis ................ 504/282
6,403,791 B1 * 6/2002 Dyke et al. ................. 544/140

FOREIGN PATENT DOCUMENTS

WO  WO 95/13075 A    5/1995
WO  WO 98/27213 A    6/1998
WO  WO 01/34573    *  5/2001

OTHER PUBLICATIONS

Drummond et al., J. Med. Chem. (1989), 32(9), pp. 2116–2128.*
CA Registry No. 261714–80–1, entry date in Registry file is Apr. 12, 2000.*
CA Registry No. 261714–57–2, entry date in Registry file is Apr. 12, 2000.*
CA Registry No. 261622–75–7, entry date in Registry file is Apr. 11, 2000.*
CA Registry No. 257284–80–3, entry date in Registry file is Feb. 29, 2000.*
Reiter, Journal of Organic Chemistry (1987), 52(13), pp. 2714–2726.*
Pharmazie, 1994, vol. 49, No. 10, pp. 727–729.
Database Crossfire Beilstein *Online! Beilstein Institut zur Forderung der Chemischen Wissenschaften, Frankfurt am Main, DE; Database accession No. 997021 XP002232339, 3,5–dimethyl–4 benzyloxycarbonylamino–isothiazole *abstract* & Indian J. Chem., vol. 7, 1969, pp. 103–105.
Database Crossfire Beilstein *Online! Beilstein institut zur Forderung der Chemischen Wissenschaften, Frankfurt am Main, DE; Database accession No. 920183 XP002232340 (5–methyl–3–phenyl–isoxazole–4–yl)– carbamic acid ethyl ester *abstact* & Pharm Chem. J., vol.7, 1968, pp. 388–389.

* cited by examiner

Primary Examiner—Laura L. Stockton
(74) Attorney, Agent, or Firm—Foley & Lardner LLP

(57) ABSTRACT

The present invention relates to novel isoxazole and thiazole compounds having an excellent lysophosphatidic acid (LPA) receptor antagonistic activity represented by general formula [1] or salts thereof:

[1]

wherein R1 and R2 represents an optionally substituted alkyl group or the like; R3 represents a hydrogen atom or the like; R4 represent a group selected from the group consisting of (I) optionally substituted phenyl, aryl, or heterocycle, (II) substituted or nonsubstituted alkyl, and (III) substituted or nonsubstituted alkenyl, alternatively, R3 and R4 may form a ring structure together with a carbon atom to which they bind; and X represents an oxygen atom or a sulfur atom, provided that, when R3 is a hydrogen atom, R4 represents a group other than methyl, and the use thereof as a medicine.

18 Claims, 10 Drawing Sheets

Fig.1C

| | | |
|---|---|---|
| Compound 119 | | |
| Compound 120 | | |
| Compound 121 | | |
| Compound 122 | | |
| Compound 123 | | |
| Compound 124 | | |
| Compound 125 | | |

| | |
|---|---|
| Compound 126 | |
| Compound 127 | |
| Compound 128 | |
| Compound 129 | |
| Compound 130 | |
| Compound 131 | |
| Compound 132 | |
| Compound 133 | |

Fig.1E

| | |
|---|---|
| Compound 134 | (structure) |
| Compound 135 | (structure) |
| Compound 136 | (structure) |
| Compound 137 | (structure) |
| Compound 138 | (structure) |
| Compound 139 | (structure) |
| Compound 140 | (structure) |
| Compound 141 | (structure) |

| Compound 142 | |
| Compound 143 | |
| Compound 144 | |
| Compound 145 | |
| Compound 146 | |
| Compound 147 | |
| Compound 148 | |
| Compound 149 | |

| Compound 150 |
| Compound 151 |
| Compound 152 |
| Compound 153 |
| Compound 154 |
| Compound 155 |
| Compound 156 |

ISOXAZOLE AND THIAZOLE COMPOUNDS AND USE THEREOF AS MEDICINE

TECHNICAL FIELD

The present invention relates to novel isoxazole and thiazole compounds (hereinafter referred to as an "azole compound") or salt thereof. The azole compound of the present invention is useful as a lysophosphatidic acid (LPA) receptor antagonist and as a therapeutic or preventive agent for cell proliferative diseases, inflammatory diseases, kidney diseases, and cerebral or peripheral nerve disorders.

BACKGROUND ART

Lysophosphatidic acid (LPA) is a bioactive lysophospholipid which exists in organisms in very small amounts and is produced and released when various cells including platelets are stimulated by bioactive substances such as cytokines (J. Biol. Chem. 270: 12949 (1995); J. Biol. Chem. 267: 10988 (1992)). Therefore, it is believed that LPA concentration is elevated at sites of inflammation, hemorrhage or the like. Actually, it has been clarified that 2 to 20 µM of LPA is contained in blood serum and, in the case of a model of intracerebral hemorrhage, the LPA concentration in cerebral spinal fluid has been reported to be elevated to about 3 µM (J. Neurochem. 67: 2300 (1996)). Recently, elevated LPA concentration in human arteriosclerotic lesions was also reported (Proc. Natl. Acad. Sci. USA 96: 6931 (1999)). Further, elevated LPA concentration has been reported in the ascites of patients with peritoneal disseminated ovarian carcinoma and in the blood of patients with multiple myeloma (Lipids 34: 17 (1999); Gynecol. Oncol. 98: 71 (364)). While a site of action of LPA had not been heretofore clarified, the receptor specific for LPA was recently identified (Biochem. Biophys. Res. Commun. 231: 619 (1997)) and various biological activities of LPA, for example, cell proliferation, migration/invasion and platelet aggregation, have been elucidated as being effected through a cell membrane receptor. Regarding cell proliferation promoting activity, the effect of LPA has been reported in, for example, smooth muscle cells (Am. J. Physiol. 267: C204 (1994); Atherosclerosis 130: 121 (1997)), renal mesangial cells (Clinical Sci. 96: 431 (1999)), stellate cells of liver (Biochem. Biophys. Res. Commun. 191: 675 (1998)), fibroblasts (Naunyn-Schmiedeberg's Arch Pharmacol 355: 1 (1997)), and various carcinoma cells and abnormal proliferation of these cells caused by LPA is suggested to be associated with disease progression. Futhermore, the acceleration of migration activity in monocytes (J. Biol. Chem. 270: 25549 (1995)), activation of NF-κB in fibroblast (J. Biol. Chem. 274: 3828 (1999)) enhancement of fibronectin-binding to the cell surface (J. Biol. Chem. 274: 27257 (1999); J. Biol. Chem. 268: 23850 (1993)), promoting invasion of carcinoma cells (Biochem. Biophys. Res. Commun. 193: 497 (1993)) and the like have been observed. Thus, the association with various inflammatory diseases and the invasion and metastasis of carcinomas are suggested. Further, LPA has been reported as a causative agent in neurite retraction and cell death in neural cells, in particular, the possibility of LPA to be associated with neurodestruction after hemorrhage (J. Neurochem. 61: 340 (1993); J. Neurochem. 70: 66 (1998)).

The search for an agent to inhibit LPA-induced cell activation is considered the key elements leading to the prevention and treatment of restenosis after percutaneous transluminal coronary angioplasty (PTCA), arteriosclerosis, artery obstructions, malignant and benign proliferative diseases, various inflammatory diseases, kidney diseases, proliferation of tumor cells, invasion and metastasis of carcinomas, cerebral or periphery nerve disorders and the like. There has been heretofore no report on a low molecular weight compound having such inhibitory activities.

The object of the present invention is to provide a novel azole compound having an excellent LPA receptor antagonistic action and the application thereof to medicines.

SUMMARY OF THE INVENTION

The present inventors have conducted concentrated studies in order to develop a novel agent for inhibiting diseases caused by LPA and, as a result, found that a novel azole compound would inhibit actions effected through an LPA receptor. This has led to the completion of the present invention.

Specifically, the present invention comprises the following.

According to the first aspect, the present invention provides an azole compound represented by general formula [1] or salt thereof:

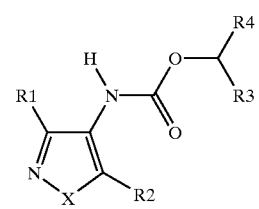

[1]

wherein

R1 represents an optionally substituted alkyl, aryl, heterocycle, alkyloxy, aryloxy, alkylthio, arylthio, or a halogen atom;

R2 represents an optionally substituted alkyl, aryl, heterocycle, alkyloxy, aryloxy, or a halogen atom;

R3 represents a hydrogen atom, lower alkyl, or alkyl halide;

R4 represents a group selected from the group consisting of (I) optionally substituted phenyl, aryl, or heterocycle, (II) substituted or nonsubstituted alkyl, and (III) substituted or nonsubstituted alkenyl, alternativily, R3 and R4 may form a five- to ten-membered cyclic structure together with a carbon atom to which they bind; and X represents an oxygen atom or a sulfur atom, provided that, when R3 is a hydrogen atom, R4 represents a group other than methyl.

The present invention provides the azole compound represented by formula [1] or salt thereof, wherein R1 is a halogen atom or lower alkyl optionally substituted by one or more substituents selected from the group consisting of (I) alkyloxy, (II) alkylthio, (III) alkylamino, (IV) cyano, (V) nitro, (VI) cyclic amino, and (VII) a halogen atom; and R2 is aryl or aromatic heterocycle optionally substituted by one or more substituents selected from the group consisting of:

(I) a halogen atom;

(II) lower alkyl optionally substituted by one or more substituents selected from the group consisting of (1) hydroxy, (2) thiol, (3) amino, (4) alkyloxy, (5) alkylthio, (6) alkylsulfinyl, (7) alkylsulfonyl, (8) monoalkylamino or dialkylamino, (9) acyloxy, (10) acylthio, (11) acylamino, (12) aryloxy, (13) arylthio, (14) arylsulfinyl, (15)

arylsulfonyl, (16) arylamino, (17) alkylsulfonylamino or arylsulfonylamino, (18) alkylureide or arylureide, (19) alkyloxycarbonylamino or aryloxycarbonylamino, (20) alkylaminocarbonyloxy or arylaminocarbonyloxy, (21) carboxyl, (22) nitro, (23) heterocycle, (24) cyano, (25) cyclic amino, and (26) a halogen atom;

(III) optionally halogenated alkyloxy; (IV) optionally halogenated alkylthio; (V) cycloalkyl; (VI) aryl; (VII) aryloxy; (VIII) acylamino; (IX) acyloxy; (X) hydroxy; (XI) nitro; (XII) cyano; (XIII) amino; (XIV) monoalkylamino or dialkylamino; (XV) arylamino; (XVI) alkylsulfonylamino or arylsulfonylamino; (XVII) alkylureide or arylureide; (XVI) alkyloxycarbonylamino or aryloxycarbonylamino; (XIX) alkylaminocarbonyloxy or arylaminocarbonyloxy; (XX) alkyloxycarbonyl or aryloxycarbonyl; (XXI) acyl; (XXII) carboxyl; (XXII) carbamoyl; (XXIV) monoalkylcarbamoyl or dialkylcarbamoyl; (XXV) cyclic amino; and (XXVI) alkylsulfonyl or arylsulfonyl.

The present invention provides the azole compound represented by formula [1] or salt thereof, wherein R1 is aryl or aromatic heterocycle optionally substituted by one or more substituents selected from the group consisting of:

(I) a halogen atom;

(II) lower alkyl optionally substituted by one or more substituents selected from the group consisting of (1) hydroxy, (2) thiol, (3) amino, (4) alkyloxy, (5) alkylthio, (6) alkylsulfinyl, (7) alkylsulfonyl, (8) monoalkylamino or dialkylamino, (9) acyloxy, (10) acylthio, (11) acylamino, (12) aryloxy, (13) arylthio, (14) arylsulfinyl, (15) arylsulfonyl, (16) arylamino, (17) alkylsulfonylamino or arylsulfonylamino, (18) alkylurcide or arylureide, (19) alkyloxycarbonylamino or aryloxycarbonylamino, (20) alkylaminocarbonyloxy or arylaminocarbonyloxy, (21) carboxyl, (22) nitro, (23) heterocycle, (24) cyano, (25) cyclic amino, and (26) a halogen atom;

(III) optionally halogenated alkyloxy; (IV) optionally halogenated alkylthio; (V) cycloalkyl; (VI) aryl; (VII) aryloxy; (VIII) acylamino; (IX) acyloxy; (X) hydroxy; (XI) nitro (XII) cyano; (XIII) amino; (XIV) monoalkylamino or dialkylamino; (XV) arylamino; (XVI) alkylsulfonylamino or arylsulfonylamino; (XVII) alkylureide or arylureide; (XVII) alkyloxycarbonylamino or aryloxycarbonylamino; (XIX) alkylaminocarbonyloxy or arylaminocarbonyloxy; (XX) alkyloxycarbonyl or aryloxycarbonyl; (XXI) acyl; (XXII) carboxyl; (XXIII) carbamoyl; (XXIV) monoalkylcarbamoyl or dialkylcarbamoyl; (XXV) cyclic amino; and (XXVI) alkylsulfonyl or arylsulfonyl; and R2 is a halogen atom or lower alkyl optionally substituted by one or more substituents selected from the group consisting of (I) alkyloxy, (II) alkylthio, (III) alkylamino, (IV) cyano, (V) nitro, (VI) cyclic amino, and (VII) a halogen atom.

In one embodiment, the present invention provides the azole compound represented by general formula [2] or salt thereof:

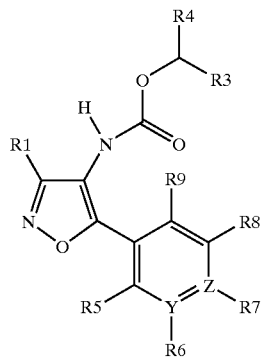

[2]

wherein
R1, R3, and R4 are as defined above;
Y and Z are each independently a carbon atom or a nitrogen atom; and
R5, R6, R7, R8, and R9 are each independently selected from
(I) a hydrogen atom;
(II) a halogen atom;
(III) lower alkyl optionally substituted by one or more substituents selected from the group consisting of (1) hydroxy, (2) amino, (3) alkyloxy, (4) alkylthio, (5) alkylsulfinyl, (6) alkylsulfonyl, (7) monoalkylamino or dialkylamino, (8) acyloxy, (9) acylamino, (10) aryloxy, (11) arylthio, (12) arylsulfinyl, (13) arylsulfonyl, (14) arylamino, (15) alkylsulfonylamino or arylsulfonylamino, (16) alkylureide or arylureide, (17) alkyloxycarbonylamino or aryloxycarbonylamino, (18) alkylaminocarbonyloxy or arylaminocarbonyloxy, (19) cyano, (20) cyclic amino, and (21) a halogen atom;
(IV) optionally halogenated alkyloxy, (V) cycloalkyl, (VI) aryl, (VII) aryloxy, (VIII) acylamino, (IX) acyloxy, (X) hydroxy, (XI) nitro, (XII) cyano, (XIII) amino, (XIV) monoalkylamino or dialkylamino, (XV) arylamino, (XVI) alkylsulfonylamino or arylsulfonylamino, (XVII) alkylureide or arylureide, (XVIII) alkyloxycarbonylamino or aryloxycarbonylamino, (XIX) alkylaminocarbonyloxy or arylaminocarbonyloxy, (XX) alkyloxycarbonyl or aryloxycarbonyl, (XXI) acyl, (XXII) carboxyl, (XXIII) carbamoyl, (XXIV) monoalkylcarbamoyl or dialkylcarbamoyl, (XXV) cyclic amino, and (XXVI) alkylsulfonyl or arylsulfonyl,
provided that, when Y is a nitrogen atom, R6 is absent, and when Z is a nitrogen atom, R7 is absent.

The present invention provides the azole compound represented by formula [2] or salt thereof, wherein
R1 is methyl or ethyl;
R3 is a hydrogen atom, methyl, or trifluoromethyl;
R4 is phenyl optionally substituted by one or more substituents selected from the group consisting of (I) a halogen atom, (II) optionally halogenated lower alkyl, (III) optionally halogenated alkyloxy, (IV) optionally halogenated alkylthio, (V) cycloalkyl, (VI) aryl, (VII) aryloxy, (VIII) acylamino, (VIX) acyloxy, (X) hydroxy, (XI) nitro, (XII) cyano, (XIII) amino, (XIV) monoalkylamino or dialkylamino, (XV) arylamino, (XVI) alkylsulfonylamino or arylsulfonylamino, (XVII) alkylureide or arylureide, (XVIII) alkyloxycarbonylamino or aryloxycarbonylamino, (XIX) alkylaminocarbonyloxy or arylaminocarbonyloxy, (XX) alkyloxycarbonyl or aryloxycarbonyl, (XXI) acyl, (XXII) carboxyl, (XXIII) carbamoyl, (XXIV) monoalkylcarbamoyl or dialkylcarbamoyl, (XXV) cyclic amino, and (XXVI) alkylsulfonyl or arylsulfonyl;

Y and Z are a carbon atom; and at least one of R6 and R7 is a halogen atom, chloromethyl, hydroxymethyl, cyano, trifluoromethoxy, a group represented by formula [3]:

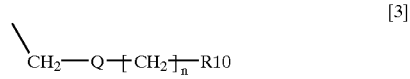

wherein n is 0 to 5;

Q is an oxygen atom, a sulfur atom, sulfinyl, or sulfonyl; and

R10 is selected from the group consisting of a hydrogen atom, a halogen atom, alkyl, alkyloxy, alkylthio, monoalkylamino or dialkylamino, aryloxy, arylthio, cyano, nitro, carboxyl, alkyloxycarbonyl or aryloxycarbonyl, carbamoyl, monoalkylcarbamoyl or dialkylcarbamoyl, acyl, aryl, cyclic amino, and heterocycle, or a group represented by formula [4]:

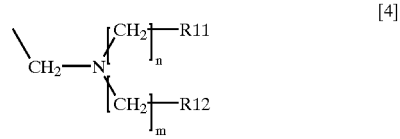

wherein n and m are each 0 to 5; and

R11 and R12 are each independently selected from the group consisting of a hydrogen atom, a halogen atom, alkyl, alkyloxy, alkylthio, monoalkylamino or dialkylamino, aryloxy, arylthio, hydroxy, cyano, nitro, carboxyl, alkyloxycarbonyl or aryloxycarbonyl, carbamoyl, monoalkylcarbamoyl or dialkylcarbamoyl, acyl, aryl, cyclic amino, and heterocycle; or R11 and R12 may together form a five- to nine-membered heterocycle containing, in addition to a nitrogen atom, 1 to 3 oxygen atoms or sulfur atoms.

In another embodiment, the present invention provides the azole compound represented by formula [5] or salt thereof:

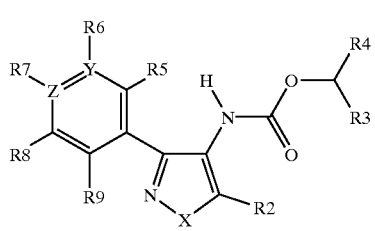

wherein

R2, R3, and R4 are as defined above;

Y and Z are each independently a carbon atom or a nitrogen atom; and

R5, R6, R7, R8, and R9 are each independently selected from the group consisting of:

(I) a hydrogen atom;

(II) a halogen atom;

(III) lower alkyl optionally substituted by one or more substituents selected from the group consisting of (1) hydroxy, (2) amino, (3) alkyloxy, (4) alkylthio, (5) alkylsulfinyl, (6) alkylsulfonyl, (7) monoalkylamino or dialkylamino, (8) acyloxy, (9) acylamino, (10) aryloxy, (11) arylthio, (12) arylsulfinyl, (13) arylsulfonyl, (14) arylamino, (15) alkylsulfonylamino or arylsulfonylamino, (16) alkylureide or arylureide, (17) alkyloxycarbonylamino or aryloxycarbonylamino, (18) alkylaminocarbonyloxy or arylaminocarbonyloxy, (19) cyano, (20) cyclic amino, and (21) a halogen atom;

(IV) optionally halogenated alkyloxy, (V) cycloalkyl, (VI) aryl, (VII) aryloxy, (VIII) acylamino, (IX) acyloxy, (X) hydroxy, (XI) nitro, (XII) cyano, (XIII) amino, (XIV) monoalkylamino or dialkylamino, (XV) arylamino, (XVI) alkylsulfonylamino or arylsulfonylamino, (XVII) alkylureide or arylureide, (XVIII) alkyloxycarbonylamino or aryloxycarbonylamino, (XIX) alkylaminocarbonyloxy or arylaminocarbonyloxy, (XX) alkyloxycarbonyl or aryloxycarbonyl, (XXI) acyl, (XXII) carboxyl, (XXIII) carbamoyl, (XXIV) monoalkylcarbamoyl or dialkylcarbamoyl, (XXV) cyclic amino, and (XXVI) alkylsulfonyl or arylsulfonyl, provided that, when Y is a nitrogen atom, R6 is absent, and when Z is a nitrogen atom, R7 is absent.

The present invention provides the azole compound represented by formula [5] or salt thereof, wherein R2 is methyl or ethyl;

R3 is a hydrogen atom, methyl, or trifluoromethyl;

R4 is phenyl optionally substituted by one or more substituents selected from the group consisting of (I) a halogen atom, (II) optionally halogenated lower alkyl, (III) optionally halogenated alkyloxy, (IV) optionally halogenated alkylthio, (V) cycloalkyl, (VI) aryl, (VII) aryloxy, (VIII) acylamino, (VIX) acyloxy, (X) hydroxy, (XI) nitro, (XII) cyano, (XIII) amino, (XIV) monoalkylamino or dialkylamino, (XV) arylamino, (XVI) alkylsulfonylamino or arylsulfonylamino, (XVII) alkylureide or arylureide, (XVIII) alkyloxycarbonylamino or aryloxycarbonylarmino, (XIX) alkylaminocarbonyloxy or arylaminocarbonyloxy, (XX) alkyloxycarbonyl or aryloxycarbonyl, (XXI) acyl, (XXII) carboxyl, (XXIII) carbamoyl, (XXIV) monoalkylcarbamoyl or dialkylcarbamoyl, (XXV) cyclic amino, and (XXVI) alkylsulfonyl or arylsulfonyl, Y and Z are each independently a carbon atom; and at least one of R6 and R7 is a halogen atom, chloromethyl, hydroxymethyl, cyano, trifluoromethoxy, a group represented by formula [3]:

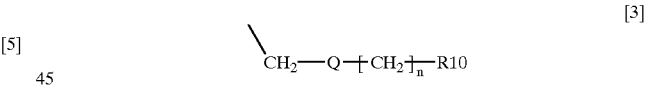

wherein n is 0 to 5;

Q is an oxygen atom, a sulfur atom, sulfinyl, or sulfonyl; and

R10 is selected from the group consisting of a hydrogen atom, a halogen atom, alkyl, alkyloxy, alkylthio, monoalkylamino or dialkylamino, aryloxy, arylthio, cyano, nitro, carboxyl, alkyloxycarbonyl or aryloxycarbonyl, carbamoyl, monoalkylcarbamoyl or dialkylcarbamoyl, acyl, aryl, cyclic amino, and heterocycle, or a group represented by formula [4]:

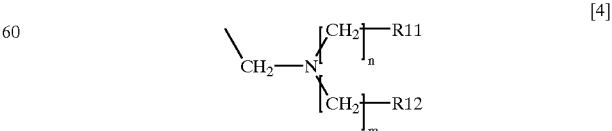

wherein n and m are each 0 to 5; and

R11 and R12 are each independently selected from the group consisting of a hydrogen atom, a halogen atom, alkyl, alkyloxy, alkylthio, monoalkylamino or dialkylamino, aryloxy, arylthio, hydroxy, cyano, nitro, carboxyl, alkyloxycarbonyl or aryloxycarbonyl, carbamoyl, monoalkylcarbamoyl or dialkylcarbamoyl, acyl, aryl, cyclic amino, and heterocycle; or R11 and R12 may together form a five- to nine-membered heterocycle containing, in addition to a nitrogen atom, 1 to 3 oxygen atoms or sulfur atoms.

The present invention provides the azole compound represented by formula [2] or [5] or salt thereof, wherein R4 is phenyl optionally substituted by one or more substituents selected from the group consisting of (I) a halogen atom, (II) optionally halogenated lower alkyl, (III) optionally halogenated alkyloxy, (IV) optionally halogenated alkylthio, (VIII) acylamino, (X) hydroxy, (XI) nitro, (XII) cyano, (XIII) amino, (XIV) monoalkylamino or dialkylamino, (XX) alkyloxycarbonyl or aryloxycarbonyl, (XXI) acyl, (XXII) carboxyl, and (XXV) cyclic amino.

The present invention provides the azole compound represented by formula [2] or [5] or salt thereof, wherein R4 is a nonsubstituted phenyl, 2-chlorophenyl, 2-bromophenyl, or 2-fluorophenyl.

According to the second aspect, the present invention provides a lysophosphatidic acid (LPA) receptor antagonist comprising, as an active ingredient, the above novel azole compound or salt thereof.

According to the third aspect, the present invention provides a therapeutic or preventive agent for cell proliferative diseases comprising, as an active ingredient, the above novel azole compound or salt thereof.

According to the fourth aspect, the present invention provides a therapeutic or preventive agent for inflammatory diseases comprising, as an active ingredient, the above novel azole compound or salt thereof.

According to the fifth aspect, the present invention provides a therapeutic or preventive agent for kidney diseases comprising, as an active ingredient, the above novel azole compound or salt thereof.

According to the sixth aspect, the present invention provides a therapeutic or preventive agent for cerebral or peripheral nerve disorders comprising, as an active ingredient, the above novel azole compound or salt thereof.

According to the seventh aspect, the present invention provides a therapeutic or preventive agent for artery obstructions comprising, as an active ingredient, the above novel azole compound or salt thereof.

According to the eighth aspect, the present invention provides an antitumor agent comprising, as an active ingredient, the above novel azole compound or salt thereof.

BRIEF DESCRIPTION OF DRAWINGS

FIG. 1A to FIG. 1I show structures of Compound 103 to Compound 169 (in Examples 103 to 169 below).

FIG. 2A shows the inhibition of the proliferation of human brain tumor cells and FIG. 2B shows the inhibition of the proliferation of human ovarian carcinoma cells.

DETAILED DESCRIPTION OF THE INVENTION

Figure 1A:
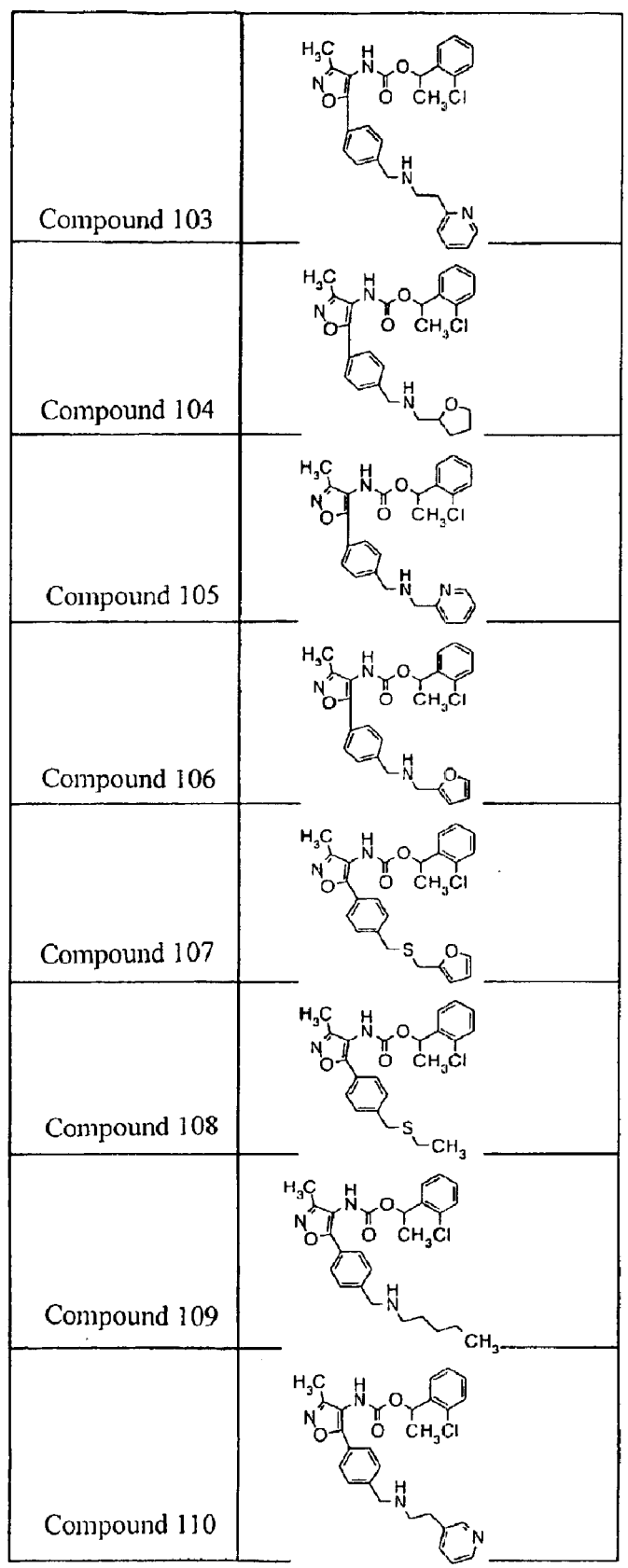
Figure 1B:
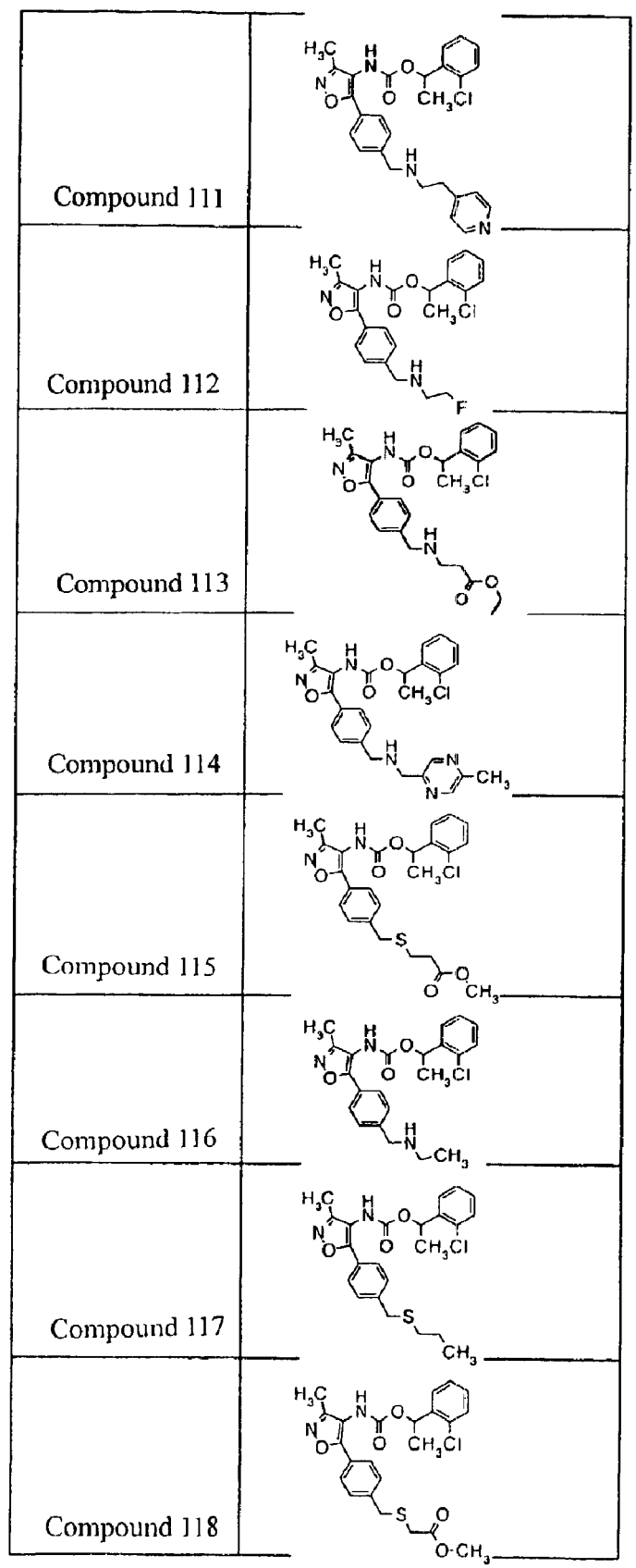
Figure 1D:
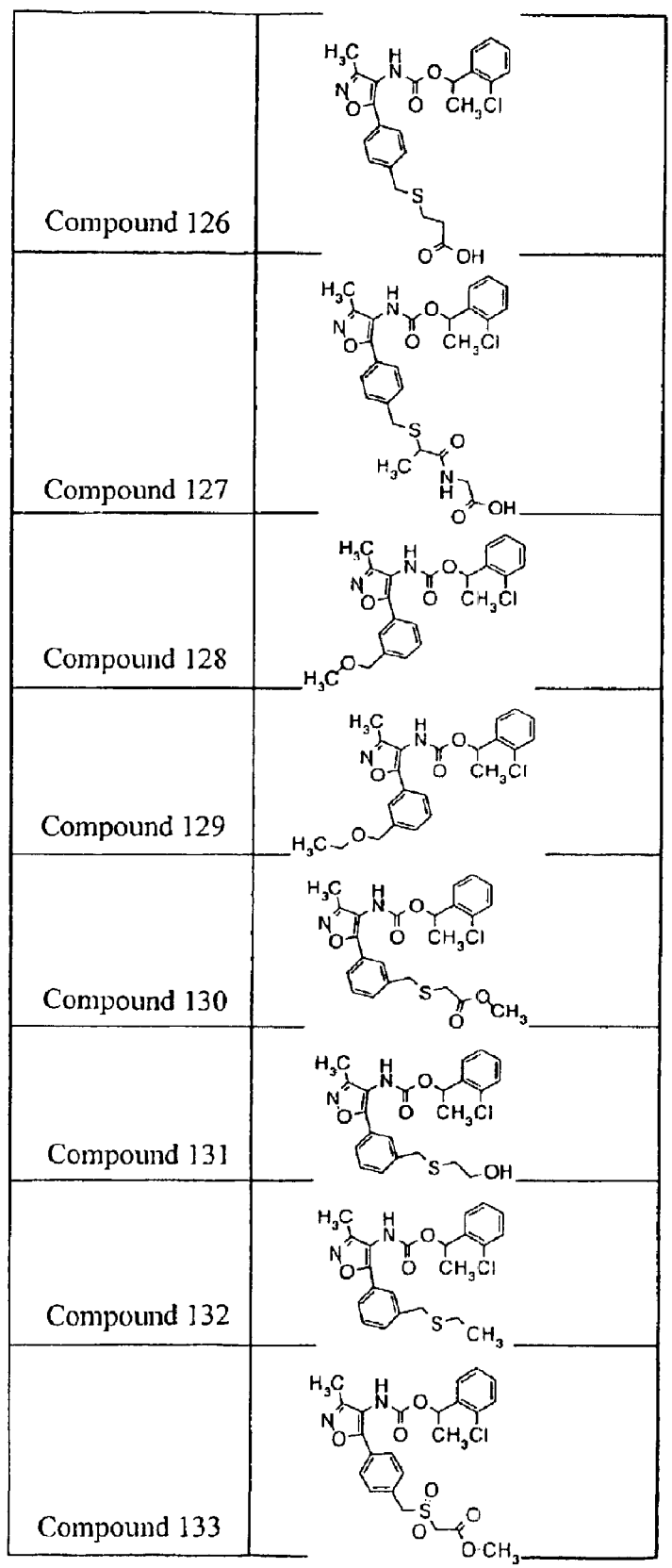
Figure 1F:
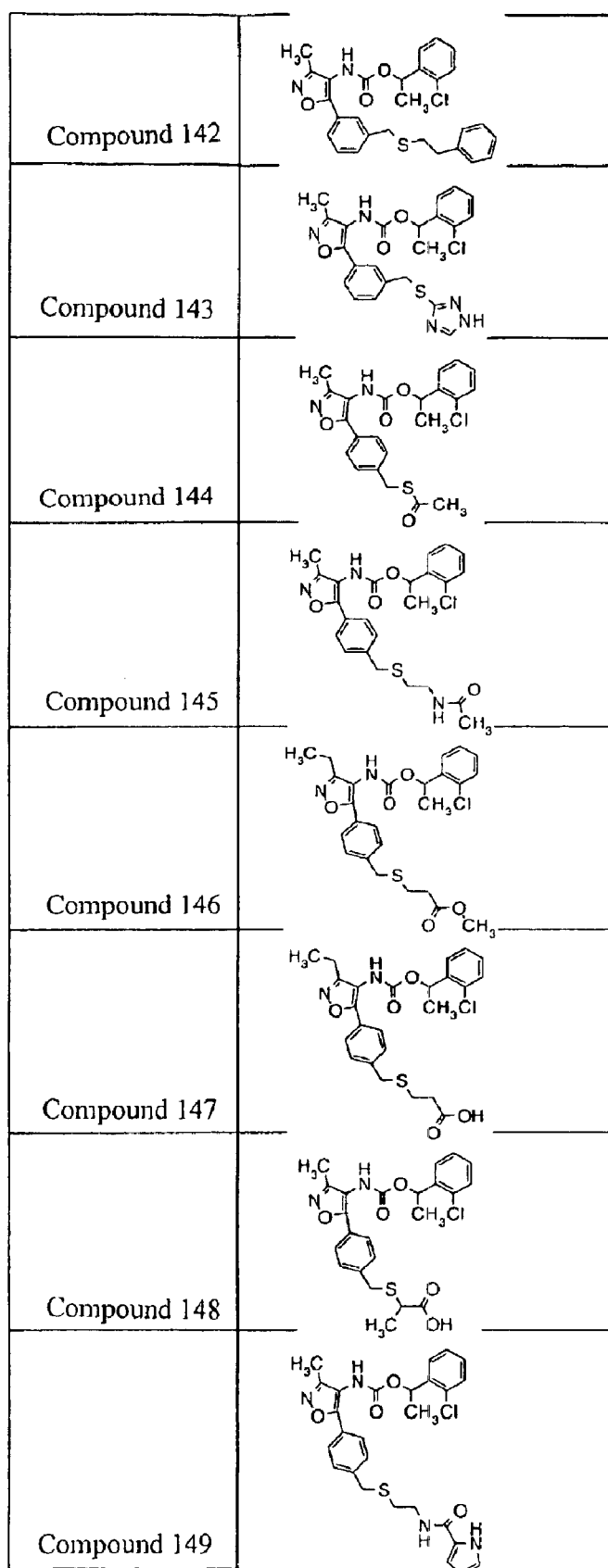
Figure 1G:
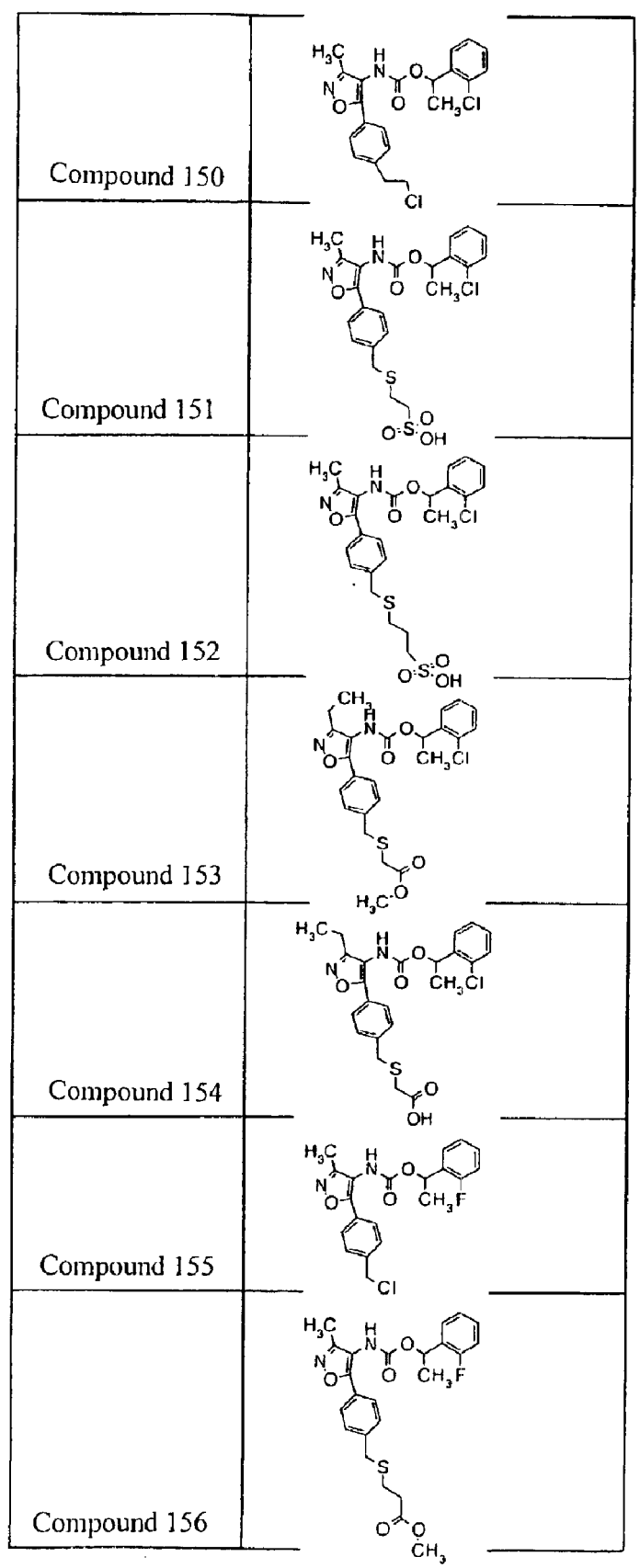
Figure 1H:
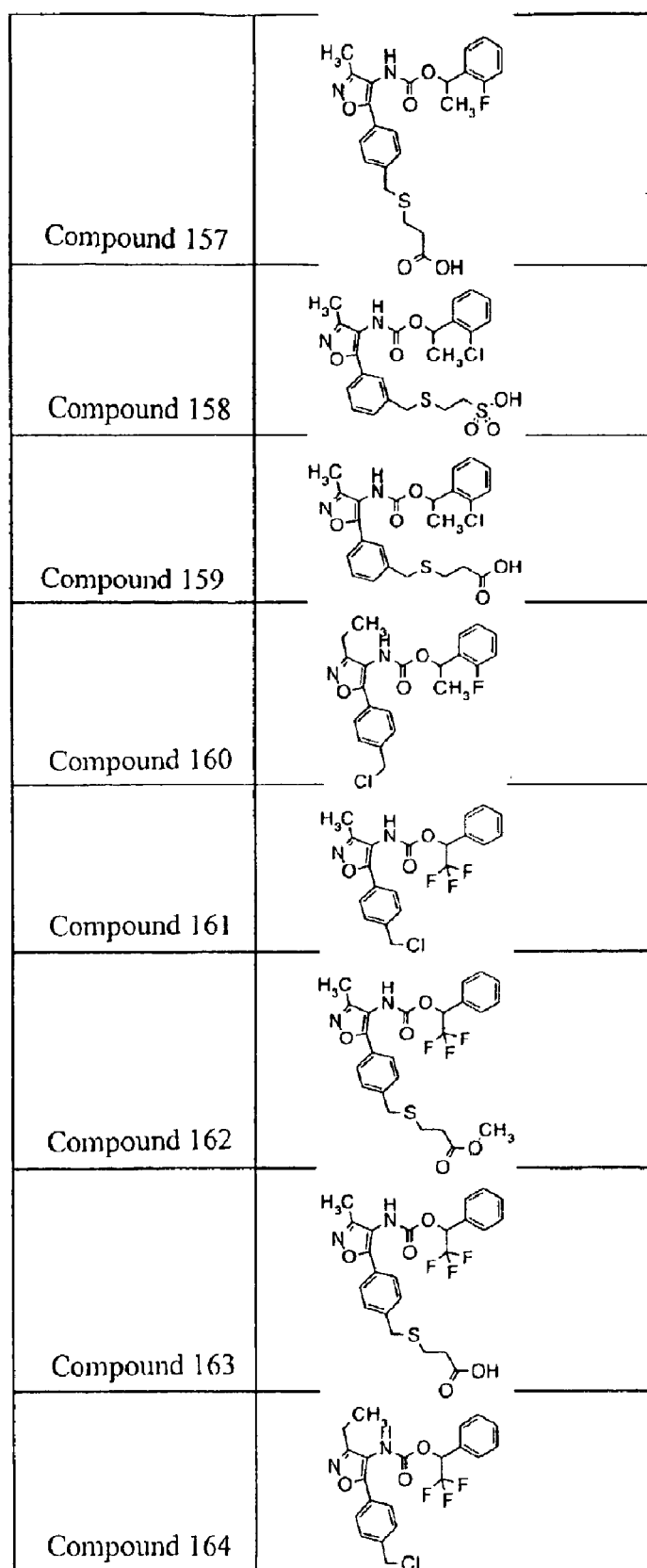
Figure 1I:
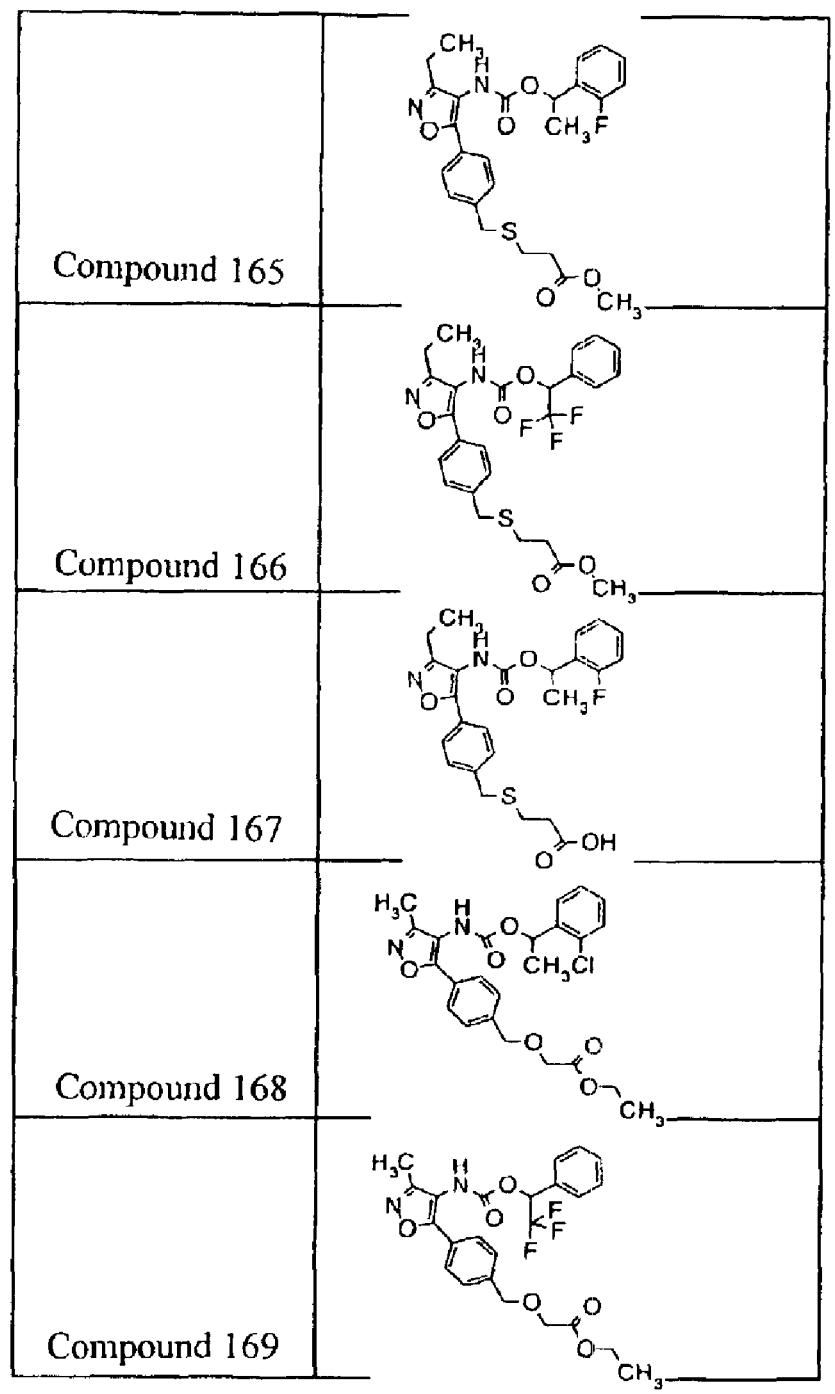

The term "optionally substituted" used herein means that the group of interest may optionally have one or more substituents. The term "optionally halogenated" means that the group of interest may be optionally substituted by at least one halogen atom.

Examples of a halogen atom, various groups, and substituents according to the present invention used herein include, but not limited to, the following.

Examples of a halogen atom include a fluorine atom, a chlorine atom, a bromine atom, and an iodine atom.

Examples of alkyl include straight chain or branched $C_{1-20}$ alkyl such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl.

Examples of cycloalkyl include $C_{3-6}$ cycloalkyl such as cyclopropyl, cyclobutyl, cyclopentyl, and cyclohexyl.

Examples of alkoxy include straight chain or branched $C_{1-20}$ alkoxy such as methoxy, ethoxy, n-propoxy, isopropoxy, n-butoxy, isobutoxy, sec-butoxy, tert-butoxy, pentyloxy, hexyloxy, heptyloxy, and octyloxy.

Examples of aryl include phenyl, tolyl, and naphthyl.

Examples of aryloxy include aryl-O— such as phenoxy, tolyloxy, and naphthyloxy.

Examples of heterocycle include aromatic heterocycle and nonaromatic heterocycle, for example, four- to seven-membered or fused heterocycle containing at least one hetero atom selected from an oxygen atom, a nitrogen atom, and a sulfur atom such as azetidinyl, thienyl, furyl, pyrrolyl, imidazolyl, pyrazolyl, thiazolyl, isothiazolyl, oxazolyl, isoxazolyl, furazanyl, pyrrolidinyl, pyrrolinyl, imidazolydinyl, imidazolinyl, pyrazolydinyl, pyrazolinyl, 1,3,4-oxadiazolyl, 1,2,3-thiadiazolyl, 1,2,4-thiadiazolyl, 1,3,4-thiadiazolyl, 1,2,3-triazolyl, 1,2,4-triazolyl, tetrazolyl, thiatriazolyl, pyridyl, pyrazinyl, pyrimidinyl, pyridazinyl, piperidinyl, piperazinyl, pyranyl, morpholinyl, 1,2,4-triazinyl, benzothienyl, naphthothienyl, benzofuryl, isobenzofuryl, chromenyl, indolizinyl, isoindolyl, indolyl, indazolyl, purinyl, quinolyl, isoquinolyl, phthalazinyl, naphthylizinyl, quinoxalinyl, quinazolinyl, cinnolinyl, pteridinyl, acridinyl, isochromanyl, chromanyl, indolinyl, isoindolinyl, benzoxazolyl, triazolopyridyl, tetrazolopyridazinyl, tetrazolopyrimidinyl, thiazolopyridazinyl, thiadiazolopyridazinyl, triazolopyridazinyl, benzimidazolyl, benzthiazolyl, benzothiadiazolyl, 1,2,3,4-tetrahydroquinolyl, imidazo[1,2-b][1,2,4]triazinyl, and quinuclidinyl.

Examples of acyl include acyl such as formyl, $C_{2-12}$ alkanoyl such as acetyl or propionyl, aroyl such as benzoyl or naphthoyl, and heterocyclic carbonyl such as nicotinoyl, thenoyl, pyrrolidino carbonyl, or furoyl.

Examples of monoalkylamino or dialkylamino include mono- or di-straight chain or branched $C_{1-6}$ alkylamino such as methylamino, ethylamino, n-propylamino, isopropylamino, n-butylamino, sec-butylamino, tert-butylamino, pentylamino, hexylamino, dimethylamino, diethylamino, di-n-propylamino, ethylmethylamino, methyl n-propylamino, and butylethylamino.

Examples of cyclic amino include five- to nine-membered cyclic amino optionally containing, in addition to a nitrogen atom, 1 to 3 hetero atoms such as an oxygen atom or a sulfur atom, for example, pyrrolidino, piperidino, morpholino, and iomorpholino.

Examples of lower alkyl include straight chain or branched $C_{1-6}$ alkyl such as methyl, ethyl, n-propyl, isopropyl, n-butyl, sec-butyl, isobutyl, tert-butyl, and pentyl.

In general formula [1], [2] or [5], R3 and R4 may form a five- to ten-membered cyclic structure together with a carbon atom to which they bind. Such structures include, for example, optionally substituted saturated or unsaturated monocyclic or fused polycyclic hydrocarbon and monocyclic or fused heterocycle containing hetero atoms such as a nitrogen atom, an oxygen atom, or a sulfur atom, such as cyclohexenyl, indanyl, or tetrahydronaphthyl.

The salt of the compound of the present invention includes conventional salt, for example, salt of a basic group such as amino or salt of an acidic group such as carboxyl. Examples of a salt of basic group include: salt with mineral acid such as hydrochloric acid, sulfuric acid, nitric acid, and phosphoric acid; salt with organic carboxylic acid such as formic acid, acetic acid, trichloroacetic acid, trifluoroacetic acid, oxalic acid, fumaric acid, maleic acid, citric acid, and tartaric acid; and salt with sulfonic acid such as methanesulfonic acid, benzenesulfonic acid, p-toluenesulfonic acid, and naphthalenesulfonic acid. Examples of a salt of acidic group include: salt with alkali metal such as sodium and potassium; salt with alkaline earth metal such as calcium and magnesium; ammonium salt; and salt with nitrogen-containing organic base such as trimethylamine, triethylamine, tributylamine, N,N-dimethylaniline, N-methylpiperidine, N-methylmorpholine, diethylamine, dicyclohexylamine, dibenzylamine, pyridine, guanidine, hydrazine, and quinine. The salt of the compound of the present invention preferably includes pharmaceutically acceptable salt of, for example, hydrochloric acid, sulfuric acid, nitric acid, phosphoric acid, formic acid, acetic acid, oxalic acid, fumaric acid, maleic acid, citric acid, sulfonic acid, and tartaric acid.

The method for producing the azole compound of the present invention will be described below.

The azole compound represented by general formula [1] can be produced utilizing the Curtius rearrangement shown in the following Reaction path (I).

In this method, the starting material, an azole carboxylic acid, was dissolved in a suitable solvent (e.g., toluene) and was reacted with an azide compound (e.g., diphenyl phosphoryl azide) to produce isocyanate. Thereafter, the isocyanate was reacted with a suitable alcohol to produce carbamate (Reaction path (I)).

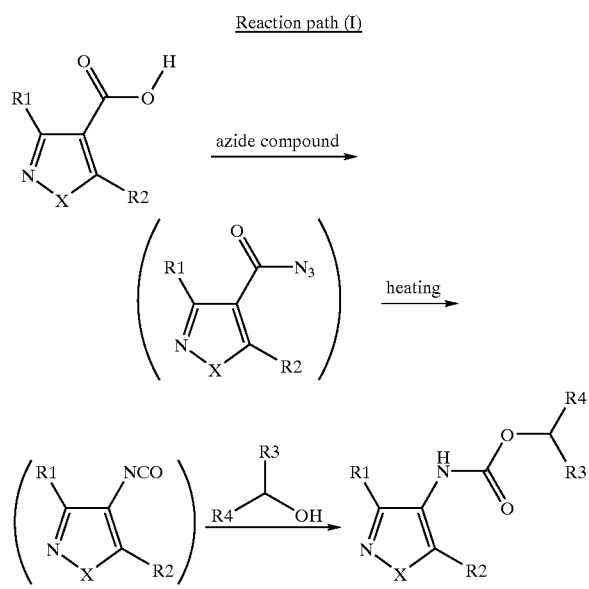

Reaction path (I)

In the Reaction path (I), R1, R2, R3, and R4 are as defined above.

The starting material, which is necessary for synthesizing the compound of the present invention, is commercially available or can be produced by the Reaction path (II) shown below (Synthesis, 1994, (9), 898 and thereinafter and Heterocycles, 1995, (41), 175 and thereinafter) or a conventional method shown in Reaction path (III).

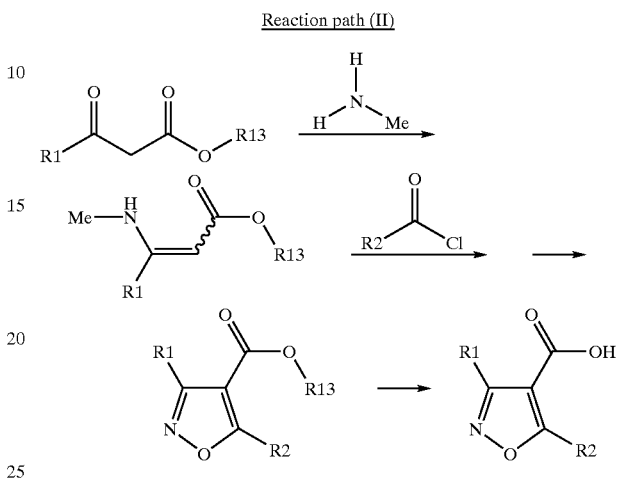

Reaction path (II)

In the Reaction path (II), R1 and R2 are as defined above and R13 represents straight chain or branched lower alkyl.

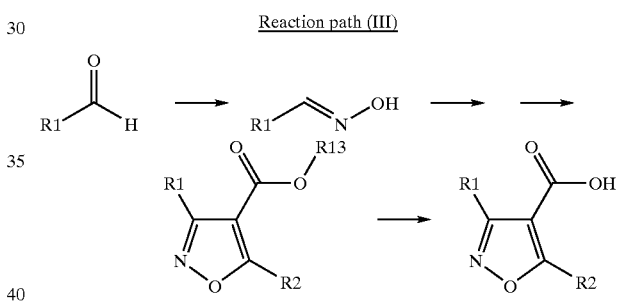

Reaction path (III)

In the Reaction path (III), R1, R2, and R13 are as defined above.

The compounds and the salts thereof according to the present invention are useful as an antagonist on lysophosphatidic acid (LPA) receptor and exhibit excellent actions as preventive and therapeutic agents for restenosis after percutaneous transluminal coronary angioplasty (PTCA), arteriosclerosis, artery obstruction, malignant and benign proliferative diseases, various inflammatory diseases, kidney diseases, proliferation of tumor cells, invasion and metastasis of carcinoma, cerebral or periphery nerve disorders and the like. Regarding the association between the LPA and the disease state, reference can be made to the literature cited in the section of the BACKGROUND ART.

When the compound of the present invention is used as a medicine, pharmaceutic aids such as an excipient, a carrier, and a diluent, which are commonly used in the preparation of formulations, may be suitably mixed. The compound can be orally or parenterally administered through conventional forms, for example, tablets, powders, granules, pills, suspensions, capsules, syrups, emulsions, liquid formulations, powder formulations, suppositories, ointments, patches, or injections. The method of administration, the dosage, and the frequency of administration, can be suitably selected depending on the age, weight, and symptom of the patient. In general, the administration can be orally or parenterally carried out (for example, by injection, drip infusion, percutaneous administration, or administration at rectal site) in the range of 0.1 to 5,000 mg, preferably in the range of 1 to 1,000 mg, per day to an adult, in a single dose or several separate doses.

The above-described various agents are formulated according to conventional methods. For example, when formulated into the form of solid formulations for oral administration such as tablets, powders, and granules, carriers usable herein include: excipients such as lactose, saccharose, sodium chloride, glucose, starch, calcium carbonate, kaolin, crystalline cellulose, calcium hydrogenphosphate, and alginic acid; binders such as simple syrup, liquid glucose, a starch solution, a gelatin solution, polyvinyl alcohol, polyvinyl ether, polyvinyl pyrrolidone, carboxymethylcellulose, shellac, methylcellulose, ethylcellulose, sodium alginate, gum Arabic, hydroxypropylmethylcellulose, hydroxypropylcellulose, water, and ethanol; disintegrating agents such as dried starch, alginic acid, agar powder, starch, crosslinking polyvinylpyrrolidone, crosslinking carboxymethylcellulose sodium, carboxymethylcellulose calcium, and sodium starch glycolate; disintegration inhibitors such as stearyl alcohol, stearic acid, cocoa butter, and hydrogenated oil; absorbefacients such as quaternary ammonium salt and sodium lauryl sulfate; absorbents such as starch, lactose, kaolin, bentonite, silicic anhydride, hydrous silicon dioxide, magnesium aluminometasilicate, and colloidal silica; and lubricants such as purified talc, stearate, and polyethylene glycol.

If necessary, conventional coatings may be applied to make tablets, for example, a sugar-coated tablet, a gelatin-encapsulated tablet, a gastric coated tablet, an enteric coated tablet, or a water-soluble film-coated tablet.

The capsule form can be prepared through mixing with various carriers as mentioned above, followed by filling into a hard gelatin capsule, a soft capsule or the like.

The liquid formulation can be an aqueous or oleaginous suspension, a solution, a syrup, or an elixir and can be prepared in accordance with conventional methods using conventional additives.

When formulated into the form of a suppository, a suitable absorbefacient can be added as a carrier, for example, polyethylene glycol, cocoa butter, lanoline, higher alcohol, esters of higher alcohol, gelatin, semi-synthetic glyceride, or Witepsol (registered trademark: Dynamite Novel).

When formulated into an injectable form, examples of carriers usable herein include: diluents such as water, ethyl alcohol, macrogol, propylene glycol, citric acid, acetic acid, phosphoric acid, lactic acid, sodium lactate, sulfuric acid, and sodium hydroxide; pH adjusters and buffers such as sodium citrate, sodium acetate, and sodium phosphate; and stabilizers such as sodium pyrosulfite, ethylenediaminetetraacetic acid, thioglycolic acid, and thiolactic acid. In this case, salt, glucose, mannitol, or glycerin may be contained in a medical formulation in a sufficient amount to prepare an isotonic solution and a conventional solubilizer, soothing agent, local anesthetic or the like may be added.

When formulated into the form of ointments, for example, paste, cream, and gel, a commonly used base, stabilizer, wetting agent, preservative and the like are optionally compounded and, in accordance with a conventional method, mixed and prepared. Examples of the bases usable herein include white petrolatum, polyethylene, paraffin, glycerin, cellulose derivative, polyethylene glycol, silicon, and bentonite. Preservatives usable herein include methyl p-hydroxybenzoate, ethyl p-hydroxybenzoate, and propyl p-hydroxybenzoate.

The present invention will be described in more detail with reference to the following examples. These examples, however, are not intended to limit the scope of the present invention. With reference to the description on the present invention and the following specific examples, a person who has ordinary skill in the art would be able to develop various compounds included in the scope of the present invention or the scope equivalent thereto and could confirm the effects thereof. Accordingly, the present invention is intended to include, unless departing from the scope of the invention specified in the claims, any scopes equivalent to the scope of the present invention.

EXAMPLES

Example 1

Synthesis of Compound 1: 3-Furylmethyl N-(5-methyl-3-phenyl-4-isoxazolyl)carbamate

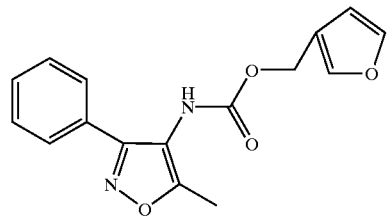

5-Methyl-3-phenyl-4-isoxazole carboxylic acid (50 mg) was dissolved in anhydrous toluene (1.0 ml). Subsequently, diphenylphosphoryl azide (81 mg) and triethylamine (30 mg) were added at room temperature and the mixture was stirred at 120° C. for 1 hour. After the mixture was allowed to stand at room temperature, 3-furanmethanol (24 mg) was added thereto and the mixture was stirred again at 120° C. for 2 hours. After the completion of the reaction, the mixture was allowed to cool at room temperature and distilled water was added thereto. Thereafter, the reaction product was extracted by liquid separation using chloroform and washed with saturated solution of sodium chloride. The product was dried over sodium sulfate to concentrate and the residue was purified by silicagel column chromatography using a hexane-acetone elution system. Thus, the title compound 1 (29 mg, yield 40.0%) was obtained.

$^1$H-NMR (CDCl$_3$, 400 MHz): δ7.39–7.65 (5H, m), 6.23–6.47 (2H, m), 4.55–4.58 (3H, m), 1.61 (3H, s) Mass spectrometry (FD-MS): 298 (M$^+$)

Example 2

Synthesis of Compound 2: Benzyl N-(5-methyl-3-phenyl-4-isoxazolyl)carbamate

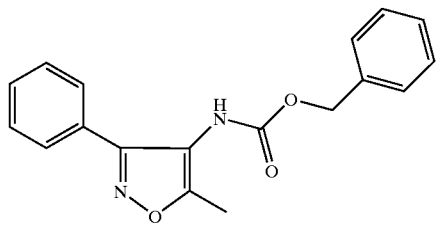

The title compound 2 was obtained in the same manner as used in Example 1.

¹H-NMR (CDCl₃, 400 MHz): δ7.61 (7H, d, J=6.83 Hz), 7.39 (2H, m), 4.91 (3H, bs), 2.17 (3H, bs) Mass spectrometry (ESI-MS): 309(M⁺+1)

Example 3

Synthesis of Compound 3: 1-(2-Chlorophenyl)ethyl N-(3-methyl-5-phenyl-4-isoxazolyl)carbamate

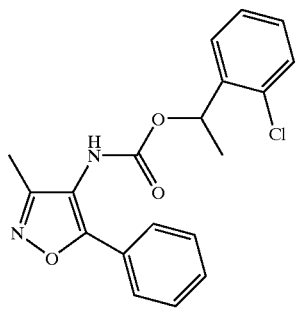

Acetaldoxime (500 mg) was dissolved in dimethylformamide (2 ml), and under ice cooling, N-bromosuccinimide (1.66 g) dissolved in dimethylformamide (4 ml) was added dropwise. The mixture was stirred at 0° C. for 30 minutes, a methanol solution comprising ethyl benzoylacetate (3.26 g) and metallic sodium (700 mg) was added thereto, and the mixture was stirred at that temperature for 1 hour. After the completion of the reaction, distilled water was added thereto, and the reaction product was extracted by liquid separation using ethyl acetate and washed with saturated solution of sodium chloride. The product was dried over sodium sulfate to concentrate, and the residue was purified by flash column chromatography using a hexane-ethyl acetate elution system. Thus, a useful intermediate, i.e., ethyl 3-methyl-5-phenyl-4-isoxazole carboxylate (1.45 g, yield 74.4%) was obtained.

The ethyl 3-methyl-5-phenyl-4-isoxazole carboxylate (1.45 g) obtained in the above reaction was dissolved in ethanol (45 ml) and distilled water (15 ml), potassium hydroxide (1.3 g) was added thereto at room temperature, and the mixture was stirred under heat reflux for 1 hour. After the completion of the reaction, the mixture was concentrated to remove ethanol, distilled water was added thereto, and the mixture was acidified (pH=4) using 1%-aqueous hydrochloric acid. Extraction by liquid separation using dichloromethane and washing with a saturated saline solution were then performed. The product was dried over sodium sulfate followed by concentration and the residue was purified by silica gel column chromatography using a chloroform-methanol elution system. Thus, 3-methyl-5-phenyl-4-isoxazole carboxylic acid (215 mg, yield 16.9%), a starting compound for the Curtius reaction described in Example 1, was obtained.

3-Methyl-5-phenyl-4-isoxazole carboxylic acid (70 mg) was dissolved in anhydrous toluene (0.7 ml). Subsequently, diphenylphosphoryl azide (89 μl) and triethylamine (58 μl) were added at room temperature and the mixture was stirred at 120° C. for 1 hour. After the mixture was allowed to stand at room temperature, 2-chloro-α-methyl benzyl alcohol (46 μl) was added, and the mixture was stirred again at 120° C. for 2 hours. After the completion of the reaction, the mixture was allowed to cool at room temperature and distilled water was added thereto. Thereafter the reaction product was extracted by liquid separation using chloroform and washed with saturated solution of sodium chloride. The product was dried over sodium sulfate to concentrate and the residue was purified by silica gel column chromatography using a hexane-acetone elution system. Thus, the title compound 3 (18 mg, yield 14.6%) was obtained.

¹H-NMR (CDCl₃, 400 MHz): δ7.00–7.85 (9H, m), 6.15–6.25 (2H, m), 2.23 (3H, s), 1.30–1.70 (3H, m) Mass spectrometry (FD-MS): 356(M⁺)

Example 4

Synthesis of Compound 4: 1-(2-Chlorophenyl)ethyl N-(5-methyl-3-phenyl-4-isoxazolyl)carbamate

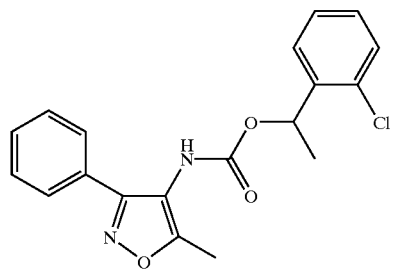

The title compound 4 was obtained in the same manner as used in Example 1.

¹H-NMR (CDCl₃, 400 MHz): δ7.25–7.80 (9H, m), 6.19 (1H, bs), 5.88 (1H, bs), 2.40 (3H, s), 1.52–1.65 (3H, m) Mass spectrometry (FD-MS): 356(M⁺)

Example 5

Synthesis of Compound 5: 1-(2-Chlorophenyl)ethyl N-[5-methyl-3-(4-methylphenyl)-4-isoxazolyl]carbamate

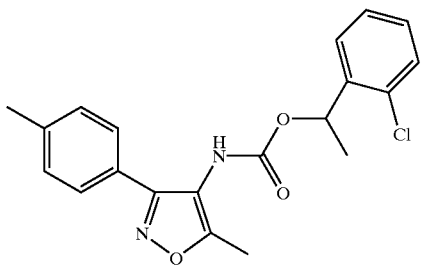

The title compound 5 was obtained in the same manner as used in Example 3.

¹H-NMR (CDCl₃, 400 MHz): δ7.20–7.70 (8H, in), 6.18 (1H, bs), 5.87 (1H, bs), 2.40 (3H, s), 2.39 (3H, s), 1.50–1.64 (3H, m) Mass spectrometry (FD-MS): 371(M⁺)

Example 6

Synthesis of Compound 6: 1-(2-Chlorophenyl)ethyl N-[5-methyl-3-(4-nitrophenyl)-4-isoxazolyl]carbamate

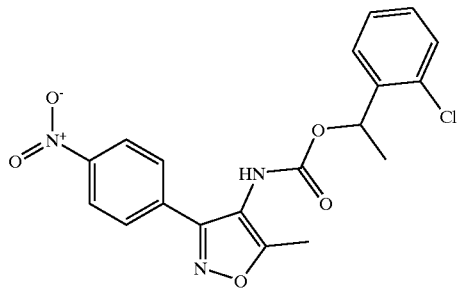

The title compound 6 was obtained in the same manner as used in Example 3.

Mass spectrometry (FD-MS): 401(M⁺)

Example 7

Synthesis of Compound 7: Benzyl N-(3-methyl-5-phenyl-4-isoxazolyl)carbamate

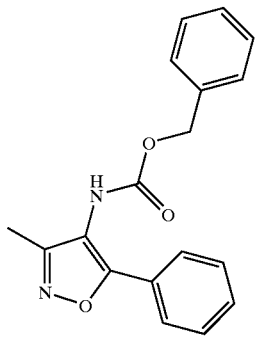

The title compound 7 was obtained in the same manner as used in Example 3.

$^1$H-NMR (CDCl$_3$, 400 MHz): δ7.40–7.80 (10H, m), 6.00 (1H, bs), 5.22 (2H, s), 2.27 (3H, s) Mass spectrometry (FD-MS): 308 (M⁺)

Example 8

Synthesis of Compound 8: 1-(2-Chlorophenyl)ethyl N-[3-[4-(hydroxymethyl)phenyl]-5-methyl-4-isoxazolyl]carbamate

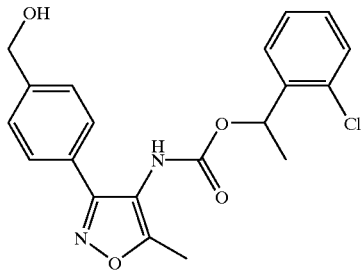

The title compound 8 was obtained in the same manner as used in Example 3.

$^1$H-NMR (CDCl$_3$, 400 MHz): δ7.00–7.70 (8H, m), 6.18 (1H, bs), 5.96 (1H, bs), 4.73 (2H, s), 2.39 (3H, s), 1.50–1.78 (3H, m) Mass spectrometry (FD-MS): 386 (M⁺)

Example 9

Synthesis of Compound 9: (1R)-1-Phenylethyl N-(5-methyl-3-phenyl-4-isoxazolyl)carbamate

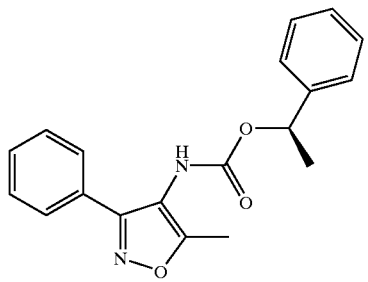

The title compound 9 was obtained in the same manner as used in Example 1.

$^1$H-NMR (CDCl$_3$, 400 MHz): δ7.00–7.70 (10H, m), 5.85 (1H, bs), 2.37 (3H, s), 1.58 (3H, bs) Mass spectrometry (FD-MS): 322 (M⁺)

Example 10

Synthesis of Compound 10: (1S)-1-Phenylethyl N-(5-methyl-3-phenyl-4-isoxazolyl)carbamate

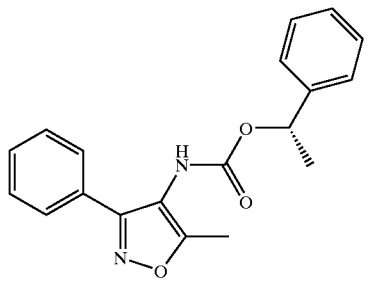

The title compound 10 was obtained in the same manner as used in Example 1.

$^1$H-NMR (CDCl$_3$, 400 MHz): δ7.00–7.70 (10H, m), 5.85 (1H, bs), 2.37 (3H, s), 1.58 (3H, bs) Mass spectrometry (FD-MS): 322 (M⁺)

Example 11

Synthesis of Compound 11: 1-(2-Chlorophenyl) ethyl N-[5-methyl-3-[4-(trifluoromethoxy)phenyl]-4-isoxazolyl]carbamate

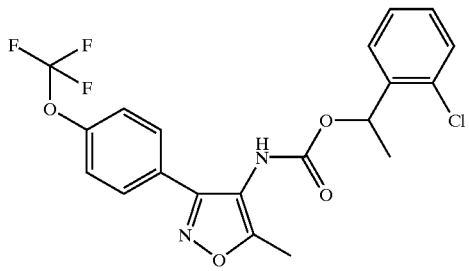

The title compound 11 was obtained in the same manner as used in Example 3.

$^1$H-NMR (CDCl$_3$, 400 MHz): δ7.00–7.80 (8H, m), 6.18 (1H, bs), 5.87 (1H, bs), 2.41 (3H, s), 1.50–1.65 (3H, m) Mass spectrometry (FD-MS): 440 (M$^+$)

Example 12

Synthesis of Compound 12: 1-Phenylethyl N-(5-methyl-3-phenyl-4-isoxazolyl)carbamate

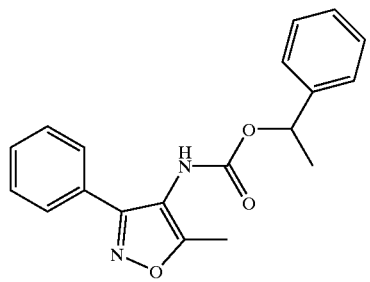

The title compound 12 was obtained in the same manner as used in Example 1.

$^1$H-NMR (CDCl$_3$, 400 MHz): δ7.00–7.70 (10H, m), 5.85 (1H, bs), 2.38 (3H, s), 1.52–1.66 (3H, m) Mass spectrometry (FD-MS): 322 (M$^+$)

Example 13

Synthesis of Compound 13: 1-(2-Chlorophenyl) ethyl N-[3-(3-bromophenyl)-5-methyl-4-isoxazolyl]carbamate

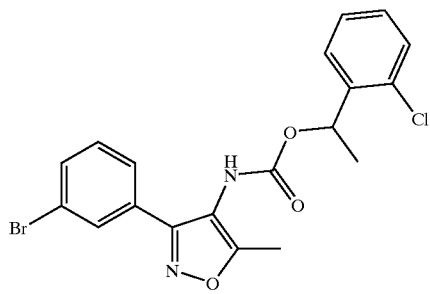

The title compound 13 was obtained in the same manner as used in Example 3.

$^1$H-NMR (CDCl$_3$, 400 MHz): δ7.85 (1H, s), 7.26–7.60 (7H, M), 6.18 (1H, bs), 5.88 (1H, bs), 2.40 (3H, s), 1.50–1.65 (3H, m) Mass spectrometry (FD-MS): 436 (M$^+$)

Example 14

Synthesis of Compound 14: 1-(2-Methylphenyl) ethyl N-(5-methyl-3-phenyl-4-isoxazolyl)carbamate

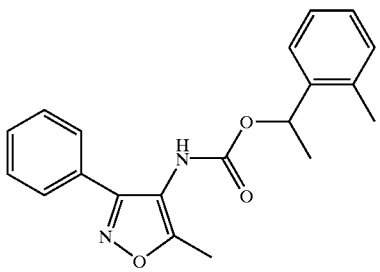

The title compound 14 was obtained in the same manner as used in Example 3.

$^1$H-NMR (CDCl$_3$, 400 MHz): δ7.00–7.70 (9H, m), 6.05 (1H, bs), 5.84 (1H, bs), 2.38 (3H, s), 2.38 (3H, s), 1.54 (3H, bs) Mass spectrometry (FD-MS): 336 (M$^+$)

Example 15

Synthesis of Compound 15: 1-(2-Chlorophenyl) ethyl N-[5-methyl-3-[3-(trifluoromethyl)phenyl]-4-isoxazolyl]carbamate

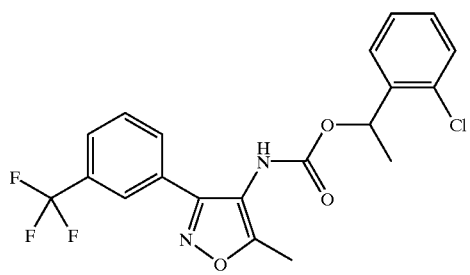

The title compound 15 was obtained in the same manner as used in Example 3.

$^1$H-NMR (CDCl$_3$, 400 MHz): δ7.98 (1H, s), 7.86 (1H, d, J=7.6 Hz), 7.71 (1H, d, J=8.0 Hz), 7.20–7.58 (5H, m), 6.19 (1H, bs), 5.89 (1H, bs), 2.42 (3H, s), 1.50–1.65 (3H, m) Mass spectrometry (FD-MS): 424 (M$^+$)

Example 16

Synthesis of Compound 16: 1-(2-Chlorophenyl)ethyl N-[3-(4-fluorophenyl)-5-methyl-4-isoxazolyl]carbamate

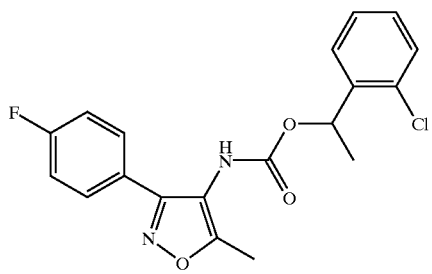

The title compound 16 was obtained in the same manner as used in Example 3.

¹H-NMR (CDCl₃, 400 MHz): δ7.07–7.70 (8H, m), 6.18 (1H, bs), 5.85 (1H, bs), 2.40 (3H, s), 1.50–1.65 (3H, m) Mass spectrometry (FD-MS): 374 (M⁺)

Example 17

Synthesis of Compound 17: (1R)-1-(2-Chlorophenyl)ethyl N-(5-methyl-3-phenyl-4-isoxazolyl)carbamate

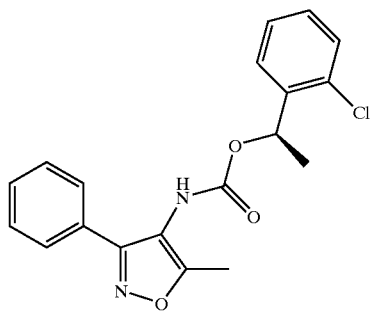

The title compound 17 was obtained in the same manner as used in Example 1.

¹H-NMR (CDCl₃, 400 MHz): δ7.00–7.72 (9H, m), 6.19 (1H, bs), 5.88 (1H, bs), 2.41 (3H, s), 1.52–1.65 (3H, m) Mass spectrometry (FD-MS): 356 (M⁺)

Example 18

Synthesis of Compound 18: (1R)-1-(2-Chlorophenyl)ethyl N-(3-methyl-5-phenyl-4-isoxazolyl)carbamate

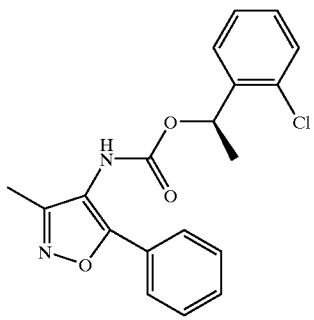

The title compound 18 was obtained in the same manner as used in Example 3. Mass spectrometry (FD-MS): 356 (M⁺)

Example 19

Synthesis of Compound 19: 1-(2-Fluorophenyl)ethyl N-(5-methyl-3-phenyl-4-isoxazolyl)carbamate

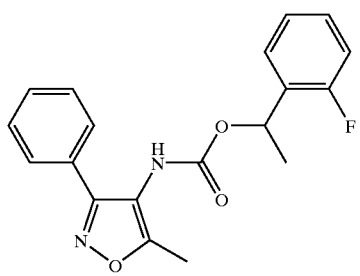

The title compound 19 was obtained in the same manner as used in Example 1.

¹H-NMR (CDCl₃, 400 MHz): δ6.80–7.70 (9H, m), 6.08 (1H, bs), 5.87 (1H, bs), 2.37 (3H, s), 1.50–1.70 (3H, m) Mass spectrometry (ESI-MS): 341, 342 (M⁺+1)

Example 20

Synthesis of Compound 20: 1-(2-Chlorophenyl)ethyl N-[3-(2-fluorophenyl)-5-methyl-4-isoxazolyl]carbamate

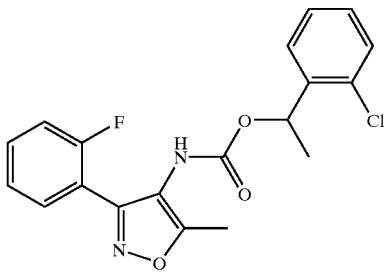

The title compound 20 was obtained in the same manner as used in Example 3.

¹H-NMR (CDCl₃, 400 MHz): δ7.16–7.65 (8H, m), 6.05–6.15 (2H, m), 2.41 (3H, s), 1.50–1.58 (3H, m) Mass spectrometry (FD-MS): 374 (M⁺)

Example 21

Synthesis of Compound 21: 1-(2-Chlorophenyl)ethyl N-[3-(3-fluorophenyl)-5-methyl-4-isoxazolyl]carbamate

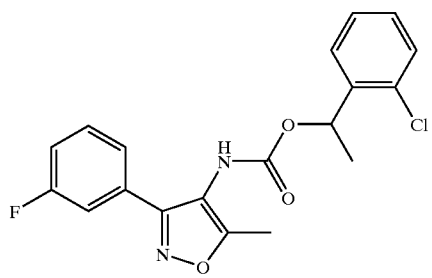

The title compound 21 was obtained in the same manner as used in Example 3.

¹H-NMR (CDCl₃, 400 MHz): δ7.00–7.50 (8H, m), 6.18 (1H, bs), 5.89 (1H, bs), 2.40 (3H, s), 1.50–1.65 (3H, m) Mass spectrometry (FD-MS): 374 (M⁺)

Example 22

Synthesis of Compound 22: (1R)-1-(2-Bromophenyl)ethyl N-(5-methyl-3-phenyl-4-isoxazolyl)carbamate

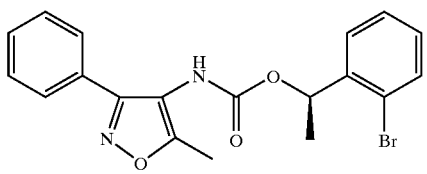

The title compound 22 was obtained in the same manner as used in Example 1.

¹H-NMR (CDCl₃, 400 MHz): δ6.75–7.70 (9H, m), 6.06 (1H, bs), 5.81 (1H, bs), 2.33 (3H, s), 1.20–1.70 (3H, m) Mass spectrometry (FD-MS): 400, 402 (M⁺)

Example 23

Synthesis of Compound 23: 1-(2-Bromophenyl)ethyl N-(5-methyl-3-phenyl-4-isoxazolyl)carbamate

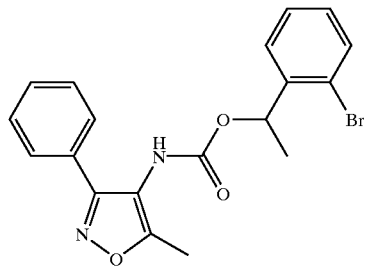

The title compound 23 was obtained in the same manner as used in Example 1.

¹H-NMR (CDCl₃, 400 MHz): δ6.80–7.70 (9H, m), 6.11 (1H, bs), 5.86 (1H, bs), 2.38 (3H, s), 1.45–1.62 (3H, m) Mass spectrometry (ESI-MS): 403 (M⁺+1)

Example 24

Synthesis of Compound 24: (1R)-1-(2-Bromophenyl)ethyl N-[3-chloro-5-(2-chlorophenyl)-4-isothiazolyl]carbamate

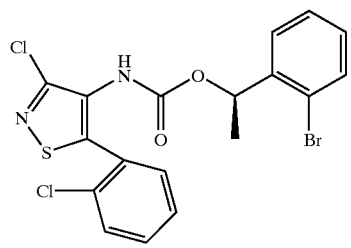

The title compound 24 was obtained in the same manner as used in Example 1.

¹H-NMR (CDCl₃, 400 MHz): δ7.10–7.52 (8H, m), 6.21 (1H, bs), 5.99 (1H, q, J=6.5 Hz), 1.40–1.50 (3H, m) Mass spectrometry (FD-MS): 470, 472 (M⁺)

Example 25

Synthesis of Compound 25: 1-Phenylethyl N-[3-chloro-5-(2-chlorophenyl)-4-isothiazolyl]carbamate

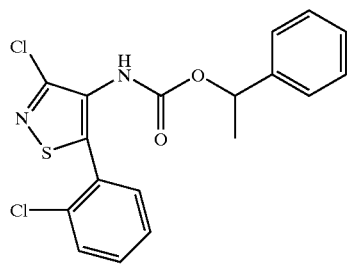

The title compound 25 was obtained in the same manner as used in Example 1.

¹H-NMR (CDCl₃, 400 MHz): δ7.20–7.60 (9H, m), 6.21 (1H, bs), 5.73 (1H, q, J=6.6 Hz), 1.40–1.50 (3H, m) Mass spectrometry (FD-MS): 392 (M⁺)

Example 26

Synthesis of Compound 26: 1-(2-Fluorophenyl) ethyl N-[3-chloro-5-(2-chlorophenyl)-4-isothiazolyl] carbamate

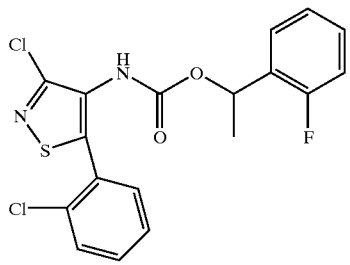

The title compound 26 was obtained in the same manner as used in Example 1.

$^1$H-NMR (CDCl$_3$, 400 MHz): δ6.98–7.50 (8H, m), 5.97 (1H, q, J=6.6 Hz), 1.45–1.52 (3H, m) Mass spectrometry (FD-MS): 410 (M$^+$)

Example 27

Synthesis of Compound 27: 1-Phenylethyl N-[3-methyl-5-(3-methylphenyl)-4-isoxazolyl]carbamate

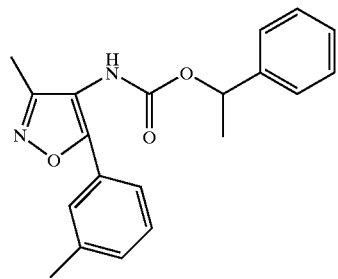

Methyl 3-oxobutanoate (29.4 g) was dissolved in methanol (30 ml), then a 40%-methylamine-methanol solution (32 ml) was added dropwise at room temperature, and the mixture was stirred for 1 hour. After the completion of the reaction, the reaction solution as such was concentrated, and then dried using a vacuum pump to obtain methyl 3-(methylamino)-2-butenoate (31.8 g, yield 97%). Subsequently, methyl 3-(methylamino)-2-butenoate (1.0 g) was dissolved in tetrahydrofuran (15 ml) and pyridine (0.63 ml) was added dropwise at room temperature. Under ice cooling, m-toluyl chloride (1.22 ml) was added dropwise and the mixture was stirred at room temperature for 1 hour. After the completion of the reaction, distilled water was added, and the reaction product was extracted by liquid separation using ether and then washed with a saturated saline solution. The product was dried over sodium sulfate to concentrate and the residue was dried using a vacuum pump. Subsequently, the residue was dissolved in an acetic acid (15 ml). Then, hydroxylamine hydrochloride (0.54 g) was added at room temperature, and the product was heated under reflux for 30 minutes. After the completion of the reaction, saturated aqueous solution of sodium hydrogencarbonate was added to neutralize the reaction system, and the product was extracted by liquid separation using ether. The resultant organic layer was washed with saturated aqueous solution of sodium chloride and dried over sodium sulfate to concentrate. The residue was purified by silica gel column chromatography using a hexane-acetone elution system to obtain methyl 3-methyl-5-(3-methylphenyl)-4-isoxazole carboxylate (183 mg, yield 10.2%).

Methyl 3-methyl-5-(3-methylphenyl)-4-isoxazole carboxylate (183 mg) was dissolved in tetrahydrofuran/distilled water=4/1 (2 ml). Lithium hydroxide (66.5 mg) was added at room temperature, and the mixture was stirred at that temperature for 20 hours. After the completion of the reaction, 5%-aqueous hydrochloric acid was added to acidify the system, and the reaction product was extracted by liquid separation using chloroform and washed with saturated aqueous solution of sodium chloride. The product was dried over sodium sulfate to concentrate and the residue was dried using a vacuum pump. Thus, a useful intermidiate, i.e., 3-methyl-5-(3-methylphenyl)-4-isoxazole carboxylic acid (169 mg, yield 98%) was obtained.

3-Methyl-5-(3-methylphenyl)-4-isoxazole carboxylic acid (80 mg) was dissolved in anhydrous toluene (2.0 ml). Subsequently, diphenylphosphoryl azide (95 μl) and triethylamine (62 μl) were added at room temperature and the mixture was stirred at 120° C. for 1 hour. After the product was allowed to stand at room temperature, 1-phenyl-ethanol (67 μl) was added and the mixture was stirred again at 120° C. for 2 hours. After the completion of the reaction, the reaction product was allowed to cool at room temperature, distilled water was added thereto, and the product was extracted by liquid separation using chloroform and washed with saturated aqueous solution of sodium chloride. The product was dried over sodium sulfate to concentrate and the residue was purified by silica gel column chromatography using a hexane-acetone elution system. Thus, the title compound 27 (65.9 mg, yield 53.3%) was obtained.

$^1$H-NMR (CDCl$_3$, 400 MHz): δ7.20–7.60 (9H, m), 5.89 (2H, bs), 2.36 (3H, s), 2.23 (3H, s), 1.50–1.65 (3H, m) Mass spectrometry (ESI-MS): 337 (M$^+$+1)

Example 28

Synthesis of Compound 28: 1-(2-Chlorophenyl) ethyl N-[3-methyl-5-(3-methylphenyl)-4-isoxazolyl] carbamate

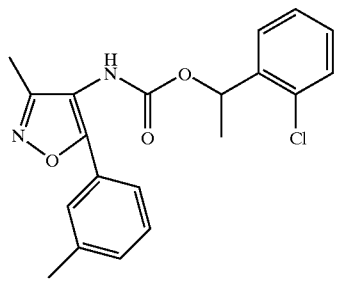

The title compound 28 was obtained in the same manner as used in Example 27.

$^1$H-NMR (CDCl$_3$, 400 MHz): δ7.23–7.65 (8H, m), 6.18–6.28 (1H, m), 5.98 (1H, bs), 2.38 (3H, s), 2.26 (3H, s), 1.50–1.57 (3H, m) Mass spectrometry (ESI-MS): 371 (M$^+$+1)

Example 29

Synthesis of Compound 29: 1-Phenylethyl N-[5-(3-fluorophenyl)-3-methyl-4-isoxazolyl]carbamate

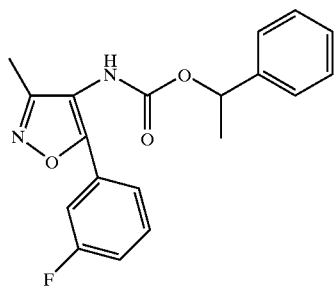

The title compound 29 was obtained in the same manner as used in Example 27.

$^1$H-NMR (CDCl$_3$, 400 MHz): δ7.10–7.60 (9H, m), 6.22 (1H, q, J=6.5 Hz), 6.03 (1H, bs), 2.25 (3H, s), 1.50–1.70 (3H, m) Mass spectrometry (ESI-MS): 341 (M$^+$+1)

Example 30

Synthesis of Compound 30: 1-(2-Chlorophenyl) ethyl N-[5-(3-fluorophenyl)-3-methyl-4-isoxazolyl] carbamate

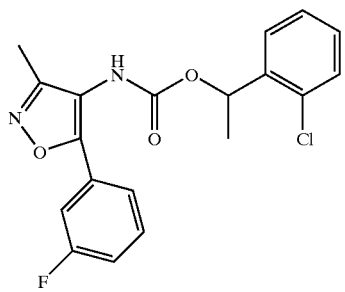

The title compound 30 was obtained in the same manner as used in Example 27.

$^1$H-NMR (CDCl$_3$, 400 MHz): δ7.09–7.58 (8H, m), 5.87 (1H, q, J=6.6 Hz), 2.22 (3H, s), 1.50–1.69 (3H, m) Mass spectrometry (ESI-MS): 375 (M$^+$+1)

Example 31

Synthesis of Compound 31: 1-Phenylethyl N-[5-(2-furyl)-3-methyl-4-isoxazolyl]carbamate

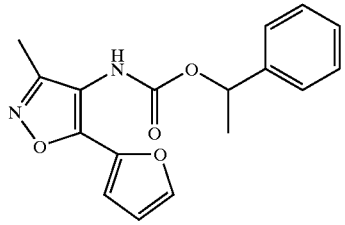

The title compound 31 was obtained in the same manner as used in Example 27.

$^1$H-NMR (CDCl$_3$, 400 MHz): δ7.50 (1H, s), 7.23–7.40 (5H, m), 6.82 (1H, s), 6.45–6.60 (1H, m), 6.26 (1H, bs), 5.87 (1H, q, J=6.6 Hz), 2.24 (3H, s), 1.50–1.70 (3H, m) Mass spectrometry (ESI-MS): 313 (M$^+$+1)

Example 32

Synthesis of Compound 32: 1-(2-Chlorophenyl) ethyl N-[5-(2-furyl)-3-methyl-4-isoxazolyl] carbamate

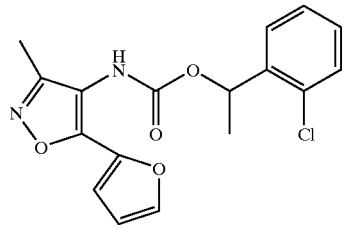

The title compound 32 was obtained in the same manner as used in Example 27.

$^1$H-NMR (CDCl$_3$, 400 MHz): δ7.53–7.57 (1H, m), 7.20–7.40 (4H, m), 6.86 (1H, s), 6.53 (1H, dd, J=1.7 Hz, J=3.4 Hz), 6.21 (1H, q, J=6.5 Hz), 2.27 (3H, s), 1.50–1.60 (3H, m) Mass spectrometry (ESI-MS): 347 (M$^+$+1)

Example 33

Synthesis of Compound 33: (1R)-1-(2-Bromophenyl)ethyl N-[5-(3-fluorophenyl)-3-methyl-4-isoxazolyl]carbamate

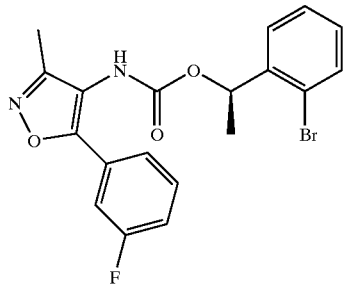

The title compound 33 was obtained in the same manner as used in Example 27.

$^1$H-NMR (CDCl$_3$, 400 MHz): δ7.06–7.60 (8H, m), 6.16 (1H, q, J=6.5 Hz), 6.08 (1H, bs), 2.25 (3H, s), 1.50–1.70 (3H, m) Mass spectrometry (ESI-MS): 419, 421 (M$^+$+1)

Example 34

Synthesis of Compound 34: 1-(2-Fluorophenyl) ethyl N-[5-(3-fluorophenyl)-3-methyl-4-isoxazolyl]carbamate

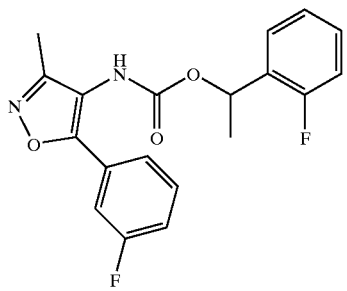

The title compound 34 was obtained in the same manner as used in Example 27.

$^1$H-NMR (CDCl$_3$, 400 MHz): δ7.00–7.60 (8H, m), 6.00–6.18 (2H, m), 2.24 (3H, s), 1.50–1.70 (3H, m) Mass spectrometry (ESI-MS): 359 (M$^+$+1)

Example 35

Synthesis of Compound 35: 1-Phenylethyl N-[5-[4-(trifluoromethoxy)phenyl]-3-methyl-4-isoxazolyl]carbamate

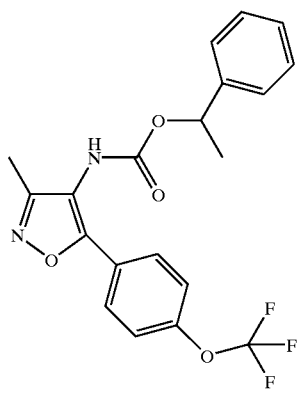

The title compound 35 was obtained in the same manner as used in Example 27.

$^1$H-NMR (CDCl$_3$, 400 MHz): δ7.00–7.80 (9H, m), 5.85 (1H, q, J=6.6 Hz), 2.21 (3H, s), 1, 45–1.65 (3H, m) Mass spectrometry (ESI-MS): 407 (M$^+$+1)

Example 36

Synthesis of Compound 36: 1-(2-Chlorophenyl) ethyl N-[5-[4-(trifluoromethoxy)phenyl]-3-methyl-4-isoxazolyl]carbamate

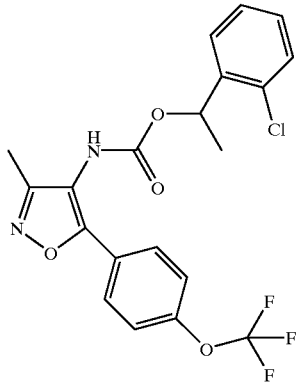

The title compound 36 was obtained in the same manner as used in Example 27.

$^1$H-NMR (CDCl$_3$, 400 MHz): δ7.72 (2H, bs), 6.80–7.50 (6H, m), 6.15 (1H, q, J=6.5 Hz), 5.90 (1H, bs), 2.19 (3H, s), 1.42–1.60 (3H, m) Mass spectrometry (ESI-MS): 441 (M$^+$+1)

Example 37

Synthesis of Compound 37: 1-Phenylethyl N-[3-methyl-5-(4-methylphenyl)-4-isoxazolyl]carbamate

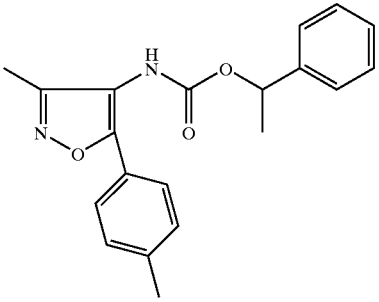

The title compound 37 was obtained in the same manner as used in Example 27.

$^1$H-NMR (CDCl$_3$, 400 MHz): δ7.62 (2H, bs), 7.15–7.45 (7H, m), 5.80–5.92 (2H, m), 2.39 (3H, s), 2.21 (3H, s), 1.50–1.67 (3H, m) Mass spectrometry (ESI-MS): 337 (M$^+$+1)

Example 38

Synthesis of Compound 38: 1-(2-Chlorophenyl) ethyl N-[3-methyl-5-(4-methylphenyl)-4-isoxazolyl]carbamate

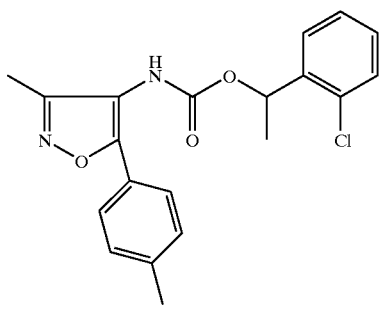

The title compound 38 was obtained in the same manner as used in Example 27.

$^1$H-NMR (CDCl$_3$, 400 MHz): δ7.65 (2H, bs), 6.90–7.60 (6H, m), 6.21 (1H, q, J=6.4 Hz), 5.98 (1H, bs), 2.40 (3H, s), 2.24 (3H, s), 1.50–1.70 (3H, m) Mass spectrometry (ESI-MS): 371 (M$^+$+1)

Example 39

Synthesis of Compound 39: 1-(2-Chlorophenyl) ethyl N-[5-(3-chlorophenyl)-3-methyl-4-isoxazolyl]carbamate

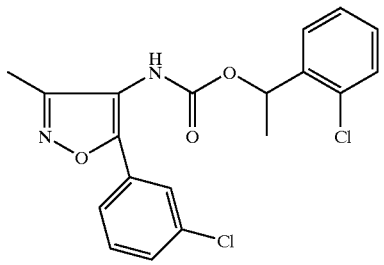

The title compound 39 was obtained in the same manner as used in Example 27.

$^1$H-NMR (CDCl$_3$, 400 MHz): δ7.71 (1H, s), 7.20–7.65 (7H, m), 6.16 (1H, q, J=6.6 Hz), 5.91 (1H, bs), 2.19 (3H, s), 1.40–1.60 (3H, m) Mass spectrometry (ESI-MS): 391 (M$^+$+1)

Example 40

Synthesis of Compound 40: 1-Phenylethyl N-[5-(4-fluorophenyl)-3-methyl-4-isoxazolyl]carbamate

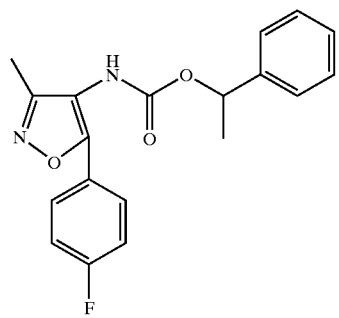

The title compound 40 was obtained in the same manner as used in Example 27.

$^1$H-NMR (CDCl$_3$, 400 MHz): δ7.70 (2H, bs), 7.00–7.50 (7H, m), 5.80–5.95 (2H, m), 2.22 (3H, s) 1.50–1.65 (3H, m) Mass spectrometry (ESI-MS): 341 (M$^+$+1)

Example 41

Synthesis of Compound 41: 1-(2-Chlorophenyl) ethyl N-[5-(4-fluorophenyl)-3-methyl-4-isoxazolyl]carbamate

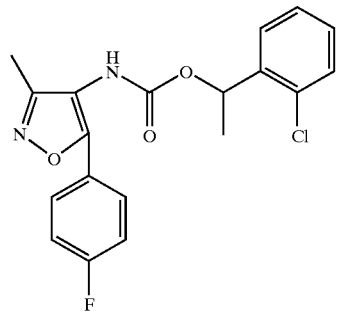

The title compound 41 was obtained in the same manner as used in Example 27.

$^1$H-NMR (CDCl$_3$, 400 MHz): δ7.75 (2H, bs), 6.80–7.60 (6H, m), 6.22 (1H, q, J=6.5 Hz), 5.96 (1H, bs), 2.25 (3H, s), 1.50–1.65 (3H, m) Mass spectrometry (ESI-MS): 375 (M$^+$+1)

Example 42

Synthesis of Compound 42: 1-Phenylethyl N-[5-(2-fluorophenyl)-3-methyl-4-isoxazolyl]carbamate

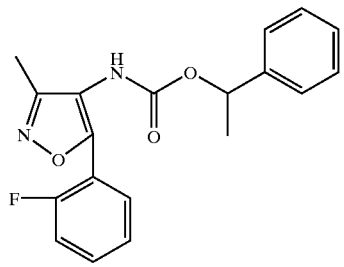

The title compound 42 was obtained in the same manner as used in Example 27.

$^1$H-NMR (CDCl$_3$, 400 MHz): δ7.64–7.70 (1H, m), 7.13–7.50 (8H, m), 6.18 (1H, bs), 5.82 (1H, q, J=6.6 Hz), 2.27 (3H, s), 1.56 (3H, bs) Mass spectrometry (ESI-MS): 341 (M$^+$+1)

Example 43

Synthesis of Compound 43: 1-(2-Chlorophenyl)ethyl N-[5-(2-fluorophenyl)-3-methyl-4-isoxazolyl]carbamate

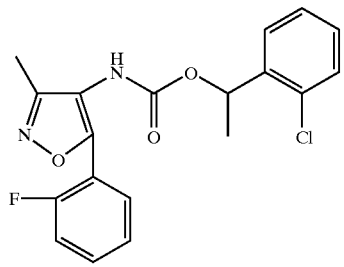

The title compound 43 was obtained in the same manner as used in Example 27.

$^1$H-NMR (CDCl$_3$, 400 MHz): δ7.65–7.72 (1H, m), 7.15–7.50 (7H, m), 6.12–6.25 (2H, m), 2.29 (3H, s), 1.50–1.60 (3H, m) Mass spectrometry (ESI-MS): 375 (M$^+$+1)

Example 44

Synthesis of Compound 44: (1R)-1-(2-Bromophenyl)ethyl N-[3-methyl-5-[4-(trifluoromethoxy)phenyl]-4-isoxazolyl]carbamate

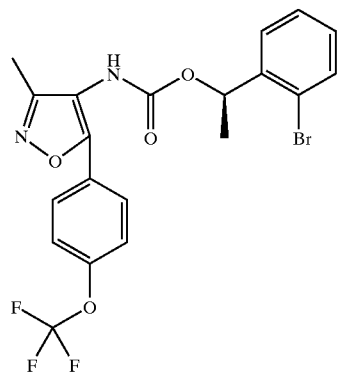

The title compound 44 was obtained in the same manner as used in Example 27.

$^1$H-NMR (CDCl$_3$, 400 MHz): δ7.72 (2H, bs), 6.90–7.55 (6H, m), 6.10 (1H, q, J=6.6 Hz), 5.91 (1H, bs), 2.19 (3H, s), 1.40–1.60 (3H, m) Mass spectrometry (ESI-MS): 485 (M$^+$+1)

Example 45

Synthesis of Compound 45: 1-(2-Fluorophenyl)ethyl N-[3-methyl-5-[4-(trifluoromethoxy)phenyl]-4-isoxazolyl]carbamate

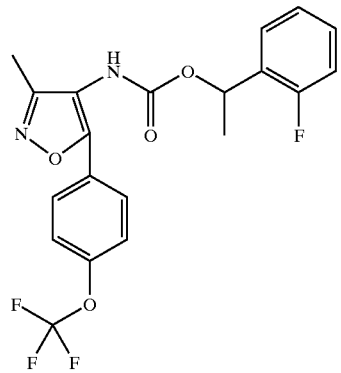

The title compound 45 was obtained in the same manner as used in Example 27.

$^1$H-NMR (CDCl$_3$, 400 MHz): δ7.65–7.80 (2H, m), 6.90–7.45 (6H, m), 6.06 (1H, q, J=6.7 Hz), 5.89 (1H, bs), 2.18 (3H, s), 1.43–1.65 (3H, m) Mass spectrometry (ESI-MS): 425 (M$^+$+1)

Example 46

Synthesis of Compound 46: 1-Phenylethyl N-[5-(4-cyanophenyl)-3-methyl-4-isoxazolyl]carbamate

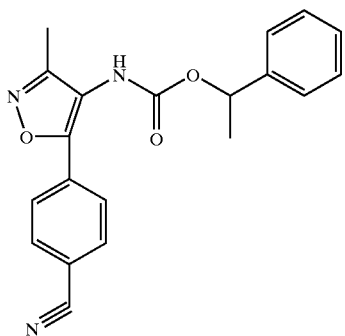

The title compound 46 was obtained in the same manner as used in Example 27.

$^1$H-NMR (CDCl$_3$, 400 MHz): δ7.75–7.85 (2H, m), 7.63–7.68 (3H, m), 7.25–7.50 (4H, m), 5.99 (1H, bs), 5.86 (1H, q, J=6.6 Hz), 2.24 (3H, s), 1.50–1.67 (3H, m) Mass spectrometry (ESI-MS): 348 (M$^+$+1)

Example 47

Synthesis of Compound 47: 1-(2-Chlorophenyl)ethyl N-[5-(4-cyanophenyl)-3-methyl-4-isoxazolyl]carbamate

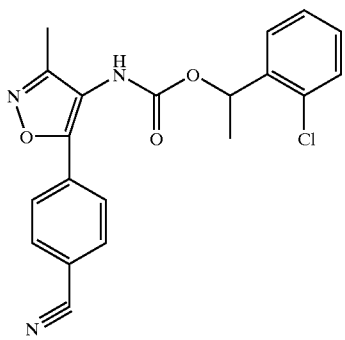

The title compound 47 was obtained in the same manner as used in Example 27.

$^1$H-NMR (CDCl$_3$, 400 MHz): δ7.20–7.95 (8H, m), 6.22 (1H, q, J=6.6 Hz), 6.02 (1H, bs), 2.27 (3H, s), 1.50–1.70 (3H, m) Mass spectrometry (FD-MS): 381 (M$^+$)

Example 48

Synthesis of Compound 48: (1R)-1-(2-Bromophenyl)ethyl N-[3-methyl-5-(4-methylphenyl)-4-isoxazolyl]carbamate

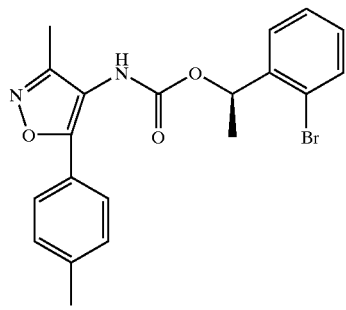

The title compound 48 was obtained in the same manner as used in Example 27.

$^1$H-NMR (CDCl$_3$, 400 MHz): δ6.90–7.76 (8H, m), 6.13 (1H, q, J=6.6 Hz), 6.01 (1H, bs), 2.39 (3H, s), 2.23 (3H, s like), 1.53–1.72 (3H, m) Mass spectrometry (ESI-MS): 415 (M$^+$+1)

Example 49

Synthesis of Compound 49: 1-(2-Fluorophenyl)ethyl N-[3-methyl-5-(4-methylphenyl)-4-isoxazolyl]carbamate

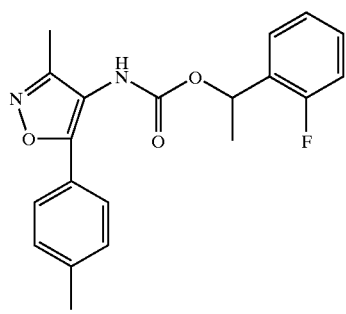

The title compound 49 was obtained in the same manner as used in Example 27.

$^1$H-NMR (CDCl$_3$, 400 MHz): δ6.90–7.75 (8H, m), 6.15 (1H, q, J=6.4 Hz), 6.02 (1H, bs), 2.39 (3H, s), 2.24 (3H, s), 1.50–1.70 (3H, m) Mass spectrometry (ESI-MS): 355 (M$^+$+1)

Example 50

Synthesis of Compound 50: 1-(2-Chlorophenyl)ethyl N-[5-(4-methoxyphenyl)-3-methyl-4-isoxazolyl]carbamate

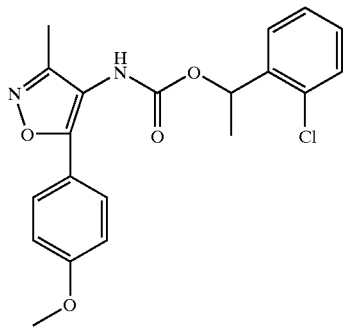

The title compound 50 was obtained in the same manner as used in Example 27.

$^1$H-NMR (CDCl$_3$, 400 MHz): δ7.68 (2H, bs), 7.20–7.55 (4H, m), 6.92 (2H, d, J=9.0 Hz), 5.95 (1H, bs), 3.83 (3H, s), 2.21 (3H, s), 1.35–1.65 (3H, m) Mass spectrometry (ESI-MS): 387, 389 (M$^+$+1)

Example 51

Synthesis of Compound 51: 1-(2-Chlorophenyl)ethyl N-[5-(2-bromophenyl)-3-methyl-4-isoxazolyl]carbamate

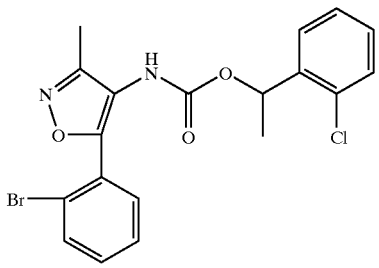

The title compound 51 was obtained in the same manner as used in Example 27.

$^1$H-NMR (CDCl$_3$, 400 MHz): δ7.65–7.70 (1H, m), 7.16–7.50 (7H, m), 6.12 (1H, q, J=6.5 Hz), 6.00–6.25 (1H, m), 2.28 (3H, s), 1.52 (3H, bs) Mass spectrometry (ESI-MS): 435, 437 (M$^+$+1)

Example 52

Synthesis Of Compound 52: 1-(2-Chlorophenyl)ethyl N-[5-(1,3-benzodioxol-5-yl)-3-methyl-4-isoxazolyl]carbamate

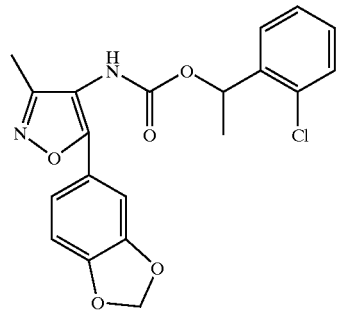

The title compound 52 was obtained in the same manner as used in Example 27.

$^1$H-NMR (CDCl$_3$, 400 MHz): δ6.90–7.60 (5H, m), 6.84 (1H, d, J=8.3 Hz), 6.20 (1H, q, J=6.5 Hz), 5.98–6.08 (3H, m), 2.22 (3H, s), 1.35–1.70 (3H, m) Mass spectrometry (ESI-MS): 401 (M$^+$+1)

Example 53

Synthesis of Compound 53: 1-(2-Chlorophenyl)ethyl N-[3-methyl-5-[3-(trifluoromethoxy)phenyl]-4-isoxazolyl]carbamate

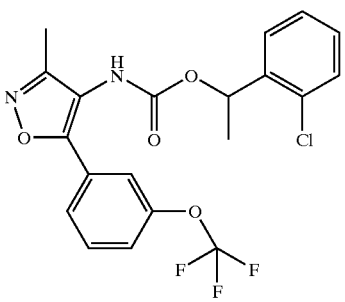

The title compound 53 was obtained in the same manner as used in Example 27.

$^1$H-NMR (CDCl$_3$, 400 MHz): δ7.55–7.68 (2H, m), 7.18–7.50 (6H, m), 6.16 (1H, q, J=6.5 Hz), 5.92 (1H, bs), 2.19 (3H, s), 1.40–1.60 (3H, m) Mass spectrometry (ESI-MS): 441 (M$^+$+1)

Example 54

Synthesis of Compound 54: 1-Phenylethyl N-[3-methyl-5-(4-nitrophenyl)-4-isoxazolyl]carbamate

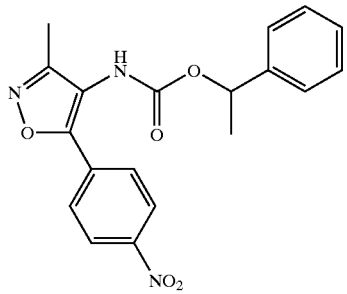

The title compound 54 was obtained in the same manner as used in Example 27.

$^1$H-NMR (CDCl$_3$, 400 MHz): δ8.13–8.18 (2H, m), 7.75–7.85 (2H, m), 7.00–8.00 (5H, m), 5.92 (1H, bs), 5.80 (1H, q, J=6.6 Hz), 2.19 (3H, s), 1.40–1.65 (3H, m) Mass spectrometry (ESI-MS): 368 (M$^+$+1)

Example 55

Synthesis of Compound 55: 1-(2-Chlorophenyl)ethyl N-[3-methyl-5-(4-nitrophenyl)-4-isoxazolyl]carbamate

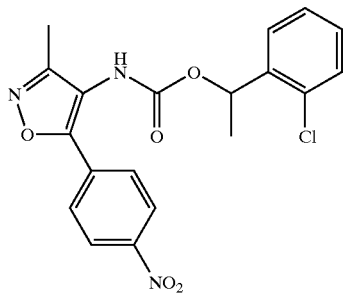

The title compound 55 was obtained in the same manner as used in Example 27.

$^1$H-NMR (CDCl$_3$, 400 MHz): δ8.18–8.23 (2H, m), 7.80–7.90 (2H, m), 7.15–7.50 (4H, m), 6.16 (1H, q, J=6.6 Hz), 2.22 (3H, s), 1.40–1.62 (3H, m) Mass spectrometry (ESI-MS): 402 (M$^+$+1)

Example 56

Synthesis of Compound 56: 1-Phenylethyl N-[3-methyl-5-(2-thienyl)-4-isoxazolyl]carbamate

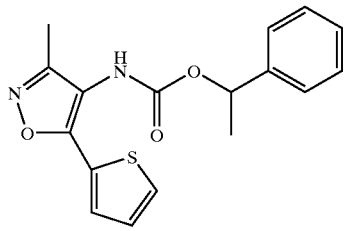

The title compound 56 was obtained in the same manner as used in Example 27.

$^1$H-NMR (CDCl$_3$, 400 MHz): δ7.08–7.60 (8H, m), 5.65–6.00 (2H, m), 2.22 (3H, s), 1.52–1.70 (3H, m) Mass spectrometry (ESI-MS): 329 (M$^+$+1)

Example 57

Synthesis of Compound 57: 1-(2-Chlorophenyl)ethyl N-[3-methyl-5-(2-thienyl)-4-isoxazolyl]carbamate

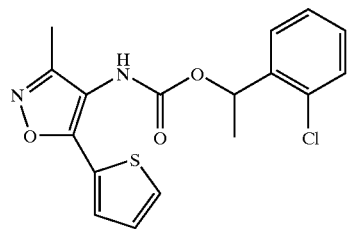

The title compound 57 was obtained in the same manner as used in Example 27.

$^1$H-NMR (CDCl$_3$, 400 MHz): δ7.00–7.65 (7H, m), 6.22 (1H, q, J=6.6 Hz), 5.98 (1H, bs), 2.25 (3H, s), 1.50–1.70 (3H, m) Mass spectrometry (ESI-MS): 363 (M$^+$+1)

Example 58

Synthesis of Compound 58: 1-Phenylethyl N-[3-methyl-5-(3-nitrophenyl)-4-isoxazolyl]carbamate

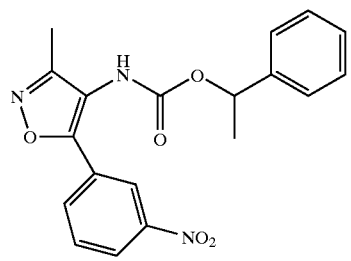

The title compound 58 was obtained in the same manner as used in Example 27.

$^1$H-NMR (CDCl$_3$, 400 MHz): δ8.59–8.62 (1H, m), 8.20–8.27 (1H, m), 8.00–8.05 (1H, m), 7.58 (1H, dd, J=8.1 Hz), 7.20–7.40 (5H, m), 6.00 (1H, bs), 5.85 (1H, q, J=6.6 Hz), 2.24 (3H, s), 1.45–1.70 (3H, m) Mass spectrometry (ESI-MS): 368 (M$^+$+1)

Example 59

Synthesis of Compound 59: 1-(2-Chlorophenyl) ethyl N-[3-methyl-5-(3-nitrophenyl)-4-isoxazolyl] carbamate

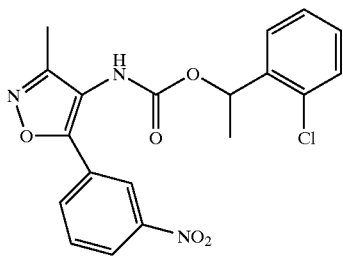

The title compound 59 was obtained in the same manner as used in Example 27.

$^1$H-NMR (CDCl$_3$, 400 MHz): δ8.58 (1H, dd, J=2.0 Hz), 8.18–8.23 (1H, m), 8.00–8.05 (1H, m), 7.56 (1H, dd, J=8.0 Hz), 7.15–7.35 (4H, m), 6.16 (1H, q, J=6.6 Hz), 2.22 (3H, s), 1.30–1.67 (3H, m) Mass spectrometry (ESI-MS): 402 (M$^+$+1)

Example 60

Synthesis of Compound 60: 1-(2-Chlorophenyl) ethyl N-[5-(2,4-difluorophenyl)-3-methyl-4-isoxazolyl]carbamate

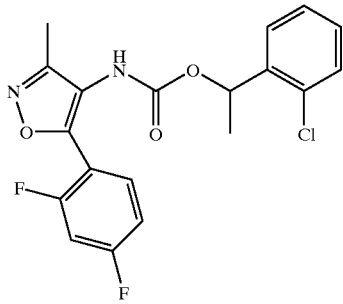

The title compound 60 was obtained in the same manner as used in Example 27.

$^1$H-NMR (CDCl$_3$, 400 MHz): δ7.61–7.69 (1H, m), 7.20–7.50 (4H, m), 6.86–7.03 (2H, m), 6.14 (1H, q, J=6.6 Hz), 6.05–6.20 (1H, m), 2.26 (3H, s), 1.45–1.65 (3H, m) Mass spectrometry (ESI-MS): 393 (M$^+$+1)

Example 61

Synthesis of Compound 61: 1-Phenylethyl N-[3-methyl-5-(4-pyridyl)-4-isoxazolyl]carbamate

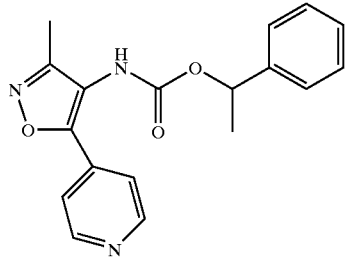

The title compound 61 was obtained in the same manner as used in Example 27.

$^1$H-NMR (CDCl$_3$, 400 MHz): δ8.66 (2H, d, J=5.2 Hz), 7.57 (2H, bs), 7.25–7.50 (5H, m), 6.05 (1H, bs), 5.87 (1H, q, J=6.5 Hz), 2, 25 (3H, s), 1.50–1.70 (3H, m) Mass spectrometry (ESI-MS): 324 (M$^+$+1)

Example 62

Synthesis of Compound 62: 1-(2-Chlorophenyl) ethyl N-[3-methyl-5-(4-pyridyl)-4-isoxazolyl] carbamate

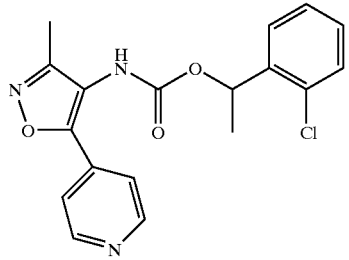

The title compound 62 was obtained in the same manner as used in Example 27.

$^1$H-NMR (CDCl$_3$, 400 MHz): δ8.69 (2H, d, J=5.6 Hz), 7.25–7.70 (6H, m), 6.23 (1H, q, J=6.5 Hz), 6.14 (1H, bs), 2.28 (3H, s), 1.55–1.70 (3H, m) Mass spectrometry (ESI-MS): 358, 360 (M$^+$+1)

Example 63

Synthesis of Compound 63: 1-(2-Chlorophenyl) ethyl N-[5-(6-chloro-3-pyridyl)-3-methyl-4-isoxazolyl]carbamate

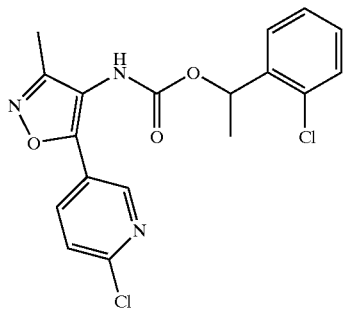

The title compound 63 was obtained in the same manner as used in Example 27.

$^1$H-NMR (CDCl$_3$, 400 MHz): δ8.79 (1H, s), 7.92–8.00 (1H, m), 7.25–7.50 (5H, m), 6.19 (1H, q, J=6.5 Hz), 5.99 (1H, bs), 2.25 (3H, s), 1.45–1.65 (3H, m) Mass spectrometry (ESI-MS): 392, 394 (M$^+$+1)

Example 64

Synthesis of Compound 64: 1-Phenylethyl N-[5-(4-butylphenyl)-3-methyl-4-isoxazolyl]carbamate

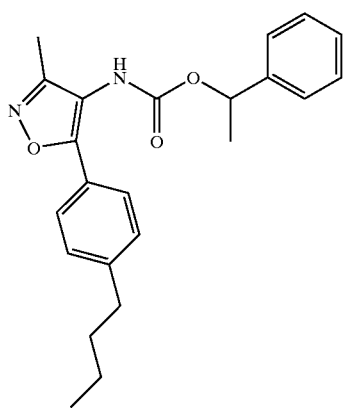

The title compound 64 was obtained in the same manner as used in Example 27.

$^1$H-NMR (CDCl$_3$, 400 MHz): δ7.18–7.70 (9H, m), 5.65–6.00 (2H, m), 2.62 (2H, t, J=7.7 Hz), 2.19 (3H, s), 1.29–1.70 (7H, m), 0.92 (3H, t, J=7.3 Hz) Mass spectrometry (ESI-MS): 379 (M$^+$+1)

Example 65

Synthesis of Compound 65: 1-(2-Chlorophenyl) ethyl N-[5-(4-butylphenyl)-3-methyl-4-isoxazolyl] carbamate

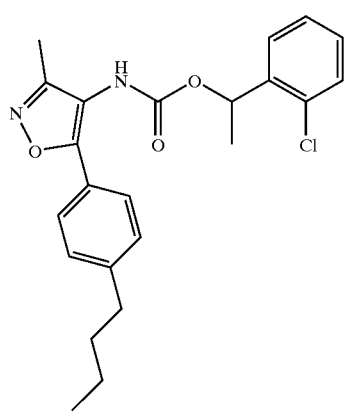

The title compound 65 was obtained in the same manner as used in Example 27.

$^1$H-NMR (CDCl$_3$, 400 MHz): δ6.90–7.70 (8H, m), 6.15 (1H, q, J=6.4 Hz), 5.91 (1H, bs), 2.58 (2H, t, J=7.7 Hz), 2.18 (3H, s), 1.20–1.60 (7H, m), 0.87 (3H, t, J=7.3 Hz) Mass spectrometry (ESI-MS): 413, 415 (M$^+$+1)

Example 66

Synthesis of Compound 66: 1-Phenylethyl N-[3-methyl-5-(3-methyl-2-thienyl)-4-isoxazolyl] carbamate

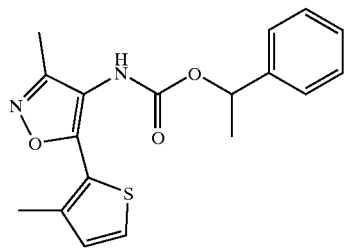

The title compound 66 was obtained in the same manner as used in Example 27.

$^1$H-NMR (CDCl$_3$, 400 MHz): δ7.25–7.50 (6H, m), 6.72–6.78 (1H, m), 5.80–5.95 (1H, m), 2.50 (3H, s like), 2.20 (3H, s), 1.5–1.68 (3H, m) Mass spectrometry (ESI-MS): 343 (M$^+$+1)

Example 67

Synthesis of Compound 67: 1-(2-Chlorophenyl) ethyl N-[3-methyl-5-(3-methyl-2-thienyl)-4-isoxazolyl]carbamate

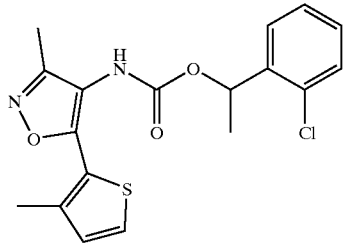

The title compound 67 was obtained in the same manner as used in Example 27.

$^1$H-NMR (CDCl$_3$, 400 MHz): δ7.00–7.65 (5H, m), 6.75–6.80 (1H, m), 6.22 (1H, q, J=6.5 Hz), 5.94 (1H, bs), 2.58 (3H, s like), 2.23 (3H, s), 1.55–1.65 (3H, m) Mass spectrometry (ESI-MS): 377, 379 (M$^+$+1)

Example 68

Synthesis of Compound 68: 1-(2-Chlorophenyl) ethyl N-[5-(3-furyl)-3-methyl-4-isoxazolyl] carbamate

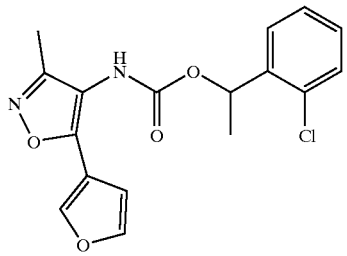

The title compound 68 was obtained in the same manner as used in Example 27.

$^1$H-NMR (CDCl$_3$, 400 MHz): δ7.76 (1H, bs), 7.10–7.50 (5H, m), 6.66 (1H, bs), 6.15 (1H, q, J=6.6 Hz), 5.86 (1H, bs), 2.16 (3H, s), 1.54 (3H, bs) Mass spectrometry (ESI-MS): 347 (M$^+$+1)

Example 69

Synthesis of Compound 69: 1-(2-Chlorophenyl) ethyl N-[3-methyl-5-(5-methyl-2-thienyl)-4-isoxazolyl]carbamate

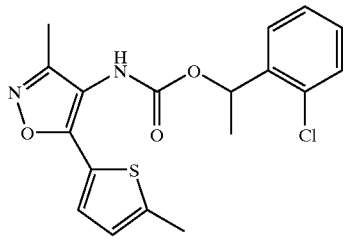

The title compound 69 was obtained in the same manner as used in Example 27.

$^1$H-NMR (CDCl$_3$, 400 MHz): δ7.20–7.55 (5H, m), 6.93 (1H, d, J=5.1 Hz), 6.21 (1H, q, J=6.5 Hz), 5.95 (1H, s), 2.49 (3H, s), 2.25 (3H, s), 1.50–1.60 (3H, m) Mass spectrometry (ESI-MS): 377 (M$^+$+1)

Example 70

Synthesis of Compound 70: 1-(2-Chlorophenyl) ethyl N-[5-[3-(chloromethyl)phenyl]-3-methyl-4-isoxazolyl]carbamate

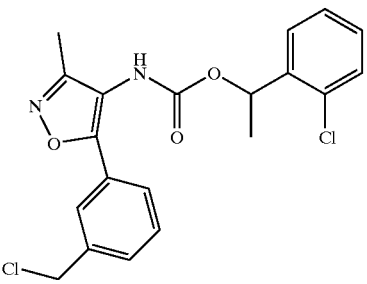

The title compound 70 was obtained in the same manner as used in Example 27.

$^1$H-NMR (CDCl$_3$, 400 MHz): δ7.20–7.85 (8H, m), 6.23 (1H, q, J=6.8 Hz), 6.04 (1H, bs), 4.58 (2H, s), 2.26 (3H, s), 1.50–1.70 (3H, m) Mass spectrometry (ESI-MS): 405, 407 (M$^+$+1)

Example 71

Synthesis of Compound 71: 1-(2-Chlorophenyl) ethyl N-[5-(2-chloro-4-pyridyl)-3-methyl-4-isoxazolyl]carbamate

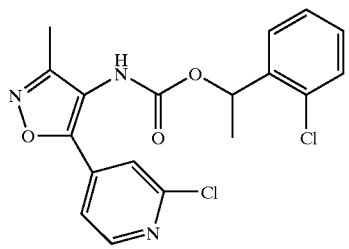

The title compound 71 was obtained in the same manner as used in Example 27.

$^1$H-NMR (CDCl$_3$, 400 MHz): δ8.39 (1H, d, J=5.4 Hz), 7.20–7.55 (5H, m), 7.62 (1H, s), 6.16 (1H, q, J=6.6 Hz), 6.00 (1H, bs), 2.21 (3H, s), 1.35–1.65 (3H, m) Mass spectrometry (ESI-MS): 392, 394 (M$^+$+1)

Example 72

Synthesis of Compound 72: 1-(2-Chlorophenyl)ethyl N-[5-(3-phenyl-5-methyl-4-isoxazolyl)-3-methyl-4-isoxazolyl]carbamate

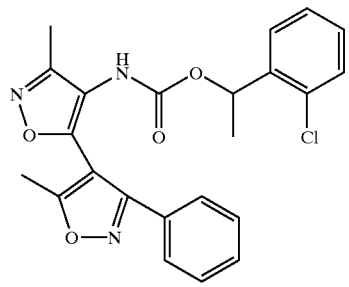

The title compound 72 was obtained in the same manner as used in Example 27.

$^1$H-NMR (CDCl$_3$, 400 MHz): δ7.10–7.50 (9H, m), 5.85–5.95 (1H, m), 5.17 (1H, bs), 2.44 (3H, s), 2.16 (3H, s), 1.36 (3H, d, J=6.3 Hz) Mass spectrometry (ESI-MS): 438, 439 (M$^+$+1)

Example 73

Synthesis of Compound 73: 1-(2-Chlorophenyl)ethyl N-[5-(5-bromo-2-furyl)-3-methyl-4-isoxazolyl]carbamate

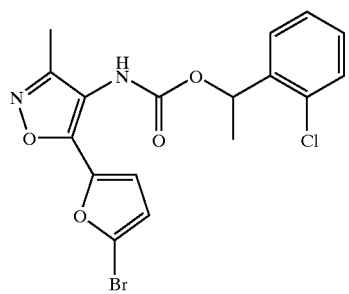

The title compound 73 was obtained in the same manner as used in Example 27.

$^1$H-NMR (CDCl$_3$, 400 MHz): δ7.20–7.55 (4H, m), 6.75–6.80 (1H, m), 6.43 (1H, d, J=3.6 Hz), 6.20 (1H, q, J=6.5 Hz), 2.24 (3H, s), 1.45–1.70 (3H, m) Mass spectrometry (ESI-MS): 427 (M$^+$+1)

Example 74

Synthesis of Compound 74: 1-(2-Chlorophenyl)ethyl N-[5-[4-(chloromethyl)phenyl]-3-methyl-4-isoxazolyl]carbamate

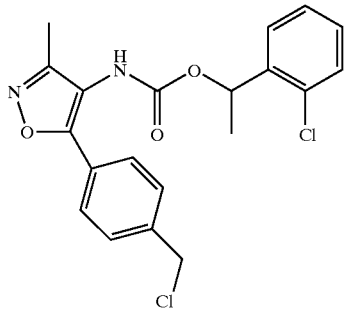

The title compound 74 was obtained in the same manner as used in Example 27.

$^1$H-NMR (CDCl$_3$, 400 MHz): δ7.69 (2H, bs), 6.75–7.50 (6H, m), 6.15 (1H, q, J=6.4 Hz), 5.95 (1H, bs), 4.53 (2H, s), 2.18 (3H, s), 1.45–1.62 (3H, m) Mass spectrometry (ESI-MS): 405 (M$^+$+1)

Example 75

Synthesis of Compound 75: 1-(2-Chlorophenyl)ethyl N-[3-methyl-5-(3-thienyl)-4-isoxazolyl]carbamate

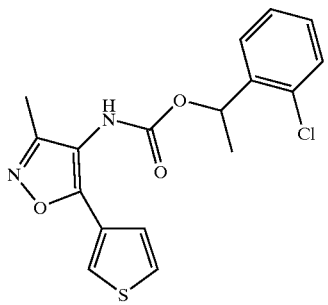

The title compound 75 was obtained in the same manner as used in Example 27.

$^1$H-NMR (CDCl$_3$, 400 MHz): δ7.75 (1H, bs), 7.00–7.60 (6H, m), 6.22 (1H, q, J=6.4 Hz), 5.98 (1H, bs), 2.24 (3H, s), 1.50–1.70 (3H, m) Mass spectrometry (ESI-MS): 361 (M$^+$+1)

Example 76

Synthesis of Compound 76: 1-(2-Chlorophenyl) ethyl N-(3-ethyl-5-phenyl-4-isoxazolyl)carbamate

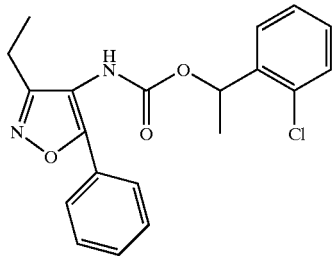

The title compound 76 was obtained in the same manner as used in Example 27.

$^1$H-NMR (CDCl$_3$, 400 MHz): δ6.75–7.85 (9H, m), 6.12–6.25 (1H, m), 5.97 (1H, bs), 2.64 (2H, m), 1.52–1.65 (2H, m), 1.28 (3H, t, J=7.6 Hz) Mass spectrometry (ESI-MS): 371 (M$^+$+1)

Example 77

Synthesis of Compound 77: 1-(2-Chlorophenyl) ethyl N-[5-(4-cyanophenyl)-3-ethyl-4-isoxazolyl]carbamate

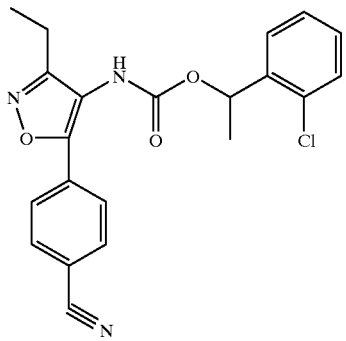

The title compound 77 was obtained in the same manner as used in Example 27.

$^1$H-NMR (CDCl$_3$, 400 MHz): δ7.85 (2H, bs), 7.69 (H, d, J=8.3 Hz), 7.25–7.55 (4H, m), 6.21 (1H, q, J=6.6 Hz), 6.01 (1H, bs), 2.67 (2H, q, J=7.6 Hz), 1.31 (3H, t, J=7.6 Hz) Mass spectrometry (ESI-MS): 394, 396 (M$^+$−1)

Example 78

Synthesis of Compound 78: 1-(2-Chlorophenyl) ethyl N-[3-(methoxymethyl)-5-phenyl-4-isoxazolyl] carbamate

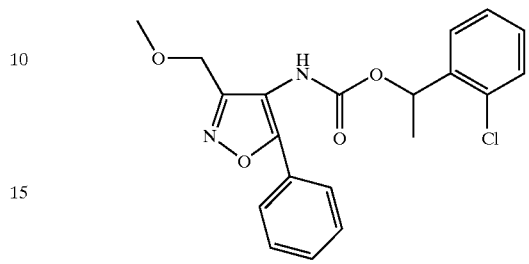

The title compound 78 was obtained in the same manner as used in Example 27.

$^1$H-NMR (CDCl$_3$, 400 MHz): δ7.20–7.78 (9H, m), 6.05–6.19 (1H, m), 4.43–4.60 (2H, m), 3.31 (3H, s), 1.40–1.50 (3H, m) Mass spectrometry (ESI-MS): 387, 389 (M$^+$+1)

Example 79

Synthesis of Compound 79: 1-(2-Chlorophenyl) ethyl N-[3-methyl-5-[4-(phenoxymethyl)phenyl]-4-isoxazolyl]carbamate

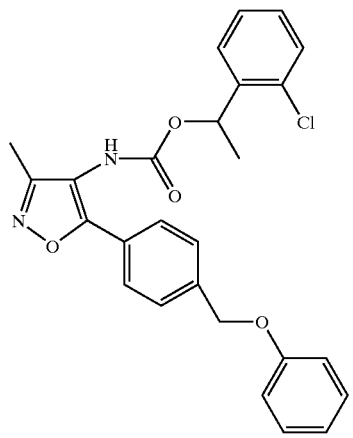

The title compound 79 was obtained in the same manner as used in Example 27.

$^1$H-NMR (CDCl$_3$, 400 MHz): δ7.76 (2H, bs), 7.43–7.55 (3H, m), 7.25–7.43 (6H, m), 6.95–7.02 (2H, m), 6.22 (1H, q, J=6.6 Hz), 6.00 (1H, bs), 5.11 (1H, s), 4.60 (1H, s), 2.56 (3H, s), 1.50–1.70 (3H, m) Mass spectrometry (ESI-MS): 463 (M$^+$+1)

Example 80

Synthesis of Compound 80: 2,2,2-Trifluoro-1-phenylethyl N-(5-methyl-3-phenyl-4-isoxazolyl)carbamate

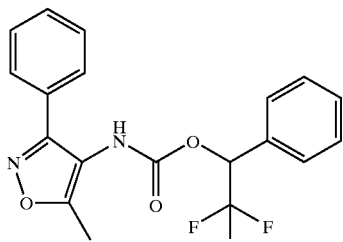

The title compound 80 was obtained in the same manner as used in Example 1.

$^1$H-NMR (CDCl$_3$, 400 MHz): δ7.18–7.60 (10H, m), 6.00–6.15 (2H, m), 2.33 (3H, s) Mass spectrometry (ESI-MS): 375 (M$^+$+1)

Example 81

Synthesis of Compound 81: 1-Phenylallyl N-(5-methyl-3-phenyl-4-isoxazolyl)carbamate

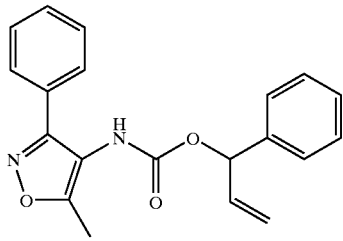

The title compound 81 was obtained in the same manner as used in Example 1.

$^1$H-NMR (CDCl$_3$, 400 MHz): δ7.00–7.75 (10H, m), 5.00–6.30 (4H, m), 2.37 (3H, s) Mass spectrometry (ESI-MS): 335 (M$^+$+1)

Example 82

Synthesis of Compound 82: 1-(2-Chlorophenyl)ethyl N-[5-(4-[[(4-fluorobenzyl)oxy]methyl]phenyl)-3-methyl-4-isoxazolyl]carbamate

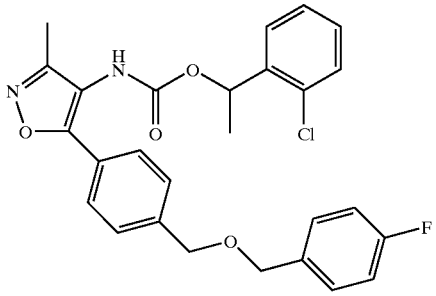

The title compound 82 was obtained in the same manner as used in Example 27.

$^1$H-NMR (CDCl$_3$, 400 MHz): δ6.90–7.80 (12H, m), 6.15–6.25 (1H, m), 5.98 (1H, bs), 4.50–4.58 (4H, m), 2.13–2.17 (3H, s), 1.20–1.70 (3H, m) Mass spectrometry (ESI-MS): 495 (M$^+$+1)

Example 83

Synthesis of Compound 83: 1-(2-Chlorophenyl)ethyl N-[5-(4-[[(2,6-difluorobenzyl)oxy]methyl]phenyl)-3-methyl-4-isoxazolyl]carbamate

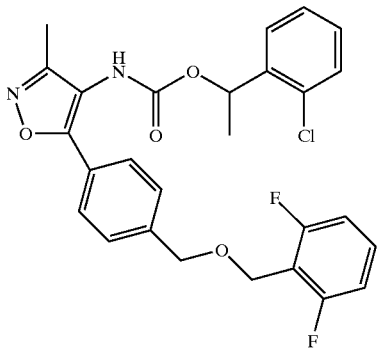

The title compound 83 was obtained in the same manner as used in Example 27.

$^1$H-NMR (CDCl$_3$, 400 MHz): δ6.85–7.80 (11H, m), 6.19 (1H, q, J=6.6 Hz), 4.65 (2H, s), 4.59 (2H, s), 2.23 (3H, s), 1.47–1.65 (3H, m) Mass spectrometry (ESI-MS): 513 (M$^+$+1)

Example 84

Synthesis of Compound 84: 1-(2-Chlorophenyl)ethyl N-(5-[4-[(2-furylmethoxy)methyl]phenyl]-3-methyl-4-isoxazolyl)carbamate

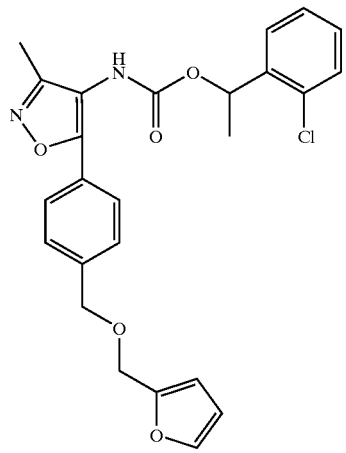

The title compound 84 was obtained in the same manner as used in Example 27.

$^1$H-NMR (CDCl$_3$, 400 MHz): δ6.80–7.80 (9H, m), 6.31–6.36 (2H, m), 6.20 (1H, q, J=6.5 Hz), 5.98 (1H, bs), 4.56 (2H, s), 4.50 (2H, s), 2.23 (3H, s), 1.48–1.65 (3H, m) Mass spectrometry (ESI-MS): 467 (M$^+$+1)

Example 85

Synthesis of Compound 85: 1-(2-Chlorophenyl)ethyl N-(5-[4-[(3-furylmethoxy)methyl]phenyl]-3-methyl-4-isoxazolyl)carbamate

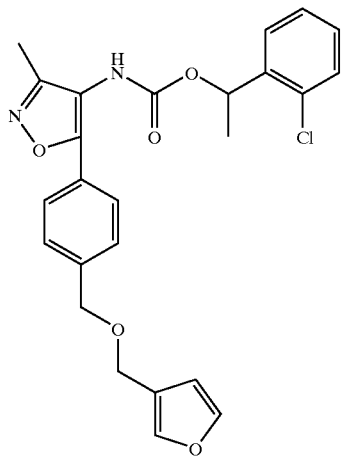

The title compound 85 was obtained in the same manner as used in Example 27.

$^1$H-NMR (CDCl$_3$, 400 MHz): δ6.80–7.80 (10H, m), 6.43 (1H, s), 6.20 (1H, q, J=6.5 Hz), 4.54 (3H, s), 4.43 (3H, s), 2.23 (3H, s), 1.45–1.70 (3H, m) Mass spectrometry (ESI-MS): 467 (M$^+$+1)

Example 86

Synthesis of Compound 86: 2,2,2-Trifluoro-1-phenylethyl N-[5-(4-cyanophenyl)-3-methyl-4-isoxazolyl]carbamate

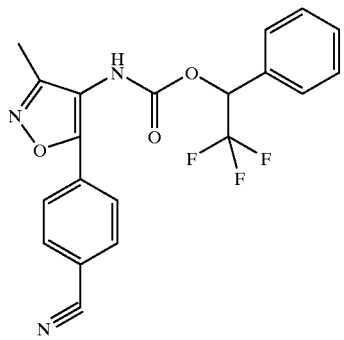

The title compound 86 was obtained in the same manner as used in Example 27.

$^1$H-NMR (CDCl$_3$, 400 MHz): δ7.00–7.80 (9H, m), 6.22 (1H, bs), 6.06 (1H, q, J=6.7 Hz), 2.20 (3H, s) Mass spectrometry (ESI-MS): 402 (M$^+$+1)

Example 87

Synthesis of Compound 87: 1-(2-Chlorophenyl)ethyl N-[5-[4-(methoxymethyl)phenyl]-3-methyl-4-isoxazolyl]carbamate

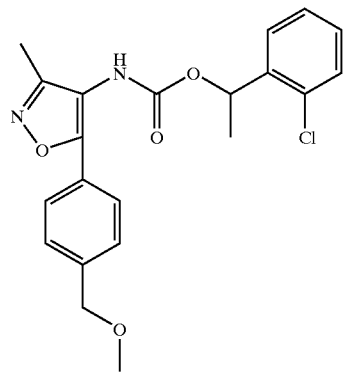

The title compound 87 was obtained in the same manner as used in Example 27.

$^1$H-NMR (CDCl$_3$, 400 MHz): δ6.80–7.75 (8H, m), 6.15 (1H, q, J=6.5 Hz), 5.93 (1H, bs), 4.43 (2H, s), 3.35 (3H, s), 2.18 (3H, s), 1.30–1.60 (3H, m) Mass spectrometry (ESI-MS): 401 (M$^+$+1)

Example 88

Synthesis of Compound 88: 1-(2-Chlorophenyl)ethyl N-[3-methyl-5-[4-(morpholinomethyl)phenyl]-4-isoxazolyl]carbamate

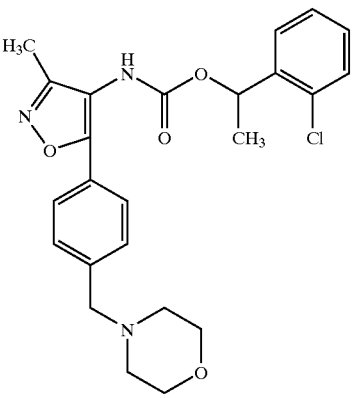

The title compound 88 was obtained in the same manner as used in Example 27.

$^1$H-NMR (CDCl$_3$, 400 MHz): δ6.98–7.80 (8H, m), 6.00–6.25 (2H, m), 3.71 (4H, t, J=4.4 Hz), 3.52 (2H, s), 2.41–2.47 (2H, m), 2.24 (3H, s), 1.35–1.70 (3H, m) Mass spectrometry (ESI-MS): 454 (M$^+$+1)

Example 89

Synthesis of Compound 89: 1-(2-Chlorophenyl)ethyl N-(5-[4-[(2,6-dimethylmorpholino)methyl]phenyl]-3-methyl-4-isoxazolyl)carbamate

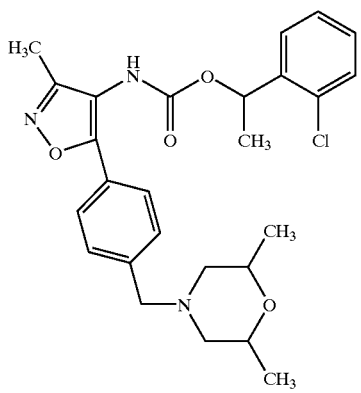

The title compound 89 was obtained in the same manner as used in Example 27.

$^1$H-NMR (CDCl$_3$, 400 MHz): δ6.95–7.80 (8H, m), 5.95–6.25 (2H, m), 3.64–3.74 (2H, m), 3.49 (2H, s), 2.64–2.72 (2H, m), 2.24 (3H, s), 1.55–1.82 (5H, m), 1.13 (6H, d, J=6.4 Hz) Mass spectrometry (ESI-MS): 484 (M$^+$+1)

Example 90

Synthesis of Compound 90: 1-(2-Chlorophenyl)ethyl N-(3-methyl-5-[4-[([2-(2-pyridyl)ethyl]amino)methyl]phenyl]-4-isoxazolyl)carbamate

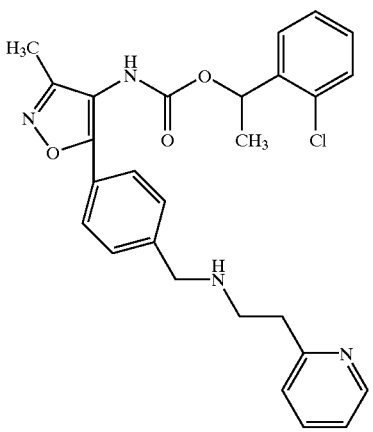

The title compound 90 was obtained in the same manner as used in Example 27.

$^1$H-NMR (CDCl$_3$, 400 MHz): δ8.49–8.55 (1H, m), 6.95–7.80 (11H, m), 6.50 (1H, bs), 6.21 (1H, q, J=6.3 Hz), 3.85 (2H, s), 2.97–3.10 (4H, m), 2.23 (3H, s), 1.62 (3H, bs) Mass spectrometry (ESI-MS): 491, 493 (M$^+$+1)

Example 91

Synthesis of Compound 91: 1-(2-Chlorophenyl)ethyl N-[3-methyl-5-(4-[[(tetrahydro-2-furanylmethyl)amino]methyl]phenyl)-4-isoxazolyl]-carbamate

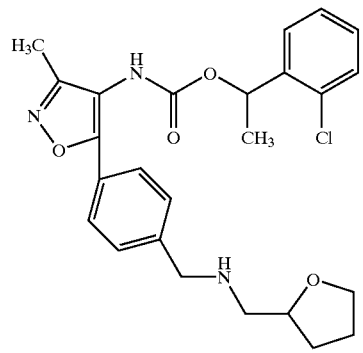

The title compound 91 was obtained in the same manner as used in Example 27.

$^1$H-NMR (CDCl$_3$, 400 MHz): δ6.95–7.80 (8H, m), 6.53 (1H, bs), 6.21 (1H, q, J=6.2 Hz), 3.99–4.07 (1H, m), 3.80–3.87 (3H, m), 3.70–3.78 (1H, m), 2.59–2.73 (2H, m), 2.23 (3H, s), 1.83–2.00 (4H, m), 1.35–1.75 (3H, m) Mass spectrometry (ESI-MS): 470, 472 (M$^+$+1)

Example 92

Synthesis of Compound 92: 1-(2-Chlorophenyl)ethyl N-[3-methyl-5-(4-[[(2-pyridylmethyl)amino]methyl]phenyl)-4-isoxazolyl]carbamate

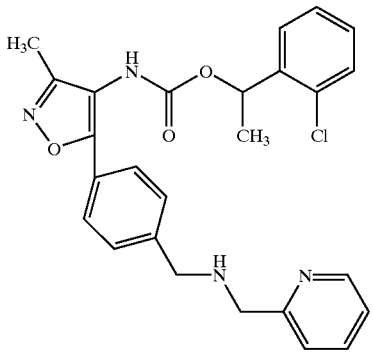

The title compound 92 was obtained in the same manner as used in Example 27.

$^1$H-NMR (CDCl$_3$, 400 MHz): δ8.54–8.58 (1H, m), 6.90–7.75 (11H, m), 6.64 (1H, bs), 6.21 (1H, q, J=6.4 Hz), 3.91 (2H, s), 3.86 (2H, s), 2.22 (3H, s), 1.30–1.70 (3H, m) Mass spectrometry (ESI-MS): 477, 479 (M$^+$+1)

Example 93

Synthesis of Compound 93: 1-(2-Chlorophenyl)ethyl N-[5-(4-[[(2-furylmethyl)amino]methyl]phenyl)-3-methyl-4-isoxazolyl]carbamate

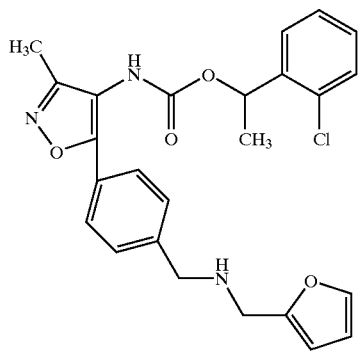

The title compound 93 was obtained in the same manner as used in Example 27.

$^1$H-NMR (CDCl$_3$, 400 MHz): δ6.95–7.80 (8H, m), 5.98–6.35 (4H, m), 3.81 (2H, s), 3.79 (2H, s), 2.24 (3H, s), 1.30–1.75 (3H, m) Mass spectrometry (ESI-MS): 466, 468 (M$^+$+1)

Example 94

Synthesis of Compound 94: 2-Cyclohexyl N-(5-methyl-3-phenyl-4-isoxazolyl)carbamate

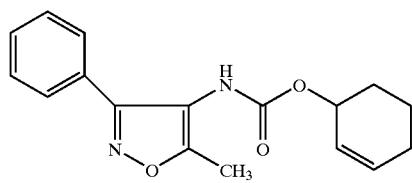

The title compound 94 was obtained in the same manner as used in Example 1.

$^1$H-NMR (CDCl$_3$, 400 MHz): 7.60 (2H, m), 7.36 (3H, m), 2.34 (3H, s), 1.59 (9H, m) Mass spectrometry (FD-MS): 298 (M$^+$)

Example 95

Synthesis of Compound 95: 2-Methylphenethyl N-(5-methyl-3-phenyl-4-isoxazolyl)carbamate

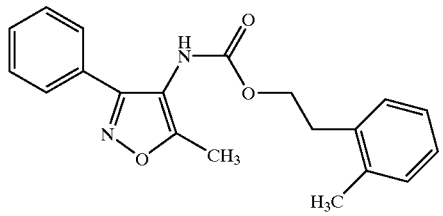

The title compound 95 was obtained in the same manner as used in Example 1.

$^1$H-NMR (CDCl$_3$, 400 MHz): 7.59 (2H, dd, J=4.17 Hz, J=5.61 Hz), 7.38 (2H, dd, J=3.42 Hz, J=5.61 Hz), 7.09 (5H, m), 3.78 (2H, t, J=6.83 Hz), 2.83 (2H, t, J=6.83 Hz), 2.34 (3H, bs), 2.27 (3H, s) Mass spectrometry (FD-MS): 336 (M$^+$)

Example 96

Synthesis of Compound 96: Phenethyl N-(5-methyl-3-phenyl-4-isoxazolyl)carbamate

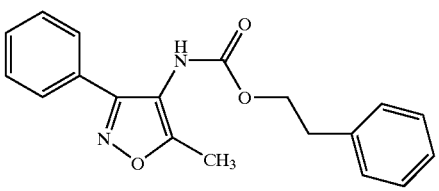

The title compound 96 was obtained in the same manner as used in Example 1.

H-NMR (CDCl$_3$, 400 MHz): 7.37 (2H, m), 7.25 (2H, m), 7.18 (6H, m), 3.80 (2H, t, J=6.59 Hz), 2.81 (2H, t, J=6.59 Hz), 2.32 (3H, s), 2.18 (3H, bs) Mass spectrometry (FD-MS): 322 (M$^+$)

Example 97

Synthesis of Compound 97: 2,3-Dihydro-1H-1-indenyl N-(5-methyl-3-phenyl-4-isoxazolyl)carbamate

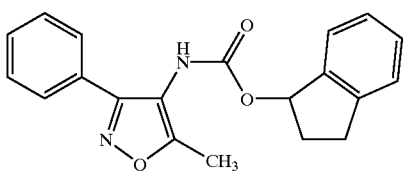

The title compound 97 was obtained in the same manner as used in Example 1.

Mass spectrometry (FD-MS): 334 (M$^+$)

Example 98

Synthesis of Compound 98: 1,2,3,4-Tetrahydro-2-naphthalenyl N-(5-methyl-3-phenyl-4-isoxazolyl)carbamate

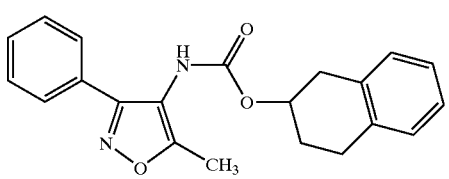

The title compound 98 was obtained in the same manner as used in Example 1.

Mass spectrometry (FD-MS): 348 (M$^+$)

Example 99

Synthesis of Compound 99: Pentyl N-(5-methyl-3-phenyl-4-isoxazolyl)carbamate

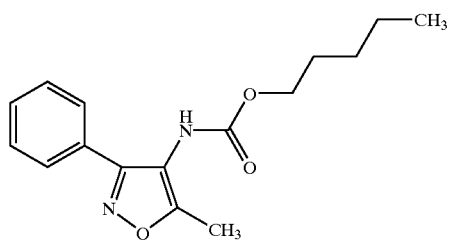

The title compound 99 was obtained in the same manner as used in Example 1.

Mass spectrometry (FD-MS): 288 (M+)

Example 100

Synthesis of Compound 100: Isopentyl N-(5-methyl-3-phenyl-4-isoxazolyl)carbamate

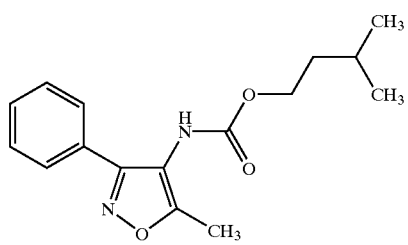

The title compound 100 was obtained in the same manner as used in Example 1.

$^1$H-NMR (CDCl$_3$, 400 MHz): δ7.61 (2H, bs), 7.39 (3H, m), 4.11 (2H, m), 3.36 (3H, s), 1.49 (3H, m), 0.83 (6H, bs) Mass spectrometry (FD-MS): 288 (M+)

Example 101

Synthesis of Compound 101: 1-Methylpentyl N-(5-methyl-3-phenyl-4-isoxazolyl)carbamate

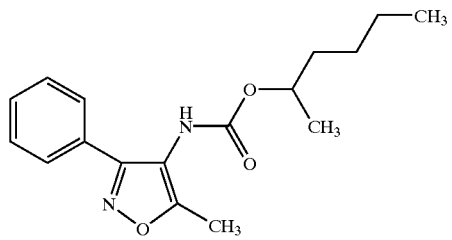

The title compound 101 was obtained in the same manner as used in Example 1.

$^1$H-NMR (CDCl$_3$, 400 MHz): δ7.59 (2H, bs), 7.36 (3H, m), 4.65 (1H, m), 2.33 (3H, s), 1.21 (8H, m), 0.77 (4H, m) Mass spectrometry (FD-MS): 302 (M+)

Example 102

Synthesis of Compound 102: 4-Pentenyl N-(5-methyl-3-phenyl-4-isoxazolyl)carbamate

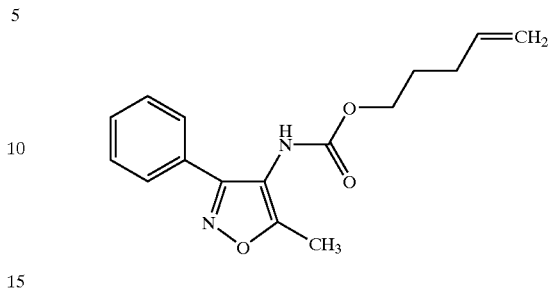

The title compound 102 was obtained in the same manner as used in Example 1.

$^1$H-NMR (CDCl$_3$, 400 MHz): δ7.61 (2H, bs), 7.39 (3H, m), 4.93 (3H, m), 4.09 (2H, m), 2.36 (3H, s), 2.10 (2H, m), 1.73 (2H, m) Mass spectrometry (FD-MS): 286 (M+)

Example 103

Synthesis of Compound 103: 1-(2-Chlorophenyl) ethyl N-[3-methyl-5-[4-([2-(2-pyridyl)ethyl]amino) methyl)phenyl]-4-isoxazolyl)carbamate Methyl 3-oxobutanoate (29.4 g) was dissolved in methanol (30.0 ml), and a 40%-methylamine-methanol solution (32.0 ml) was added dropwise at room temperature. The mixture was stirred for 1 hour. After the completion of the reaction, the reaction solution as such was concentrated, and then dried using a vacuum pump. Thus, methyl 3-(methylamino)-2-butenoate (31.8 g, yield 97%) was obtained. Subsequently, methyl 3-(methylamino)-2-butenoate (5.38 g) was dissolved in tetrahydrofuran (100 ml), and pyridine (5.0 ml) was added dropwise at room temperature. Under ice cooling, p-chloromethyl benzoyl chloride (8.0 g) was added dropwise and the mixture was stirred at room temperature for 4 hours. After the completion of the reaction, distilled water was added, and the product was extracted by liquid separation using ether and then washed with saturated aqueous solution of sodium chloride. The product was dried over sodium sulfate to concentrate and the residue was dried using a vacuum pump. Subsequently, the residue was dissolved in acetic acid (30.0 ml). Hydroxylamine hydrochloride (2.8 g) was added at room temperature, and the mixture was heated under reflux for 1 hour and 30 minutes. After the completion of the reaction, saturated aqueous solution of sodium hydrogencarbonate was added to neutralize the reaction system, and the product was extracted by liquid separation using ether. The resultant organic layer was washed with saturated solution of sodium chloride and dried over sodium sulfate to concentrate. The residue was purified through a column using a hexane-acetone elution system. Thus, methyl 5-[4-(chloromethyl)phenyl]-3-methyl-4-isoxazole carboxylate (5.42 g, yield 49.0%) was obtained.

Methyl 5-[4-(chloromethyl)phenyl]-3-methyl-4-isoxazole carboxylate (5.418 g) was dissolved in tetrahydrofuran/distilled water=2/1 (100.0 ml), lithium hydroxide (1.9 g) was added at room temperature, and the mixture was stirred at that temperature for 7 hours. After the completion of the reaction, a 5%-aqueous hydrochloric acid was added to acidify the system, the product was extracted by liquid separation using chloroform, and washed with saturated aqueous solution of sodium chloride. The product was dried over sodium sulfate to concentrate and the residue was dried using a vacuum pump. Thus, a useful intermediate, i.e., methyl 5-[4-(chloromethyl)phenyl]-3-methyl-4-isoxazole carboxylic acid (4.82 g, yield 94.0%), was obtained.

Methyl 5-[4-(chloromethyl)phenyl]-3-methyl-4-isoxazole carboxylic acid (4.82 g) was dissolved in anhydrous toluene (100.0 ml). Subsequently, diphenylphosphoryl azide (5.0 ml) and triethylamine (2.9 ml) were added at room temperature, and the mixture was stirred at 120° C. for 30 minutes. After the product was allowed to stand at room temperature, 1-(2-chlorophenyl)-1-ethanol (2.9 ml) was added and the mixture was stirred again at 120° C. for 2 hours. After the completion of the reaction, the reaction product was allowed to cool at room temperature, and distilled water was then added thereto, and the product was extracted by liquid separation using chloroform, and then washed with saturated aqueous solution of sodium chloride. The product was dried over sodium sulfate to concentrate and the residue was purified through a column using a hexane-acetone elution system. Thus, 1-(2-chlorophenyl) ethyl N-5-[4-chloromethyl]phenyl]-3-methyl-4-isoxazolylcarbamate (3.81 g, yield 49.0%) was obtained.

Subsequently, the resultant 1-(2-chlorophenyl)ethyl N-5-[4-chloromethyl]phenyl]-3-methyl-4-isoxazolylcarbamate (100 mg) was dissolved in methylene chloride (3.0 ml). Triethylamine (205.0 μl) and 2-(2-pyridyl)-1-ethanolamine (100 μl) were then added at room temperature, and the mixture was stirred at that temperature for 12 hours. After the completion of the reaction, distilled water was added thereto, and the reaction product was extracted by liquid separation using chloroform, and then washed with a saturated saline solution. The product was dried over sodium sulfate to concentrate and the residue was purified by column chromatography on silica gel. Thus, the title compound 103 (77 mg, 63.6%) was obtained.

$^1$H-NMR (CDCl$_3$, 400 MHz): δ8.51 (1H, d, J=4.9 Hz), 7.00–7.69 (11H, m), 6.50 (1H, bs), 6.21 (1H, q, J=6.3 Hz), 3.85 (2H, s), 2.99–3.01 (4H, m), 2.23 (3H, s), 1.40–1.70 (3H, m) Mass spectrometry (ESI-MS): 491 (M$^+$+1)

Examples 104 to 169

The following Compounds 104 to 169 were obtained in the same manner as used in Example 103. The structures of these compounds are shown in FIG. 1.

Compound 104

1-(2-Chlorophenyl)ethyl N-[3-methyl-5-(4-{[(tetrahydro-2-furanylmethyl)amino]-methyl}phenyl)-4-isoxazolyl]carbamate $^1$H-NMR (CDCl$_3$, 400 MHz): δ7.00–7.80 (8H, m), 6.53 (1H, bs), 6.21 (1H, q, J=6.2 Hz), 3.99–4.06 (2H, m), 3.70–3.85 (3H, m), 2.60–2.73 (2H, m), 2.26 (3H, s), 1.50–2.00 (7H, m) Mass spectrometry (ESI-MS): 470, 472 (M$^+$+1)

Compound 105

1-(2-Chlorophenyl)ethyl N-[3-methyl-5-(4-{[(2-pyridylmethyl)amino]methyl}-phenyl)-4-isoxazolyl] carbamate $^1$H-NMR (CDCl$_3$, 400 MHz): δ8.53–8.58 (1H, m), 7.00–7.80 (11H, m), 6.64 (1H, bs), 6.21 (1H, q, J=6.4 Hz), 3.91 (2H, s), 3.86 (2H, s), 2.22 (3H, s), 1.30–1.70 (3H, m) Mass spectrometry (ESI-MS): 477, 479 (M$^+$+1)

Compound 106

1-(2-Chlorophenyl)ethyl N-[5-(4-{[(2-furylmethyl) amino]methyl}phenyl)-3-methyl-4-isoxazolyl] carbamate $^1$H-NMR (CDCl$_3$, 400 MHz): δ7.00–7.80 (9H, m), 6.00–6.34 (4H, m), 3.81 (3H, s), 3.79 (3H, s), 2.24 (3H, s), 1.35–1.75 (3H, m) Mass spectrometry (ESI-MS): 466, 468 (M$^+$+1)

Compound 107

1-(2-Chlorophenyl)ethyl N-[5-(4-{[(2-furylmethyl) sulfanyl]methyl}phenyl)-3-methyl-4-isoxazolyl] carbamate $^1$H-NMR (CDCl$_3$, 400 MHz): δ7.72 (1H, bs), 7.25–7.60 (8H, m), 6.32–6.34 (1H, m), 6.22 (1H, q, J=6.6 Hz), 6.15–6.18 (1H, m), 3.71 (2H, s), 3.59 (2H, s), 2.25 (3H, s), 1.35–1.70 (3H, m) Mass spectrometry (ESI-MS): 483 (M$^+$+1)

Compound 108

1-(2-Chlorophenyl)ethyl N-(5-{4-[(ethylsulfanyl) methyl]phenyl}-3-methyl-4-isoxazolyl)carbamate $^1$H-NMR (CDCl$_3$, 400 MHz): δ7.00–7.73 (8H, m), 6.21 (1H, q, J=6.2 Hz), 6.09 (1H, bs), 3.73 (2H, s), 2.43 (2H, q, J=7.3 Hz), 2.24 (3H, s), 1.30–1.70 (3H, m), 1.24 (3H, t, J=7.3 Hz) Mass spectrometry (ESI-MS): 431 (M$^+$+1)

Compound 109

1-(2-Chlorophenyl)ethyl N-(3-methyl-5-{4-[(pentylamino)methyl]phenyl}-4-isoxazolyl) carbamate $^1$H-NMR (CDCl$_3$, 400 MHz): δ7.00–7.75 (8H, m), 6.46 (1H, bs), 6.21 (1H, q, J=6.4 Hz), 3.81 (2H, s), 2.62 (2H, t, J=7.3 Hz), 2.23 (3H, s), 1.25–1.62 (9H, m), 0.89 (3H, t, J=6.9 Hz) Mass spectrometry (ESI-MS): 456 (M$^+$+1)

Compound 110

1-(2-Chlorophenyl)ethyl N-{3-methyl-5-[4-({[2-(3-pyridyl)ethyl]amino}methyl)-phenyl]-4-isoxazolyl}carbamate $^1$H-NMR (CDCl$_3$, 400 MHz): δ8.42–8.47 (2H, m), 7.70 (2H, bs), 7.00–7.55 (8H, m), 6.50 (1H, bs), 6.19–6.25 (1H, m), 3.83 (2H, s), 2.79–2.92 (4H, m), 2.24 (3H, s), 1.30–1.75 (3H, m) Mass spectrometry (ESI-MS): 491, 493 (M$^+$+1)

Compound 111

1-(2-Chlorophenyl)ethyl N-{3-methyl-5-[4-({[2-(4-pyridyl)ethyl]amino}methyl)phenyl]-4-isoxazolyl}carbamate $^1$H-NMR (CDCl$_3$, 400 MHz): δ8.47–8.49 (2H, m), 7.70 (2H, bs), 7.00–7.55 (8H, m), 6.46 (1H, bs), 6.21 (1H, q, J=6.4 Hz), 3.82 (2H, s), 2.78–2.95 (4H, m), 2.24 (3H, s), 1.30–1.75 (3H, m) Mass spectrometry (ESI-MS): 491, 493 (M$^+$+1)

Compound 112

1-(2-Chlorophenyl)ethyl N-[5-(4-{[(2-fluoroethyl) amino]methyl}phenyl)-3-methyl-4-isoxazolyl] carbamate $^1$H-NMR (CDCl$_3$, 400 MHz): δ7.72 (2H, bs), 7.00–7.50 (6H, m), 6.22 (1H, q, J=6.4 Hz), 6.10 (1H, bs), 4.63 (1H, t, J=4.8 Hz), 4.51 (1H, t, J=4.7 Hz), 3.88 (1H, s), 2.96 (1H, t, J=4.8 Hz), 2.89 (1H, t, J=4.8 Hz), 2.25 (3H, s), 1.30–1.75 (3H, m) Mass spectrometry (ESI-MS): 432, 434 (M$^+$+1)

Compound 113

Ethyl 3-({4-[4-({[1-(2-chlorophenyl)ethoxy]carbonyl}amino)-3-methyl-5-isoxazolyl]-benzyl}amino)propanoate $^1$H-NMR (CDCl$_3$, 400 MHz): δ7.20–7.75 (8H, m), 6.21 (1H, q, J=6.6 Hz), 6.00 (1H, bs), 4.16 (2H, q, J=7.2 Hz), 3.85 (2H, s), 2.89 (2H, t, J=6.4 Hz), 2.54 (2H, t, J=6.4 Hz), 2.25 (3H, s), 1.63 (3H, bs), 1.26 (3H, t, J=7.2 Hz) Mass spectrometry (ESI-MS): 486, 488 (M$^+$+1)

Compound 114

1-(2-Chlorophenyl)ethyl N-{3-methyl-5-[4-({[(5-methyl-2-pyrazyl)methyl]amino}-methyl)phenyl]-4-isoxazoly}carbamate $^1$H-NMR (CDCl$_3$, 400 MHz): δ8.47 (1H, s), 8.41 (1H, s), 7.20–7.72 (8H, m), 6.15–6.25 (1H, m), 6.00 (1H, bs), 3.94 (2H, s), 3.89 (2H, s), 2.56 (3H, s), 2.25 (3H, s), 1.00–1.75 (3H, m) Mass spectrometry (ESI-MS): 492, 494 (M$^+$+1)

Compound 115

Methyl 3-({4-[4-({[1-(2-chlorophenyl)ethoxy]carbonyl}amino)-3-methyl-5-isoxazolyl]-benzyl}sulfanyl)propanoate $^1$H-NMR (CDCl$_3$, 400 MHz): δ7.71 (2H, bs), 7.25–7.55 (6H, m), 6.21 (1H, q, J=6.6 Hz), 6.15 (1H, bs), 3.75 (2H, s), 3.68 (3H, s), 2.66–2.71 (2H, m), 2.54–2.60 (2H, m), 2.24 (3H, s), 1.25–1.70 (3H, m) Mass spectrometry (ESI-MS): 489 (M$^+$+1)

Compound 116

1-(2-Chlorophenyl)ethyl N-(5-{4-[(ethylamino)methyl]phenyl}-3-methyl-4-isoxazolyl)-carbamate $^1$H-NMR (CDCl$_3$, 400 MHz): δ7.70 (2H, bs), 7.20–7.50 (6H, m), 6.32 (1H, bs), 6.21 (1H, q, J=6.6 Hz), 3.84 (3H, s), 2.75 (2H, q, J=7.0 Hz), 2.23 (3H, s), 1.35–1.70 (3H, m), 1.21 (3H, q, J=7.1 Hz) Mass spectrometry (ESI-MS): 414, 416 (M$^+$+1)

Compound 117

1-(2-Chlorophenyl)ethyl N-(3-methyl-5-{4-[(propylsulfanyl)methyl]phenyl}-4-isoxazolyl)-carbamate $^1$H-NMR (CDCl$_3$, 400 MHz): δ7.71 (2H, bs), 7.20–7.50 (6H, m), 6.21 (1H, q, J=6.4 Hz), 6.08 (1H, bs), 3.71 (2H, s), 2.40 (2H, t, J=7.3 Hz), 2.24 (3H, s), 1.30–1.65 (5H, m), 0.96 (3H, t, J=7.5 Hz) Mass spectrometry (ESI-MS): 445 (M$^+$+1)

Compound 118

Methyl 2-({4-[4-({[1-(2-chlorophenyl)ethoxy]carbonyl}-amino)-3-methyl-5-isoxazolyl]-benzyl}-sulfanyl)acetate $^1$H-NMR (CDCl$_3$, 400 MHz): δ7.72 (2H, bs), 7.25–7.55 (6H, m), 6.21 (1H, q, J=6.5 Hz), 6.11 (1H, bs), 3.84 (3H, s), 3.72 (3H, s), 3.07 (2H, s), 2.24 (3H, s), 1.35–1.70 (3H, m) Mass spectrometry (ESI-MS): 475 (M$^+$+1)

Compound 119

Ethyl 2-({4-[{4-(i [-(2-chlorophenyl)ethoxy]carbonyl}amino)-3-methyl-5-isoxazolyl]benzyl}-sulfanyl)acetate $^1$H-NMR (CDCl$_3$, 400 MHz): δ7.72 (2H, bs), 7.20–7.55 (6H, m), 6.21 (1H, q, J=6.1 Hz), 6.15 (1H, bs), 4.18 (2H, q, J=7.1 Hz), 3.85 (2H, s), 3.05 (2H, s), 2.24 (3H, s), 1.35–1.70 (3H, m), 1.29 (3H, t, J=7.1 Hz) Mass spectrometry (ESI-MS): 489 (M$^+$+1)

Compound 120

1-(2-Chlorophenyl)ethyl N-[5-(4-{[(2-hydroxyethyl)sulfanyl]methyl}phenyl)-3-methyl-4-isoxazolyl]carbamate $^1$H-NMR (CDCl$_3$, 400 MHz): δ7.71 (2H, bs), 7.20–7.60 (6H, m), 6.21 (1H, q, J=6.5 Hz), 6.10 (1H, bs), 3.74 (2H, s), 3.69 (2H, t, J=6.0 Hz), 2.63 (2H, t, J=6.0 Hz), 2.24 (3H, s), 2.11 (1H, bs), 1.35–1.70 (3H, m) Mass spectrometry (ESI-MS): 447 (M$^+$+1)

Compound 121

2-({4-[4-({[1-(2-Chlorophenyl)ethoxy]carbonyl}amino)-3-methyl-5-isoxazolyl]benzyl}-sulfanyl)acetic acid $^1$H-NMR (CDCl$_3$, 400 MHz): δ6.90–7.70 (9H, m), 6.14 (1H, q, J=6.4 Hz), 3.64 (2H, bs), 3.09 (2H, bs), 2.16 (3H, s), 1.30–1.60 (3H, m) Mass spectrometry (ESI-MS): 483 (M$^+$+23)

Compound 122

1-(2-Chlorophenyl)ethyl N-{5-[4-({[(2R)-2-amino-3-ethyl-3-butenyl]sulfanyl}methyl)-phenyl]-3-methyl-4-isoxazolyl}carbamate $^1$H-NMR (CDCl$_3$, 400 MHz): δ7.72 (211, bs), 7.00–7.55 (6H, m), 6.21 (1H, q, J=6.6 Hz), 4.15–4.25 (2H, m), 3.76 (2H, s), 3.57–3.62 (1H, m), 2.79–2.85 (1H, m), 2.62–2.70 (1H, m), 2.24 (3H, s), 1.35–1.80 (3H, m), 1.26 (3H, t, J=7.1 Hz) Mass spectrometry (ESI-MS): 518 (M$^+$+1)

Compound 123

1-(2-Chlorophenyl)ethyl N-(5-{4-[(allylsulfanyl)methyl]phenyl}-3-methyl-4-isoxazolyl)-carbamate $^1$H-NMR (CDCl$_3$, 400 MHz): δ7.00–7.80 (8H, m), 6.21 (1H, q, J=6.4 Hz), 6.09 (H, bs), 5.74–5.88 (1H, m), 5.05–5.18 (2H, s), 3.67 (2H, s), 3.02 (2H, d, J=7.1 Hz), 2.24 (3H, s), 1.30–1.70 (3H, m) Mass spectrometry (ESI-MS): 465 (M$^+$+23), 443 (M$^+$+1)

Compound 124

1-(2-Chlorophenyl)ethyl N-(3-methyl-5-4-[(phenethylsulfanyl)methyl]phenyl)-4-isoxazolyl)-carbamate $^1$H-NMR (CDCl$_3$, 400 MHz): δ7.10–7.80 (13H, m), 6.21 (1H, q, J=6.4 Hz), 3.70 (2H, s), 2.82–2.88 (2H, m), 2.63–2.69 (2H, m), 2.23 (3H, s), 1.25–1.70 (3H, m) Mass spectrometry (ESI-MS): 529 (M$^+$+23)

Compound 125

1-(2-Chlorophenyl)ethyl N-(5-{4-[(butylsulfanyl)methyl]phenyl)-3-methyl-4-isoxazolyl)-carbamate
Mass spectrometry (ESI-MS): 481, 483 (M$^+$+23)

Compound 126

3-({4-[4-({[1-(2-Chlorophenyl)ethoxy]carbonyl}amino)-3-methyl-5-isoxazolyl]benzyl}-sulfanyl)propanoic acid $^1$H-NMR (CDCl$_3$, 400 MHz): δ6.80–7.75 (8H, m), 6.38 (1H, bs), 6.19 (1H, q, J=6.1 Hz), 3.71 (2H, s), 2.50–2.70

(4H, m), 2.22 (3H, s), 1.30–1.70 (3H, m) Mass spectrometry (ESI-MS): 497 (M$^+$+23)

Compound 127

N-[2-({4-[4-({[1-(2-Chlorophenyl)ethoxy]carbonyl}amino)-3-methyl-5-isoxazolyl]benzyl}-sulfanyl)propanoyl]carbamic acid $^1$H-NMR (CDCl$_3$, 400 MHz): δ7.00–7.75 (8H, m), 6.17 (1H, q, J=6.4 Hz), 3.25–3.80 (3H, m), 2.96–3.20 (2H, m), 2.18 (3H, s), 1.38 (3H, s), 1.38 (3H, d, J=6.4 Hz), 1.23 (3H,t,J=7.2 Hz) Mass spectrometry (ESI-MS): 554 (M$^+$+23)

Compound 128

1-(2-Chlorophenyl)ethyl N-{5-[3-(methoxymethyl)phenyl]-3-methyl-4-isoxazolyl}carbamate $^1$H-NMR (CDCl$_3$, 400 MHz): δ7.20–7.75 (8H, m), 6.17–6.25 (1H, m), 4.46 (2H, s), 3.38 (3H, s), 2.24 (3H, s), 1.40–1.70 (3H, m) Mass spectrometry (ESI-MS): 423 (M$^+$+23)

Compound 129

1-(2-Chlorophenyl)ethyl N-{5-[3-(ethoxymethyl)phenyl]-3-methyl-4-isoxazolyl}carbamate $^1$H-NMR (CDCl$_3$, 400 MHz): δ7.20–7.80 (8H, m), 6.20 (1H, q, J=6.6 Hz), 4.50 (2H, s), 3.53 (2H, q, J=7.1 Hz), 2.24 (3H, s), 1.47–1.55 (3H, m), 1.23 (3H, t, J=7.0 Hz) Mass spectrometry (ESI-MS): 437 (M$^+$+23)

Compound 130

Methyl 2-({3-[4-({[1-(2-chlorophenyl)ethoxy]carbonyl}amino)-3-methyl-5-isoxazolyl]-benzyl}sulfanyl)acetate $^1$H-NMR (CDCl$_3$, 400 MHz): δ7.00–7.75 (8H, m), 6.24 (1H, bs), 6.15 (1H, q, J=6.5 Hz), 3.76 (2H, s), 3.60 (3H, s), 2.98 (2H, s), 2.20 (3H, s), 1.45–1.60 (3H, m) Mass spectrometry (ESI-MS): 497 (M$^+$+23)

Compound 131

1-(2-Chlorophenyl)ethyl N-[5-(3-{[(2-hydroxyethyl)sulfanyl]methyl}phenyl)-3-methyl-4-isoxazolyl]carbamate $^1$H-NMR (CDCl$_3$, 400 MHz): δ6.90–7.75 (8H, m), 6.16 (1H, q, J=6.4 Hz), 3.66 (2H, s), 3.54–3.62 (2H, m), 2.52 (2H, bs), 2.19 (3H, s), 1.35–1.70 (3H, m) Mass spectrometry (ESI-MS): 469 (M$^+$+23)

Compound 132

1-(2-Chlorophenyl)ethyl N-(5-{3-[(ethylsulfanyl)methyl]phenyl}-3-methyl-4-isoxazolyl)carbamate $^1$H-NMR (CDCl$_3$, 400 MHz): δ7.00–7.80 (8H, m), 6.21 (1H, q, J=6.1 Hz), 6.00 (1H, bs), 3.70 (2H, s), 2.39 (2H, q, J=7.3 Hz), 2.23 (3H, s), 1.30–1.70 (3H, m), 1.19 (3H, t, J=7.3 Hz) Mass spectrometry (ESI-MS): 454 (M$^+$+23)

Compound 133

Methyl 2-({4-[4-({[1-(2-chlorophenyl)ethoxy]carbonyl amino}-3-methyl-5-isoxazolyl]-benzyl}-sulfonyl)acetate $^1$H-NMR (CDCl$_3$, 400 MHz): δ7.80 (2H, s), 7.57 (2H, d, J=8.0 Hz), 7.00–7.45 (4H, m), 6.21 (1H, q, J=6.4 Hz), 6.08 (1H, bs), 4.56 (2H, s), 3.87 (3H, s), 3.80 (2H, s), 2.26 (3H, s), 1.50–1.70 (3H, m) Mass spectrometry (ESI-MS): 529 (M$^+$+23)

Compound 134

Methyl 2-({4-[4-({[1-(2-chlorophenyl)ethoxy]carbonyl}amino)-3-methyl-5-isoxazolyl]-benzyl}sulfinyl)acetate $^1$H-NMR (CDCl$_3$, 400 MHz): δ7.10–7.80 (8H, m), 6.15 (1H, q, J=6.5 Hz), 6.03 (1H, bs), 4.21 (1H, d, J=13.1 Hz), 4.05 (1H, d, J=13.0 Hz), 3.74 (3H, s), 3.54 (1H, d, J=13.0 Hz), 3.44 (1H, d, J=13.0 Hz), 2.19 (3H, s), 1.53 (3H, bs) Mass spectrometry (ESI-MS): 513 (M$^+$+23)

Compound 135

1-(2-Chlorophenyl)ethyl N-[5-(4-{[(2,3-dihydroxypropyl)sulfanyl]methyl}phenyl)-3-methyl-4-isoxazolyl]carbamate $^1$H-NMR (CDCl$_3$, 400 MHz): δ7.72 (2H, bs), 7.20–7.60 (6H, m), 6.21 (1H, q, J=6.5 Hz), 6.11 (1H, bs), 3.76 (3H, s), 3.45–3.75 (2H, m), 2.50–2.70 (3H, m), 2.24 (3H, s), 2.02 (1H, bs), 1.60 (3H, bs) Mass spectrometry (ESI-MS): 499 (M$^+$+23)

Compound 136

1-(2-Chlorophenyl)ethyl N-(3-methyl-5-{4-[(1H-1,2,4-triazol-3-ylsulfanyl)methyl]-phenyl}-4-isoxazolyl)carbamate $^1$H-NMR (CDCl$_3$, 400 MHz): δ8.09 (1H, s), 7.20–7.75 (8H, m), 6.21 (1H, q, J=6.6 Hz), 6.11 (1H, bs), 4.36 (2H, s), 2.24 (3H, s), 1.30–1.75 (3H, m) Mass spectrometry (ESI-MS): 492 (M$^+$+23)

Compound 137

1-(2-Chlorophenyl)ethyl N-[3-methyl-5-(4-{[(1-methyl-1H-1,2,3,4-tetrazol-5-yl)-sulfanyl]methyl}phenyl)-4-isoxazolyl]carbamate $^1$H-NMR (CDCl$_3$, 400 MHz): δ7.72 (2H, bs), 7.25–7.55 (6H, m), 6.21 (1H, q, J=6.5 Hz), 5.99 (1H, bs), 4.56 (2H, s), 3.94 (3H, s), 2.25 (3H, s), 1.30–1.70 (3H, m) Mass spectrometry (ESI-MS): 507 (M$^+$+23)

Compound 138

1-(2-Chlorophenyl)ethyl N-{3-methyl-5-[4-({2-(methylamino)-2-oxoethyl]sulfanyl}-methyl)phenyl]-4-isoxazolyl}carbamate $^1$H-NMR (CDCl$_3$, 400 MHz): δ7.73 (2H, bs), 7.20–7.55 (6H, m), 6.54 (1H, bs), 6.21 (1H, q, J=6.5 Hz), 6.12 (1H, bs), 3.74 (2H, s), 3.12 (2H, s), 2.75 (3H, d, J=4.9 Hz), 2.25 (3H, s), 1.30–1.70 (3H, m) Mass spectrometry (ESI-MS): 474 (M$^+$+1), 496 (M$^+$+23)

Compound 139

1-(2-Chlorophenyl)ethyl N-(5-{4-[({2-[(2-furylmethyl)amino]-2-oxoethyl}sulfanyl)-methyl]phenyl}-3-methyl-4-isoxazolyl)carbamate $^1$H-NMR (CDCl$_3$, 400 MHz): δ7.20–7.75 (9H, m), 6.83 (1H, bs), 6.10–6.26 (4H, m), 4.32 (2H, d, J=5.4 Hz), 3.64 (2H, s), 3.05 (2H, s), 2.17 (3H, s), 1.30–1.65 (3H, m) Mass spectrometry (ESI-MS): 562 (M$^+$+23)

Compound 140

Ethyl 2-({3-[4-({[1-(2-chlorophenyl)ethoxy]carbonyl}amino)-3-methyl-5-isoxazolyl]benzyl}sulfanyl)acetate $^1$H-NMR (CDCl$_3$, 400 MHz): δ7.00–7.80 (8H, m), 6.32 (1H, bs), 6.20 (1H, q, J=6.4 Hz), 4.05–4.20 (2H, m), 3.81 (2H, s), 3.02 (2H, s), 2.24 (3H, s), 1.30–1.70 (3H, m), 1.24 (3H, t, J=7.2 Hz) Mass spectrometry (ESI-MS): 487 (M$^+$−1), 511 (M$^+$+23)

Compound 141

1-(2-Chlorophenyl)ethyl N-(5-{3-[(allylsulfanyl)methyl]phenyl}-3-methyl-4-isoxazolyl)-carbamate $^1$H-NMR (CDCl$_3$, 400 MHz): δ7.00–7.75 (8H, m), 6.16 (1H, q, J=6.6 Hz), 5.95 (1H, bs), 5.65–5.77 (1H, m), 4.97–5.10 (2H, m), 3.60 (2H, s), 2.95 (2H, dt, J=7.1 Hz, J=1.1 Hz), 2.19 (3H, s), 1.45–1.60 (3H, m) Mass spectrometry (ESI-MS): 441 (M$^+$−1), 465 (M$^+$+23)

Compound 142

1-(2-Chlorophenyl)ethyl N-(3-methyl-5-{3-[(phenethylsulfanyl)methyl]phenyl}-4-isoxazolyl)-carbamate $^1$H-NMR (CDCl$_3$, 400 MHz): δ7.00–7.75 (13H, m), 6.15 (1H, q, J=6.4 Hz), 5.90 (1H, bs), 3.64 (2H, s), 2.76 (2H, t, J=7.8 Hz), 2.59 (2H, t, J=7.8 Hz), 2.19 (3H, s), 1.45–1.52 (3H, m) Mass spectrometry (ESI-MS): 505 (M$^+$−1), 529 (M$^+$+23)

Compound 143

1-(2-Chlorophenyl)ethyl N-(3-methyl-5-{3-[(1H-1,2,4-triazol-3-ylsulfanyl)methyl]phenyl}-4-isoxazolyl)carbamate $^1$H-NMR (CDCl$_3$, 400 MHz): δ6.00–8.00 (11H, m), 4.23 (2H, s), 2.23 (3H, s), 1.00–1.65 (3H, m) Mass spectrometry (ESI-MS): 468 (M$^+$−1), 492 (M$^+$+23)

Compound 144

4-[4-({[1-(2-Chlorophenyl)ethoxy]carbonyl}amino)-3-methyl-5-isoxazolyl]benzyl ethanethioate $^1$H-NMR (CDCl$_3$, 400 MHz): δ7.20–7.75 (8H, m), 6.05–6.15 (2H, m), 4.04 (2H, s), 2.28 (3H, s), 2.15 (3H, s), 1.25–1.65 (3H, m) Mass spectrometry (ESI-MS): 445 (M$^+$+1)

Compound 145

1-(2-Chlorophenyl)ethyl N-{5-[4-({[2-(acetylamino)ethyl]sulfanyl}methyl)phenyl]-3-methyl-4-isoxazolyl}carbamate $^1$H-NMR (CDCl$_3$, 400 MHz): δ6.80–7.75 (8H, m), 6.54 (1H, bs), 6.13 (1H, q, J=6.3 Hz), 5.84 (1H, bs), 3.64 (2H, s), 3.24 (2H, d, J=5.8 Hz), 2.46 (2H, t, J=5.8 Hz), 2.16 (3H, s), 1.86 (3H, ss), 1.25–1.70 (3H, m) Mass spectrometry (ESI-MS): 488 (M$^+$+1), 510 (M$^+$+23)

Compound 146

Methyl 3-({4-[4-({[1-(2-chlorophenyl)ethoxy]carbonyl}amino)-3-ethyl-5-isoxazolyl]benzyl}sulfanyl)propanoate $^1$H-NMR (CDCl$_3$, 400 MHz): δ7.00–7.80 (8H, m), 6.21 (1H, q, J=6.4 Hz), 5.97 (1H, bs), 3.75 (2H, s), 3.69 (3H, s), 2.54–2.73 (6H, m), 1.50–1.70 (3H, m), 1.30 (3H, t, J=7.6 Hz) Mass spectrometry (ESI-MS): 503 (M$^+$+1), 525 (M$^+$+23)

Compound 147

3-({4-[4-({[1-(2-Chlorophenyl)ethoxy]carbonyl}amino)-3-ethyl-5-isoxazolyl]benzyl}sulfanyl)propanoic acid $^1$H-NMR (CDCl$_3$, 400 MHz): δ6.70–7.75 (8H, m), 6.00–6.18 (2H, m), 3.67 (2H, s), 2.49–2.64 (6H, m), 1.16–1.60 (6H, m) Mass spectrometry (ESI-MS): 489 (M$^+$+1), 511 (M$^+$+23)

Compound 148

2-({4-[4-({[1-(2-Chlorophenyl)ethoxy]carbonyl}amino)-3-methyl-5-isoxazolyl]benzyl}sulfanyl)propanoic acid $^1$H-NMR (CDCl$_3$, 400 MHz): δ7.64 (2H, bs), 6.80–7.50 (6H, m), 6.14 (1H, q, J=6.5 Hz), 3.86 (1H, d, J=13.7 Hz), 3.74 (1H, d, J=13.7 Hz), 3.21 (1H, q, J=7.3 Hz), 2.17 (3H, s), 1.30–1.60 (3H, m), 1.33 (3H, d, J=7.3 Hz) Mass spectrometry (ESI-MS): 475 (M$^+$+1), 497 (M$^+$+23)

Compound 149

1-(2-Chlorophenyl)ethyl N-(3-methyl-5-{4-[({2-[(1H-2-pyrrolylcarbonyl)amino]ethyl}-sulfanyl)methyl]phenyl}-4-isoxazolyl)carbamate $^1$H-NMR (CDCl$_3$, 400 MHz): δ7.68 (2H, d, J=8.3 Hz), 7.00–7.55 (7H, m), 6.89 (1H, bs), 6.52 (1H, s), 5.95–6.40 (3H, m), 3.76 (2H, s), 3.45 (1H, bs), 3.11 (1H, bs), 2.63 (2H, s), 2.25 (3H, s), 1.59 (3H, s) Mass spectrometry (ESI-MS): 539 (M$^+$+1)

Compound 150

1-(2-Chlorophenyl)ethyl N-[5-(4-{[(2-chloroethyl)sulfanyl]methyl}phenyl)-3-methyl-4-isoxazolyl]carbamate $^1$H-NMR (CDCl$_3$, 400 MHz): δ7.71 (2H, bs), 7.00–7.60 (6H, m), 6.20 (1H, q, J=6.5 Hz), 5.96 (1H, bs), 3.72 (2H, t, J=7.2 Hz), 3.09 (2H, t, J=7.2 Hz), 2.23 (3H, s), 1.30–1.70 (3H, m) Mass spectrometry (ESI-MS): 417, 419 (M+1), 441 (M+23)

Compound 151

2-({4-[4-({[1-(2-Chlorophenyl)ethoxy]carbonyl}amino)-3-methyl-5-isoxazolyl]benzyl}sulfanyl)-1-ethanesulfonic acid $^1$H-NMR (CDCl$_3$, 400 MHz): δ9.44 (1H, s), 7.40–8.00 (8H, m), 6.05 (1H, q, J=6.4 Hz), 4.57 (1H, s), 3.85 (1H, s), 3.25–3.30 (2H, m), 2.70 (3H, s), 2.15–2.25 (2H, m), 1.30–1.45 (3H, m) Mass spectrometry (ESI-MS): 509, 511 (M$^+$−1)

Compound 152

3-({4-[4-({[1-(2-Chlorophenyl)ethoxy]carbonyl}amino)-3-methyl-5-isoxazolyl]benzyl}sulfanyl)-1-propanesulfonic acid $^1$H-NMR (CDCl$_3$, 400 MHz): δ9.70 (1H, s), 7.30–7.90 (8H, m), 5.90–6.05 (1H, m), 4.52 (1H, s), 3.76 (1H, s), 3.14–3.23 (2H, m), 2.48–2.53 (3H, m), 2.09–2.17 (2H, m), 1.75–1.90 (2H, m), 1.32 (3H, t, J=7.2 Hz) Mass spectrometry (ESI-MS): 523 (M$^+$−1)

Compound 153

Methyl 2-({4-[4-({[1-(2-chlorophenyl)ethoxy] carbonyl}amino)-3-ethyl-5-isoxazolyl]benzyl}-sulfanyl)acetate $^1$H-NMR (CDCl$_3$, 400 MHz): δ7.25–7.80 (8H, m), 6.21 (1H, q, J=6.6 Hz), 5.97 (1H, bs), 3.85 (2H, s), 3.73 (3H, s), 3.07 (2H, s), 2.66 (2H, q, J=7.6 Hz), 1.50–1.70 (3H, m), 1.30 (3H, t, J=7.6 Hz) Mass spectrometry (ESI-MS): 511 (M$^+$+23)

Compound 154

2-({4-[4-({[1-(2-Chlorophenyl)ethoxy] carbonyl}amino)-3-ethyl-5-isoxazolyl]benzyl}-sulfanyl)acetic acid $^1$H-NMR (CDCl$_3$, 400 MHz): δ6.75–7.60 (9H, m), 6.03 (1H, q, J=6.4 Hz), 3.40–3.65 (2H, m), 3.02 (2H, bs), 2.40–2.55 (2H, m), 1.10–1.46 (6H, m) Mass spectrometry (ESI-MS): 497 (M$^+$+23)

Compound 155

1-(2-Fluorophenyl)ethyl N-{5-[4-(chloromethyl) phenyl]-3-methyl-4-isoxazolyl}carbamate $^1$H-NMR (CDCl$_3$, 400 MHz): δ7.74 (2H, bs), 6.90–7.50 (6H, m), 6.13 (1H, q, J=6.6 Hz), 6.02 (1H, bs), 4.60 (2H, s), 2.24 (3H, s), 1.50–1.70 (3H, m) Mass spectrometry (ESI-MS): 387 (M$^+$−1)

Compound 156

Methyl 3-({4-[4-({[1-(2-fluorophenyl)ethoxy] carbonyl}amino)-3-methyl-5-isoxazolyl]-benzyl}-sulfanyl)propanoate $^1$H-NMR (CDCl$_3$, 400 MHz): δ7.64 (2H, bs), 6.80–7.40 (6H, m), 6.06 (1H, q, J=6.6 Hz), 5.99 (1H, bs), 3.68 (2H, s), 3.61 (3H, s), 2.59–2.60 (2H, m), 2.47–2.52 (2H, m), 2.16 (3H, s), 1.48–1.65 (3H, m) Mass spectrometry (ESI-MS): 495 (M$^+$+23)

Compound 157

3-({4-[4-({[1-(2-Fluorophenyl)ethoxy] carbonyl}amino)-3-methyl-5-isoxazolyl]benzyl}-sulfanyl)propanoic acid $^1$H-NMR (CDCl$_3$, 400 MHz): δ7.62 (2H, bs), 6.70–7.50 (6H, m), 6.12 (1H, bs), 6.05 (1H, q, J=6.4 Hz), 3.67 (2H, s), 2.48–2.65 (4H, m), 2.16 (3H, s), 2.10 (2H, s), 1.16–1.64 (3H, m) Mass spectrometry (ESI-MS): 481 (M$^+$+23)

Compound 158

2-({3-[4-({[1-(2-Chlorophenyl)ethoxy] carbonyl}amino)-3-methyl-5-isoxazolyl]benzyl}-sulfanyl)-1-ethanesulfonic acid $^1$H-NMR (CDCl$_3$, 400 MHz): δ6.90–8.20 (8H, m), 6.00–6.20 (2H, m), 4.43 (1H, bs), 3.57 (2H, s), 2.55–3.20 (4H, m), 2.09 (3H, s), 1.00–1.75 (3H, m) Mass spectrometry (ESI-MS): 509, 511 (M$^+$+1)

Compound 159

3-({3-[4-({[1-(2-Chlorophenyl)ethoxy] carbonyl}amino)-3-methyl-5-isoxazolyl]benzyl}-sulfanyl)propanoic acid $^1$H-NMR (CDCl$_3$, 400 MHz): δ7.00–7.90 (8H, m), 6.28 (1H, bs), 6.18 (1H, q, J=6.4 Hz), 3.67 (2H, s), 2.45–2.65 (4H, m), 2.20 (3H, s), 1.40–1.60 (3H, m) Mass spectrometry (ESI-MS): 473 (M−1) 497 (M$^+$+23)

Compound 160

1-(2-Fluorophenyl)ethyl N-{5-[4-(chloromethyl) phenyl]-3-ethyl-4-isoxazolyl}carbamate $^1$H-NMR (CDCl$_3$, 400 MHz): δ7.71 (2H, bs), 6.90–7.50 (6H, m), 6.10 (1H, q, J=6.6 Hz), 5.95 (1H, bs), 4.58 (2H, s), 2.63 (2H, q, J=7.6 Hz), 1.50–1.70 (3H, m), 1.27 (3H, t, J=7.6 Hz) Mass spectrometry (ESI-MS): 401 (M$^+$−1)

Compound 161

2,2,2-Trifluoro-1-phenylethyl N-{5-[4-(chloromethyl)phenyl]-3-methyl-4-isoxazolyl}-carbamate $^1$H-NMR (CDCl$_3$, 400 MHz): 7.69 (2H, d, J=7.3 Hz), 7.20–7.60 (7H, m), 6.32 (1H, bs), 6.10–6.20 (1H, m), 4.59 (2H, s), 2.24 (3H, s) Mass spectrometry (ESI-MS): 425 (M$^+$+1), 445, 447 (M$^+$+23)

Compound 162

Methyl 3-{[4-(3-methyl-4-{[(2,2,2-trifluoro-1-phenylethoxy)carbonyl]amino}-5-isoxazolyl)-benzyl]-sulfanyl}propanoate $^1$H-NMR (CDCl$_3$, 400 MHz): δ7.20–7.75 (9H, m), 6.25 (1H, bs), 6.10–6.20 (1H, m), 3.75 (2H, s), 3.69 (3H, s), 2.66–2.72 (2H, m), 2.53–2.59 (2H, m), 2.24 (3H, s) Mass spectrometry (ESI-MS): 531, 532 (M$^+$+23)

Compound 163

3-{[4-(3-Methyl-4-{[(2,2,2-trifluoro-1-phenylethoxy)carbonyl]amino}-5-isoxazolyl) benzyl]-sulfanyl}propanoic acid $^1$H-NMR (CDCl$_3$, 400 MHz): δ7.20–7.75 (9H, m), 6.54 (1H, bs), 6.10–6.20 (1H, m), 3.72 (2H, s), 2.50–2.80 (4H, m), 2.23 (3H, s) Mass spectrometry (ESI-MS): 493 (M$^+$−1)

Compound 164

2,2,2-Trifluoro-1-phenylethyl N-{5-[4-(chloromethyl)phenyl]-3-ethyl-4-isoxazolyl}carbamate $^1$H-NMR (CDCl$_3$, 400 MHz): δ7.00–7.75 (9H, m), 6.16–6.26 (1H, m), 6.00–6.12 (1H, m), 4.52 (2H, s), 2.57 (2H, q, J=7.5 Hz), 1.21 (3H, t, J=7.5 Hz) Mass spectrometry (ESI-MS): 437 (M$^+$−1)

Compound 165

Methyl 3-({4-[3-ethyl-4-({[1-(2-fluorophenyl) ethoxy]carbonyl}amino)-5-isoxazolyl]-benzyl}sulfanyl)propanoate $^1$H-NMR (CDCl$_3$, 400 MHz): δ6.80–7.75 (8H, m), 6.06 (1H, q, J=6.6 Hz), 5.90 (1H, bs), 3.68 (2H, s), 3.62 (3H, s), 2.54–2.65 (4H, m), 2.47–2.53 (2H, m), 1.30–1.65 (3H, in), 1.21 (3H, t, J=7.6 Hz) Mass spectrometry (ESI-MS): 485 (M$^+$−1), 509 (M$^+$+23)

Compound 166

Methyl 3-{[4-(3-ethyl-4-{[(2,2,2-trifluoro-1-phenylethoxy)carbonyl]amino}-5-isoxazolyl)-benzyl]sulfanyl}propanoate $^1$H-NMR (CDCl$_3$, 400 MHz): δ7.10–7.70 (9H, m), 6.20 (1H, bs), 6.00–6.13 (1H, m), 3.67 (2H, s), 3.61 (3H, s), 2.46–2.64 (6H, m), 1.21 (3H, t, J=7.4 Hz) Mass spectrometry (ESI-MS): 521 (M$^+$–1), 545 (M$^+$+23)

Compound 167

3-({4-[3-Ethyl-4-({[1-(2-fluorophenyl)ethoxy]carbonyl}amino)-5-isoxazolyl]benzyl}-sulfanyl)propanoic acid $^1$H-NMR (CDCl$_3$, 400 MHz): δ6.80–7.70 (8H, m), 6.05 (1H, q, J=6.6 Hz), 5.94 (1H, bs), 3.69 (2H, s), 2.49–2.65 (6H, m), 1.25–1.70 (3H, in), 1.21 (3H, t, J=7.6 Hz) Mass spectrometry (ESI-MS): 471 (M$^+$–1), 495 (M$^+$+23)

Compound 168

Ethyl 2-({4-[4-({[1-(2-chlorophenyl)ethoxy]carbonyl}amino)-3-methyl-5-isoxazolyl]-benzyl}oxy)acetate $^1$H-NMR (CDCl$_3$, 400 MHz): δ7.75 (2H, bs), 7.25–7.55 (6H, m), 6.22 (1H, q, J=6.5 Hz), 6.03 (1H, bs), 4.67 (2H, s), 4.24 (2H, q, J=7.2 Hz), 4.12 (2H, s), 2.25 (3H, s), 1.40–1.70 (3H, m), 1.30 (3H, t, J=7.2 Hz) Mass spectrometry (ESI-MS): 495 (M$^+$+23)

Compound 169

Ethyl 2-{[4-(3-methyl-4-{[(2,2,2-trifluoro-1-phenylethoxy)carbonyl]amino}-5-isoxazolyl)-benzyl]oxy}acetate $^1$H-NMR (CDCl$_3$, 400 MHz): δ7.65–7.75 (2H, m), 7.20–7.60 (7H, m), 6.44 (1H, bs), 6.10–6.20 (1H, m), 4.66 (2H, s), 4.25 (2H, q, J=7.2 Hz), 4.13 (2H, s), 2.23 (3H, s), 1.30 (3H, t, J=7.2 Hz) Mass spectrometry (ESI-MS): 491 (M$^+$–1)

Example 170

Establishment of HepG2 Cell Line Expressing Human EDG-2

An about 360 bp DNA fragment, which corresponds to that reported by An et al. (Biochem. Biophys. Res. Commun. 231: 619 (1997)), was obtained by PCR (polymerase chain reaction) from the human brain cDNA library (Clontech Laboratories Inc., USA). The total nucleotide sequence was determined using a DNA sequenser, and it was confirmed that the sequence corresponds completely to that reported by An et al. (Biochem. Biophys. Res. Commun.231: 619 (1997)). cDNA of the cloned human EDG-2 was introduced into pEFneo, which is an animal expression vector (Proc. Natl. Acad. Sci. USA 91: 158 (1994)) to obtain a human EDG-2 expression plasmid. The human EDG-2 expression plasmid was introduced into HepG2 cells by electroporation. After the introduction, culturing was continued while exchanging selective media every 3 to 4 days, thereby obtaining an expressed colony. Regarding these cells, Ca-influx and cell-proliferation by LPA, level of [$^3$H] LPA binding and the like were inspected to select a cell line which highly expresses human EDG-2 (human EDG-2/HepG2). The obtained cell line was used to assay the activity in the following Examples 104 and 105.

Example 171

Assay of Inhibitory Activity on Cell Activation (Function for Elevating Intracellular Ca$^{2+}$ Level)

Human EDG-2/HepG2 cells were washed and then suspended in 0.1% BSA (bovine serum albumin)-containing HEPES buffer. A fluorescent indicator, fura-2/AM (Wako Pure Chemical Industries, Ltd.), was added, and the mixture was shaken at room temperature for 45 minutes so that the indicator is included in the cell. Cells were washed again and then suspended in 0.1% BSA-containing HEPES buffer, and intracellular Ca$^{2+}$ level was assayed using FDSS2000 (Hamamatsu Photonics). The compounds obtained in Examples 1 to 102 were used as test compounds for Compound Nos.1 to 102. Each test compound was added to the cell suspension followed by the addition of LPA, thereby examining the inhibitory activity of the test compound on the function of LPA for elevating the intracellular Ca level. The elevation of intracellular Ca$^{2+}$ level by LPA without the addition of test compounds was set as 100% and resting Ca$^{2+}$ level before the addition of LPA was set as 0%, thereby determining the concentration of 50% inhibition for the elevation of intracellular Ca$^{2+}$ level (IC$_{50}$ value). The lower the IC$_{50}$ value, the higher the antagonistic activity on the LPA receptor. The results are shown in Table 1.

TABLE 1

| Compound No. | IC$_{50}$(μM) |
| --- | --- |
| Compound 1 | 100 |
| Compound 2 | 30 to 100 |
| Compound 3 | 3 |
| Compound 4 | 3 |
| Compound 5 | 10 to 30 |
| Compound 6 | 10 |
| Compound 7 | 30 |
| Compound 8 | 3 to 10 |
| Compound 9 | 10 to 30 |
| Compound 10 | 100 to |
| Compound 11 | 10 to 30 |
| Compound 12 | 30 to 100 |
| Compound 13 | 30 |
| Compound 14 | 30 to 100 |
| Compound 15 | 30 |
| Compound 16 | 3 to 10 |
| Compound 17 | 3 |
| Compound 18 | 3 |
| Compound 19 | 3 to 10 |
| Compound 20 | 3 |
| Compound 21 | 3 |
| Compound 22 | 3 to 10 |
| Compound 23 | 10 |
| Compound 24 | 100 |
| Compound 25 | 30 to 100 |
| Compound 26 | 100 |
| Compound 27 | 30 |
| Compound 28 | 10 to 30 |
| Compound 29 | 10 |
| Compound 30 | 3 to 10 |
| Compound 31 | 10 |
| Compound 32 | 3 |
| Compound 33 | 3 to 10 |
| Compound 34 | 10 |
| Compound 35 | 3 to 10 |
| Compound 36 | 3 to 10 |
| Compound 37 | 30 |
| Compound 38 | 10 |
| Compound 39 | 10 |
| Compound 40 | 10 |
| Compound 41 | 3 to 10 |
| Compound 42 | 10 |
| Compound 43 | 3 to 10 |
| Compound 44 | 3 |
| Compound 45 | 3 |
| Compound 46 | 3 to 10 |
| Compound 47 | 1 |
| Compound 48 | 3 to 10 |
| Compound 49 | 10 to 30 |
| Compound 50 | 10 to 30 |
| Compound 51 | 10 to 30 |
| Compound 52 | 30 |
| Compound 53 | 30 |

TABLE 1-continued

| Compound No. | IC$_{50}$($\mu$M) |
|---|---|
| Compound 54 | 10 to 30 |
| Compound 55 | 3 to 10 |
| Compound 56 | 3 to 10 |
| Compound 57 | 3 |
| Compound 58 | 10 |
| Compound 59 | 3 to 10 |
| Compound 60 | 1 to 3 |
| Compound 61 | 3 to 10 |
| Compound 62 | 3 |
| Compound 63 | 30 |
| Compound 64 | 10 to 30 |
| Compound 65 | 10 to 30 |
| Compound 66 | 10 |
| Compound 67 | 3 |
| Compound 68 | 3 to 10 |
| Compound 69 | 3 to 10 |
| Compound 70 | 1 to 3 |
| Compound 71 | 3 |
| Compound 72 | 10 to 30 |
| Compound 73 | 1 to 3 |
| Compound 74 | 1 to 3 |
| Compound 75 | 3 to 10 |
| Compound 76 | 1 to 3 |
| Compound 77 | 1 to 3 |
| Compound 78 | 30 |
| Compound 79 | 3 |
| Compound 80 | 1 to 3 |
| Compound 81 | 30 to 100 |
| Compound 82 | 10 to 30 |
| Compound 83 | 10 |
| Compound 84 | 3 to 10 |
| Compound 85 | 3 to 10 |
| Compound 86 | 1 to 3 |
| Compound 87 | 3 |
| Compound 88 | 3 to 10 |
| Compound 89 | 10 to 30 |
| Compound 90 | 10 |
| Compound 91 | 10 to 30 |
| Compound 92 | 10 to 30 |
| Compound 93 | 3 to 10 |
| Compound 94 | 30 to 100 |
| Compound 95 | 30 to 100 |
| Compound 96 | 30 to 100 |
| Compound 97 | 30 to 100 |
| Compound 98 | 30 to 100 |
| Compound 99 | 30 to 100 |
| Compound 100 | 30 to 100 |
| Compound 101 | 30 to 100 |
| Compound 102 | 30 to 100 |
| Compound 103 | 10 |
| Compound 104 | 10 to 30 |
| Compound 105 | 10 to 30 |
| Compound 106 | 3 to 10 |
| Compound 107 | 3 to 10 |
| Compound 108 | 3 to 10 |
| Compound 109 | 10 to 30 |
| Compound 110 | 10 to 30 |
| Compound 111 | 10 to 30 |
| Compound 112 | 10 to 30 |
| Compound 113 | 10 to 30 |
| Compound 114 | 10 to 30 |
| Compound 115 | 1 to 3 |
| Compound 116 | 30 to 100 |
| Compound 117 | 3 to 10 |
| Compound 118 | 1 to 3 |
| Compound 119 | 3 to 10 |
| Compound 120 | 3 to 10 |
| Compound 121 | 3 to 10 |
| Compound 122 | 3 to 10 |
| Compound 123 | 3 to 10 |
| Compound 124 | 10 to 30 |
| Compound 125 | 10 to 30 |
| Compound 126 | 3 to 10 |
| Compound 127 | 3 to 10 |
| Compound 128 | 3 to 10 |
| Compound 129 | 3 to 10 |
| Compound 130 | 3 to 10 |

TABLE 1-continued

| Compound No. | IC$_{50}$($\mu$M) |
|---|---|
| Compound 131 | 3 |
| Compound 132 | 3 |
| Compound 133 | 10 |
| Compound 134 | 3 to 10 |
| Compound 135 | 3 to 10 |
| Compound 136 | 3 to 10 |
| Compound 137 | 3 to 10 |
| Compound 138 | 3 to 10 |
| Compound 139 | 10 |
| Compound 140 | 3 to 10 |
| Compound 141 | 3 to 10 |
| Compound 142 | 3 to 10 |
| Compound 143 | 3 to 10 |
| Compound 144 | 1 to 3 |
| Compound 145 | 3 to 10 |
| Compound 146 | 3 to 10 |
| Compound 147 | 3 to 10 |
| Compound 148 | 10 to 30 |
| Compound 149 | 10 to 30 |
| Compound 150 | 3 |
| Compound 151 | 3 to 10 |
| Compound 152 | 3 to 10 |
| Compound 153 | 3 to 10 |
| Compound 154 | 3 to 10 |
| Compound 155 | 3 to 10 |
| Compound 156 | 10 |
| Compound 157 | 3 |
| Compound 158 | 3 to 10 |
| Compound 159 | 3 |
| Compound 160 | 3 to 10 |
| Compound 161 | 3 to 10 |
| Compound 162 | 3 to 10 |
| Compound 163 | 3 to 10 |
| Compound 164 | 3 to 10 |
| Compound 165 | 3 to 10 |
| Compound 166 | 10 |
| Compound 167 | 3 to 10 |
| Compound 168 | 3 to 10 |
| Compound 169 | 3 to 10 |

As is apparent from Table 1 above, most of the tested compounds had IC$_{50}$ of 100 $\mu$M or below and, particularly, Compound Nos. 3, 4, 6, 8, 16, 17, 18, 19, 20, 21, 22, 23, 29, 30, 31, 32, 33, 34, 35, 36, 38, 39, 40, 41, 42, 43, 44, 45, 46, 47, 48, 55, 56, 57, 58, 59, 60, 61, 62, 66, 67, 68, 69, 70, 71, 73, 74, 75, 76, 77, 79, 80, 83, 84, 85, 86, 87, 88, 90, 93, 103, 106 to 108, 115, 117 to 123, 126 to 147, and 150 to 169 had IC$_{50}$ of 10 $\mu$M or below. This indicates that the antagonistic action on the LPA receptor is high.

Example 172

Assay of inhibitory activity on [$^3$H] Thymidine Incorporation

Human EDG-2/HepG2 cells suspended in 10% bovine serum-containing DMEM (Dulbecco's modified eagle medium) were plated on a 96-well plate and, on the next day, the medium was exchanged with serum-free DMEM. 24 hours later, the medium was exchanged with DMEM containing LPA or DMEM containing no LPA, cells were cultured for further 16 hours, and [$^3$H] thymidine was then added. After culturing for 8 hours subsequent to the addition of [$^3$H] thymidine, cells were washed with PBS (phosphate-buffered saline), and the amount of [$^3$H] thymidine incorporated into the cells were assayed by Betaplate filter counter system (Amersham Pharmacia Biotech). The difference between the amount of [$^3$H] thymidine incorporated in the LPA-added well and the amount of [$^3$H] thymidine incorporated in the well containing no LPA represents the amount of [$^3$H] thymidine incorporation accelerated by LPA.

The increase of [$^3$H] thymidine incorporation without the addition of test compounda was set as 100% and the concentration of compound with 50% inhibition in the increase of [$^3$H] thymidine incorporation (IC$_{50}$ value) was determined. The test compounds were added immediately before the LPA addition. The results are shown in Table 2.

TABLE 2

| Compound No. | Inhibition of proliferation IC$_{50}$(μM) |
| --- | --- |
| Compound 4 | 1 |
| Compound 20 | 1 |
| Compound 32 | 1 |
| Compound 47 | 0.3 |
| Compound 62 | 3 |
| Compound 67 | 1 |
| Compound 71 | 1 |
| Compound 103 | 0.3 |
| Compound 104 | 3 |
| Compound 105 | 1 |
| Compound 106 | 1 to 3 |
| Compound 107 | 0.03 to 0.1 |
| Compound 108 | 0.1 to 0.3 |
| Compound 109 | 1 to 3 |
| Compound 110 | 0.3 to 1 |
| Compound 111 | 1 to 3 |
| Compound 112 | 0.3 to 1 |
| Compound 113 | 0.1 to 0.3 |
| Compound 114 | 0.3 to 1 |
| Compound 115 | 0.01 to 0.03 |
| Compound 116 | 0.3 to 1 |
| Compound 117 | 0.03 to 0.1 |
| Compound 118 | 0.1 to 0.3 |
| Compound 119 | 0.1 to 0.3 |
| Compound 120 | 0.1 to 0.3 |
| Compound 121 | 0.03 to 0.1 |
| Compound 122 | 0.1 to 0.3 |
| Compound 123 | 0.1 to 0.3 |
| Compound 124 | 0.1 to 0.3 |
| Compound 125 | 0.1 to 0.3 |
| Compound 126 | 0.01 to 0.03 |
| Compound 127 | 0.1 to 0.3 |
| Compound 128 | 0.1 to 0.3 |
| Compound 129 | 0.3 to 1 |
| Compound 130 | 0.3 to 1 |
| Compound 132 | 0.3 to 1 |
| Compound 133 | 0.1 to 0.3 |
| Compound 134 | 0.1 to 0.3 |
| Compound 135 | 0.1 to 0.3 |
| Compound 136 | 0.1 to 0.3 |
| Compound 137 | 0.1 to 0.3 |
| Compound 138 | 0.1 to 0.3 |
| Compound 139 | 0.03 to 0.1 |
| Compound 140 | 0.3 to 1 |
| Compound 141 | 0.3 to 1 |
| Compound 142 | 0.3 |
| Compound 143 | 0.1 to 0.3 |
| Compound 144 | 0.03 to 0.1 |
| Compound 145 | 0.3 to 1 |
| Compound 146 | 0.03 to 0.3 |
| Compound 147 | 0.03 to 0.1 |
| Compound 148 | 0.1 to 0.3 |
| Compound 149 | 0.03 |
| Compound 150 | 0.1 to 0.3 |
| Compound 151 | 0.1 |
| Compound 152 | 0.3 |
| Compound 153 | 0.3 |
| Compound 154 | 0.1 to 0.3 |
| Compound 156 | 0.3 to 1 |
| Compound 157 | 0.3 to 1 |
| Compound 158 | 1 |
| Compound 159 | 0.3 |
| Compound 161 | 1 to 3 |
| Compound 162 | 0.03 to 0.1 |
| Compound 163 | 0.03 to 0.1 |
| Compound 164 | 0.3 to 1 |
| Compound 165 | 0.1 to 0.3 |
| Compound 166 | 0.1 |
| Compound 167 | 0.03 to 0.1 |
| Compound 168 | 1 |
| Compound 169 | 1 to 3 |

As is apparent from Table 2 above, the compounds of the present invention significantly inhibit the incorporation of [$^3$H] thymidine into the cells. This indicates that the compounds of the present invention possess an inhibitory property against cell proliferation. The compounds shown in Table 2 are simple representative examples. Other compounds shown in Table 1 also inhibit the incorporation of [$^3$H] thymidine in the same manner as described above.

Example 173

Evaluation of the Function Against a Model of Lactic Acid Induced Peripheral Circulatory Disturbance Peripheral arterial obstructions including clinical arteriosclerosis obliterans (ASO) are, in common, chronic diseases, which often cause ulcer or necrosis in lower limbs, and lesions are worsened by arterial thrombotic infarcts upstream of the lesions. Therefore, the target of the treatment for the above diseases is to inhibit the progress and to eliminate the ischemic symptoms. Antiplatelet drugs and anticoagulants are often used therefor. Since lysophosphatidic acids (LPA) are known to be released from activated platelets, the compounds according to the present invention can be sufficiently expected to exhibit therapeutic effects on the above diseases. ID3016511 (Compound 115), which is one of the compounds according to the present invention, is selected as an example and administered daily to a rat model of lactic acid induced peripheral circulatory disturbance used as an animal model of peripheral arterial obstruction to examine the drug's therapeutic effect.

13-week old Wister male rats were used in test groups of 10 rats. Each rat was fixed in a face-up position under anesthesia by 40 mg/kg of intraperitoneally administered pentobarbital sodium. The left femoral region was then incised and 0.1 ml of 5% lactic acid solution was administered into the femoral artery. Adhesives were applied dropwise at the lactic acid administered site for blood stanching. Thereafter, a penicillin G solution was added dropwise to prevent infections and the incised part was sutured. Test compound ID3016511, which is a white powder and has poor solubility in water, was suspended in an aqueous solution of 0.5% carboxymethylcellulose sodium (0.5% CMC-Na) and test solutions of a maximal dosage of 60 mg/S ml/kg (body weight) and a low dosage of 20 mg/S ml/kg (body weight) were prepared. The solvent and the test solution were orally administered. Administration was carried out 2 hours before lactic acid administration and, thereafter, twice a day at an interval of at least 7 hours for 13 days repeatedly. Ticlopidine (Sigma) at the dosage of 300 mg/5 ml/kg (body weight) was used as a positive control material with the aid of an aqueous solution of 0.5% CMC-Na. The positive control material was administered 3 hours before the lactic acid administration, and it was repeatedly orally administered twice a day for 13 days in the same way as the above test compound. The progress of lesion on legs and feet was observed 3, 7, and 14 days after the lactic acid administration and the results were scored from 0 to 4 based on the following criteria:

(Scores)

0: no lesion

1: nigrities limited to the tiptoe

2: nigrities reaching toe

3: necrosis of toe

4: exfoliation of toe

Each toe was scored and the sum of scores for each toe was determined as a lesion index. When the damage reached the sole, 5 points were added.

The results of this test are shown in Table 3. The test results are indicated by the average±the standard error. The significant difference between the control group and the test material group was assayed by the non-parametric Dunnet's test. The significant difference between the control group and the positive control material group was assayed by the non-parametric Wilcoxon's test. The lesion index of the control group was 2.5±0.5 at three days after lactic acid administration, 4.3±0.9 at seven days after the administration, and 7.7±1.5 at fourteen days after the administration. In the group of repeated administration of 20 mg/kg of ID3016511 for 14 days, the equivalent level of progress with the control group was observed in the lesion. In the group of repeated administration of 60 mg/kg of ID3016511, an inhibitory tendency in the lesion index began to be exhibited 3 days after lactic acid administration and the lesion index was significantly inhibited 14 days after lactic acid administration. A single dose of 300 mg/kg of ticlopidine, which was a positive control material, significantly inhibited the lesion index from 3 days after lactic acid administration.

As is apparent from the above results, the compound ID3016511 (Compound 115) according to the present invention inhibited the progress of lesions in the feet and legs at the dose of 60 mg/kg. Other compounds shown in Table 1, which are structurally similar with Compound 115, are considered to exhibit similar actions.

TABLE 3

Effects of ID3016511 and ticlopidine on lactic acid induced peripheral circulatory disturbance in rats

| Drug | Dosage (mg/kg, twice/day) | Number of animals | Score of lesion — Number of days after lactic acid injection | | |
|---|---|---|---|---|---|
| | | | 3 | 7 | 14 |
| Control [a] | | 10 | 2.5 ± 0.5 | 4.3 ± 0.9 | 7.7 ± 1.5 |
| ID3016511 | 20 | 10 | 2.6 ± 0.8 | 4.3 ± 1.0 | 6.9 ± 1.4 |
| | 60 | 10 | 1.1 ± 0.4 | 1.9 ± 0.5 | 3.2 ± 0.7* |
| Ticlopidine [b] | 300 | 10 | 0.4 ± 0.2## | 1.2 ± 0.4# | 1.6 ± 0.4## |

[a] 0.5% CMC-Na (5 ml/kg, p.o.)
[b] Ticlopidine was administered once 3 hours after the lactic acid treatment. Each value represents the mean ± S.E.
*Significant difference from the control ($P < 0.05$) (non-parametric Dunnett's test)
# and ## Significant difference from the control ($P < 0.05$ and $P < 0.01$, respectively) (Wilcoxon's test)

Example 174

Assay of Inhibitory Activity Against the BrdU Incorporation

Figure 2A:
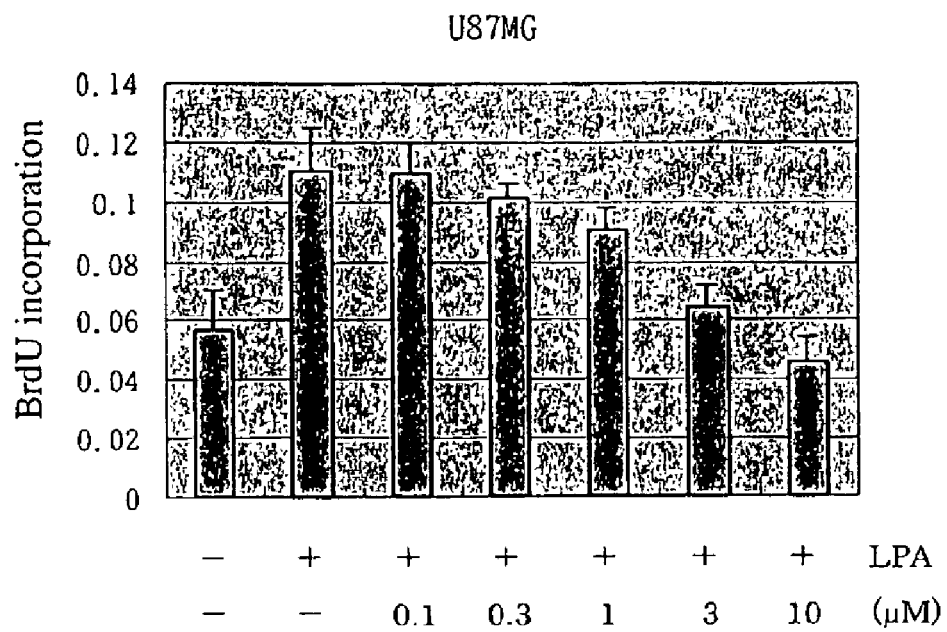
FIG. 2A and FIG. 2B show the inhibitory action of Compound 115 against the proliferation of cultured carcinoma cells by LPA.
Figure 2B:
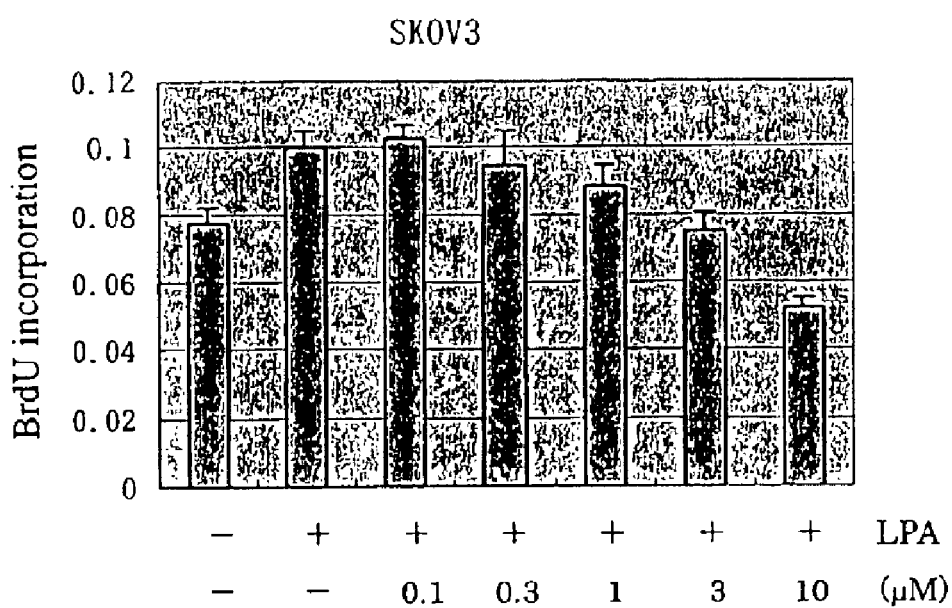

Human brain tumor cells (U87 MG) and ovarian carcinoma cells (SKOV3) suspended in serum-free DMEM were plated on a 96-well plate. 24 hours later, Compound 115 and LPA (3 $\mu$M) were added and the mixture was cultured for 16 hours, followed by the BrdU addition. Culture was continued for 3 hours from the addition of BrdU. Thereafter, the incorporation of BrdU into the cells was assayed based on the absorbance at 450 nm using the Cell proliferation ELISA system (RPN250, Amersham LIFE SCIENCE). The results thereof are shown in FIGS. 2A and 2B.

As is apparent from these figures, Compound 115 inhibited the proliferation of carcinoma cells in a concentration dependent manner at a concentration of 0.3 $\mu$M or higher.

Industrial Applicability

The present invention provides a formulation comprising an azole compound having an antagonistic action on an LPA receptor and a pharmaceutically acceptable salt thereof. The formulation exhibits excellent preventive and therapeutic properties against restenosis after percutaneous transluminal coronary angioplasty (PTCA), arteriosclerosis, artery obstruction, malignant and benign proliferative diseases, various inflammatory diseases, kidney diseases, proliferation of tumor cells, carcinoma invasion/metastasis, brain or periphery nerve disorders and the like.

The present invention has been described with reference to specific examples in the above. The present invention is, however, not limited to the above examples and various changes and modification should be construed as possible as long as they are within the range of equivalence not departing from the idea and the scope of the present invention as set forth in the accompanying claims. Various literatures cited herein (including patents and patent applications) are incorporated by reference in their entirety.

What is claimed is:

1. A compound represented by general formula [1] or salt thereof:

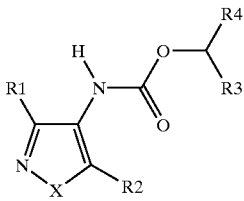

[1]

wherein

R1 is a halogen atom or lower alkyl optionally substituted by one or more substituents independently selected from: (I) alkyloxy, (II) alkylthio, (III) alkylamino, (IV) cyano, (V) nitro, (VI) cyclic amino, and (VII) a halogen atom; and R2 is an optionally substituted aryl or aromatic heterocycle;

R3 represents a hydrogen atom, lower alkyl, or alkyl halide;

R4 represents a group selected from (I) optionally substituted phenyl, aryl, or heterocycle, (II) substituted or nonsubstituted alkyl, and (III) substituted or nonsubstituted alkenyl, alternatively, R3 and R4 may form a five- to ten-membered cyclic structure together with a carbon atom to which they bind; and X represents an oxygen atom or a sulfur atom, provided that, when R3 is a hydrogen atom, then R4 represents a group other than methyl.

2. A compound represented by general formula [1] or salt thereof:

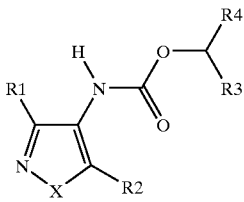

[1]

wherein

R1 is an optionally substituted aryl or aromatic heterocycle; and

R2 is a halogen atom or lower alkyl optionally substituted by one or more substituents independently selected from (I) alkyloxy, (II) alkylthio, (III) alkylamino, (IV) cyano, (V) nitro, (VI) cyclic amino, and (VII) a halogen atom;

R3 represents a hydrogen atom, lower alkyl, or alkyl halide;

R4 represents a group selected from (I) optionally substituted phenyl, aryl, or heterocycle, (II) substituted or nonsubstituted alkyl, and (III) substituted or nonsubstituted alkenyl, alternatively, R3 and R4 may form a five- to ten-membered cyclic structure together with a carbon atom to which they bind; and X represents an oxygen atom or a sulfur atom, provided that, when R3 is a hydrogen atom, then R4 represents a group other than methyl.

3. The compound or salt thereof according to claim 1, wherein X is an oxygen atom.

4. The compound or salt thereof according to claim 1, wherein the compound is represented by general formula [2]:

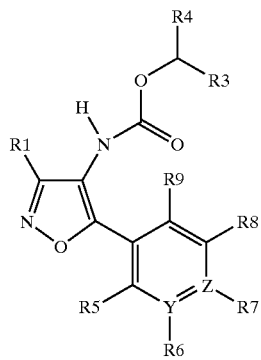

[2]

wherein

R1, R3, and R4 are as defined in claim 2;

Y and Z are each independently a carbon atom or a nitrogen atom; and

R5, R6, R7, R8, and R9 are each independently a group selected from (I) a hydrogen atom;

(II) a halogen atom;

(III) lower alkyl optionally substituted by one or more substituents independently selected from: (1) hydroxy, (2) amino, (3) alkyloxy, (4) alkylthio, (5) alkylsulfinyl, (6) alkylsulfonyl, (7) monoalkylamino or dialkylamino, (8) acyloxy, (9) acylamino, (10) aryloxy, (11) arylthio, (12) arylsulfinyl, (13) arylsulfonyl, (14) arylamino, (15) alkylsulfonylamino or arylsulfonylamino, (16) alkylureide or arylureide, (17) alkyloxycarbonylamino or aryloxycarbonylamino, (18) alkylaminocarbonyloxy or arylaminocarbonyloxy, (19) cyano, (20) cyclic amino, and (21) a halogen atom;

(IV) optionally halogenated alkyloxy, (V) cycloalkyl, (VI) aryl, (VII) aryloxy, (VIII) acylamino, (IX) acyloxy, (X) hydroxy, (XI) nitro, (XII) cyano, (XIII) amino, (XIV) monoalkylamino or dialkylamino, (XV) arylamino, (XVI) alkylsulfonylamino or arylsulfonylamino, (XVII) alkylureide or arylureide, (XVIII) alkyloxycarbonylamino or aryloxycarbonylamino, (XIX) alkylaminocarbonyloxy or arylaminocarbonyloxy, (XX) alkyloxycarbonyl or aryloxycarbonyl, (XXI) acyl, (XXII) carboxyl, (XXIII) carbamoyl, (XXIV) monoalkylcarbamoyl or dialkylcarbamoyl, (XXV) cyclic amino, and (XXVI) alkylsulfonyl or arylsulfonyl, provided that, when Y is a nitrogen atom, R6 is absent, and Z is a nitrogen atom, then R7 is absent.

5. The compound or salt thereof according to claim 1, wherein

R1 is methyl or ethyl;

R3 is a hydrogen atom, methyl, or trifluoromethyl;

R4 is phenyl optionally substituted by one or more substituents independently selected from a halogen atom, optionally halogenated lower alkyl, optionally halogenated alkyloxy, optionally halogenated alkylthio, cycloalkyl, aryl, aryloxy, acylamino, acyloxy, hydroxy, nitro, cyano, amino, monoalkylamino, dialkylamino, arylamino, alkylsulfonylamino, arylsulfonylamino, alkylureide, arylureide, alkyloxycarbonylamino, aryloxycarbonylamino, alkylaminocarbonyloxy, arylaminocarbonyloxy, alkyloxycarbonyl, aryloxycarbonyl, acyl, carboxyl, carbamoyl, monoalkylcarbamoyl, dialkylcarbamoyl, cyclic amino, and alkylsulfonyl and arylsulfonyl;

R2 is a group represented by the following formula:

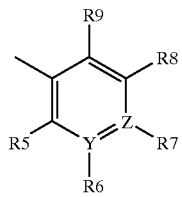

Y and Z are each a carbon atom; and

R5, R8, and R9 are each independently a group selected from
(I) a hydrogen atom;
(II) a halogen atom;
(III) lower alkyl optionally substituted by one or more substituents independently selected from: (1) hydroxy, (2) amino, (3) alkyloxy, (4) alkylthio, (5) alkylsulfinyl, (6) alkylsulfonyl, (7) monoalkylamino or dialkylamino, (8) acyloxy, (9) acylamino, (10) aryloxy, (11) arylthio, (12) arylsulfinyl, (13) arylsulfonyl, (14) arylamino, (15) alkylsulfonylamino or arylsulfonylamino, (16) alkylureide or arylureide, (17) alkyloxycarbonylamino or aryloxycarbonylamino, (18) alkylaminocarbonyloxy or arylaminocarbonyloxy, (19) cyano, (20) cyclic amino, and (21) a halogen atom;
(IV) optionally halogenated alkyloxy, (V) cycloalkyl, (VI) aryl, (VII) aryloxy, (VIII) acylamino, (IX) acyloxy, (X) hydroxy, (XI) nitro, (XII) cyano, (XIII) amino, (XIV) monoalkylamino or dialkylamino, (XV) arylamino, (XVI) alkylsulfonylamino or arylsulfonylamino, (XVII) alkylureide or arylureide, (XVIII) alkyloxycarbonylamino or aryloxycarbonylamino, (XIX) alkylaminocarbonyloxy or arylaminocarbonyloxy, (XX) alkyloxycarbonyl or aryloxycarbonyl, (XXI) acyl, (XXII) carboxyl, (XXIII) carbamoyl, (XXIV) monoalkylcarbamoyl or dialkylcarbamoyl, (XXV) cyclic amino, and (XXVI) alkylsulfonyl or arylsulfonyl, and R6 and R7 are each independently a hydrogen atom, a halogen atom, chloromethyl, hydroxymethoxy, cyano, trifluoromethoxy, a group represented by formula [3]:

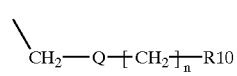

wherein
n is 0 to 5;
Q is an oxygen atom, a sulfur atom, sulfinyl, or sulfonyl; and
R10 is a group selected from a hydrogen atom, a halogen atom, alkyl, alkyloxy, alkylthio, monoalkylamino, dialkylamino, aryloxy, arylthio, cyano, nitro, carboxyl, alkyloxycarbonyl, aryloxycarbonyl, carbamoyl, monoalkylcarbamoyl, dialkylcarbamoyl, acyl, aryl, cyclic amino, and heterocycle, or a group represented by formula [4]:

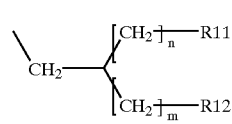

wherein
n and m are each 0 to 5; and
R11 and R12 are each independently a group selected from a hydrogen atom, a halogen atom, alkyl, alkyloxy, alkylthio, monoalkylamino or dialkylamino, aryloxy, arylthio, hydroxy, cyano, nitro, carboxyl, alkyloxycarbonyl or aryloxycarbonyl, carbamoyl, monoalkylcarbamoyl or dialkylcarbamoyl, acyl, aryl, cyclic amino, and heterocycle; or R11 and R12 may together form a five- to nine-membered heterocycle containing, in addition to a nitrogen atom, 1 to 3 oxygen atoms or sulfur atoms.

6. The compound or salt thereof according to claim 2, wherein the compound is represented by general formula [5]:

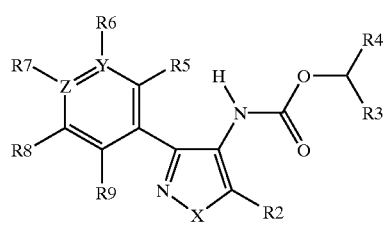

wherein
R2, R3, and R4 are as defined in claim 3;
Y and Z are each independently a carbon atom or a nitrogen atom;
R5, R6, R7, R8, and R9 are each independently selected from:
(I) a hydrogen atom;
(II) a halogen atom;
(III) lower alkyl optionally substituted by one or more substituents independently selected from (1) hydroxy, (2) amino, (3) alkyloxy, (4) alkylthio, (5) alkylsulfinyl, (6) alkylsulfonyl, (7) monoalkylamino or dialkylamino, (8) acyloxy, (9) acylamino, (10) aryloxy, (11) arylthio, (12) arylsulfinyl, (13) arylsulfonyl, (14) arylamino, (15) alkylsulfonylamino or arylsulfonylamino, (16) alkylureide or arylureide, (17) alkyloxycarbonylamino or aryloxycarbonylamino, (18) alkylaminocarbonyloxy or arylaminocarbonyloxy, (19) cyano, (20) cyclic amino, and (21) a halogen atom;
(IV) optionally halogenated alkyloxy; (V) cycloalkyl; (VI) aryl; (VII) aryloxy; (VIII) acylamino; (IX) acyloxy; (X) hydroxy; (XI) nitro; (XII) cyano; (XIII) amino; (XIV) monoalkylamino or dialkylamino; (XV) arylamino; (XVI) alkylsulfonylamino or arylsulfonylamino; (XVII) alkylureide or arylureide; (XVIII) alkyloxycarbonylamino or aryloxycarbonylamino; (XIX)

alkylaminocarbonyloxy or arylaminocarbonyloxy; (XX) alkyloxycarbonyl or aryloxycarbonyl; (XXI) acyl; (XXII) carboxyl; (XXIII) carbamoyl; (XXIV) monoalkylcarbamoyl or dialkylcarbamoyl; (XXV) cyclic amino; and (XXVI) alkylsulfonyl or arylsulfonyl;

provided that, when Y is a nitrogen atom, R6 is absent, and Z is a nitrogen atom, then R7 is absent.

7. The compound or salt thereof according to claim 2, wherein

R2 is methyl or ethyl;

R3 is a hydrogen atom, methyl, or trifluoromethyl;

R4 is phenyl optionally substituted by one or more substituents independently selected from a halogen atom, optionally halogenated lower alkyl, optionally halogenated alkyloxy, optionally halogenated alkylthio, cycloalkyl, aryl, aryloxy, acylamino, acyloxy, hydroxy, nitro, cyano, amino, monoalkylamino, dialkylamino, arylamino, alkylsulfonylamino, arylsulfonylamino, alkylureide, or arylureide, alkyloxycarbonylamino, aryloxycarbonylamino, alkylaminocarbonyloxy, arylaminocarbonyloxy, alkyloxycarbonyl, aryloxycarbonyl, acyl, carboxyl, carbamoyl, monoalkylcarbamoyl, dialkylcarbamoyl, cyclic amino, alkylsulfonyl and arylsulfonyl;

R1 is a group represented by the following formula:

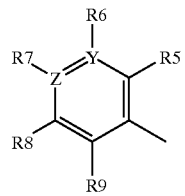

Y and Z are each independently a carbon atom; and

R5, R8, and R9 are each independently a group selected from:

(I) a hydrogen atom;

(II) a halogen atom;

(III) lower alkyl optionally substituted by one or more substituents independently selected from (1) hydroxy, (2) amino, (3) alkyloxy, (4) alkylthio, (5) alkylsulfinyl, (6) alkylsulfonyl, (7) monoalkylamino or dialkylamino, (8) acyloxy, (9) acylamino, (10) aryloxy, (11) arylthio, (12) arylsulfinyl, (13) arylsulfonyl, (14) arylamino, (15) alkylsulfonylamino or arylsulfonylamino, (16) alkylureide or arylureide, (17) alkyloxycarbonylamino or aryloxycarbonylamino, (18) alkylaminocarbonyloxy or arylaminocarbonyloxy, (19) cyano, (20) cyclic amino, and (21) a halogen atom;

(IV) optionally halogenated alkyloxy; (V) cycloalkyl; (VI) aryl; (VII) aryloxy; (VIII) acylamino; (IX) acyloxy; (X) hydroxy; (XI) nitro; (XII) cyano; (XIII) amino; (XIV) monoalkylamino or dialkylamino; (XV) arylamino; (XVI) alkylsulfonylamino or arylsulfonylamino; (XVII) alkylureide or arylureide; (XVIII) alkyloxycarbonylamino or aryloxycarbonylamino; (XIX) alkylaminocarbonyloxy or arylaminocarbonyloxy; (XX) alkyloxycarbonyl or aryloxycarbonyl; (XXI) acyl; (XXII) carboxyl; (XXIII) carbamoyl; (XXIV) monoalkylcarbamoyl or dialkylcarbamoyl; (XXV) cyclic amino; and (XXVI) alkylsulfonyl or arylsulfonyl; and R6 and R7 are each independently a hydrogen atom, a halogen atom, chloromethyl, hydroxymethyl, cyano, trifluoromethoxy, or a group represented by formula [3]:

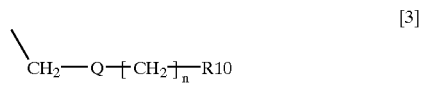

wherein n is 0 to 5;

Q is an oxygen atom, a sulfur atom, sulfinyl, or sulfonyl; and

R10 is a group selected from a hydrogen atom, a halogen atom, alkyl, alkyloxy, alkylthio, monoalkylamino, dialkylamino, aryloxy, arylthio, cyano, nitro, carboxyl, alkyloxycarbonyl, aryloxycarbonyl, carbamoyl, monoalkylcarbamoyl, dialkylcarbamoyl, acyl, aryl, cyclic amino, and heterocycle, or a group represented by formula [4]:

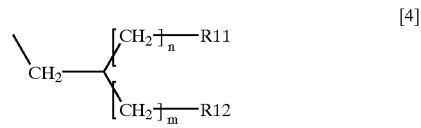

wherein n and m are each 0 to 5; and

R11 and R12 are each independently a group selected from a hydrogen atom, a halogen atom, alkyl, alkyloxy, alkylthio, monoalkylamino, dialkylamino, aryloxy, arylthio, hydroxy, cyano, nitro, carboxyl, alkyloxycarbonyl, aryloxycarbonyl, carbamoyl, monoalkylcarbamoyl, dialkylcarbamoyl, acyl, aryl, cyclic amino, and heterocycle; or R11 and R12 may together form a five- to nine-membered heterocycle containing, in addition to a nitrogen atom, 1 to 3 oxygen atoms or sulfur atoms.

8. The compound or salt thereof according to claim 4, wherein

R4 is phenyl optionally substituted by one or more substituents independently selected from a halogen atom, optionally halogenated lower alkyl, optionally halogenated alkyloxy, optionally halogenated alkylthio, acylamino, hydroxy, nitro, cyano, amino, monoalkylamino, dialkylamino, alkyloxycarbonyl, aryloxycarbonyl, acyl, carboxyl, and cyclic amino.

9. The compound or salt thereof according to claim 4, wherein R4 is nonsubstituted phenyl, 2-chlorophenyl, 2-bromophenyl, or 2-fluorophenyl.

10. The compound or salt thereof according to claim 2, wherein X is an oxygen atom.

11. The compound or salt thereof according to claim 5, wherein

R4 is phenyl optionally substituted by one or more substituents independently selected from a halogen atom, optionally halogenated lower alkyl, optionally halogenated alkyloxy, optionally halogenated alkylthio, acylamino, hydroxy, nitro, cyano, amino, monoalkylamino, dialkylamino, alkyloxycarbonyl, aryloxycarbonyl, acyl, carboxyl, and cyclic amino.

12. The compound or salt thereof according to claim 6, wherein

R4 is phenyl optionally substituted by one or more substituents independently selected from a halogen atom, optionally halogenated lower alkyl, optionally halogenated alkyloxy, optionally halogenated alkylthio, acylamino, hydroxy, nitro, cyano, amino, monoalkylamino, dialkylamino, alkyloxycarbonyl, aryloxycarbonyl, acyl, carboxyl, and cyclic amino.

13. The compound or salt thereof according to claim 7, wherein

R4 is phenyl optionally substituted by one or more substituents independently selected from a halogen atom, optionally halogenated lower alkyl, optionally halogenated alkyloxy, optionally halogenated alkylthio, acylamino, hydroxy, nitro, cyano, amino, monoalkylamino, dialkylamino, alkyloxycarbonyl, aryloxycarbonyl, acyl, carboxyl, and cyclic amino.

14. The compound or salt thereof according to claim 5, wherein R4 is nonsubstituted phenyl, 2-chlorophenyl, 2-bromophenyl, or 2-fluorophenyl.

15. The compound or salt thereof according to claim 6, wherein R4 is nonsubstituted phenyl, 2-chlorophenyl, 2-bromophenyl, or 2-fluorophenyl.

16. The compound or salt thereof according to claim 7, wherein R4 is nonsubstituted phenyl, 2-chlorophenyl, 2-bromophenyl, or 2-fluorophenyl.

17. The compound or salt thereof according to claim 1, wherein

R1 is methyl or ethyl;

R3 is a hydrogen atom, methyl, or trifluoromethyl;

R4 is phenyl optionally substituted by one or more substituents independently selected from a halogen atom, optionally halogenated lower alkyl, optionally halogenated alkyloxy, optionally halogenated alkylthio, cycloalkyl, aryl, aryloxy, acylamino, acyloxy, hydroxy, nitro, cyano, amino, monoalkylamino, dialkylamino, arylamino, alkylsulfonylamino, arylsulfonylamino, alkylureide, arylureide, alkyloxycarbonylamino, aryloxycarbonylamino, alkylaminocarbonyloxy, arylaminocarbonyloxy, alkyloxycarbonyl, aryloxycarbonyl, acyl, carboxyl, carbamoyl, monoalkylcarbamoyl, dialkylcarbamoyl, cyclic amino, alkylsulfonyl and arylsulfonyl;

R2 is a group represented by the following formula:

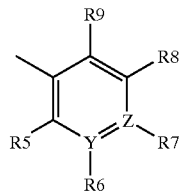

Y and Z are each a carbon atom;

R5, R8, and R9 are each independently a group selected from (I) a hydrogen atom;

(II) a halogen atom;

(III) lower alkyl optionally substituted by one or more substituents independently selected from: (1) hydroxy, (2) amino, (3) alkyloxy, (4) alkylthio, (5) alkylsulfinyl, (6) alkylsulfonyl, (7) monoalkylamino or dialkylamino, (8) acyloxy, (9) acylamino, (10) aryloxy, (11) arylthio, (12) arylsulfinyl, (13) arylsulfonyl, (14) arylamino, (15) alkylsulfonylamino or arylsulfonylamino, (16) alkylureide or arylureide, (17) alkyloxycarbonylamino or aryloxycarbonylamino, (18) alkylaminocarbonyloxy or arylaminocarbonyloxy, (19) cyano, (20) cyclic amino, and (21) a halogen atom; and (IV) optionally halogenated alkyloxy, (V) cycloalkyl, (VI) aryl, (VII) aryloxy, (VIII) acylamino, (IX) acyloxy, (X) hydroxy, (XI) nitro, (XII) cyano, (XIII) amino, (XIV) monoalkylamino or dialkylamino, (XV) arylamino, (XVI) alkylsulfonylamino or arylsulfonylamino, (XVII) alkylureide or arylureide, (XVIII) alkyloxycarbonylamino or aryloxycarbonylamino, (XIX) alkylaminocarbonyloxy or arylaminocarbonyloxy, (XX) alkyloxycarbonyl or aryloxycarbonyl, (XXI) acyl, (XXII) carboxyl, (XXIII) carbamoyl, (XXIV) monoalkylcarbamoyl or dialkylcarbamoyl, (XXV) cyclic amino, and (XXVI) alkylsulfonyl or arylsulfonyl, and R6 and R7 are each independently a hydrogen atom, a halogen atom, chloromethyl, hydroxymethyl, cyano, trifluoromethoxy, or a group represented by formula [3]:

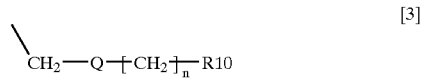

wherein n is 0 to 5;

Q is an oxygen atom, a sulfur atom, sulfinyl, or sulfonyl; and

R10 is a group selected from a hydrogen atom, a halogen atom, alkyl, alkyloxy, alkylthio, monoalkylamino, dialkylamino, aryloxy, arylthio, cyano, nitro, carboxyl, alkyloxycarbonyl, aryloxycarbonyl, carbamoyl, monoalkylcarbamoyl, dialkylcarbamoyl, acyl, aryl, optionally halogenated or alkylated aryl, cyclic amino, optionally halogenated or alkylated heterocycle, carboxylalkylcarbamoyl, monohydroxyalkyl, dihydroxyalkyl, monoalkylaminocarbonyl, dialkylaminocarbonyl, heterocyclylalkylaminocarbonyl, alkylcarbonylamino, alkylcarbonyl, sulfonic acid, alkenyl, carboxylalkylcarbamoylalkyl, caboxylalkyl, 2-amino-2-alkoxycarbonylalkyl and heterocyclylcarbonylamino, or a group represented by formula [4]:

wherein

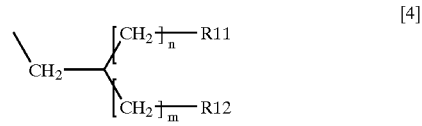

n and m are each 0 to 5; and

R11 and R12 are each independently a group selected from a hydrogen atom, a halogen atom, alkyl, alkyloxy, alkylthio, monoalkylamino, dialkylamino, aryloxy, arylthio, hydroxy, cyano, nitro, carboxyl, alkyloxycarbonyl, aryloxycarbonyl, carbamoyl, monoalkylcarbamoyl, dialkylcarbamoyl, acyl, optionally halogenated or alkylated aryl, cyclic amino, and optionally halogenated or alkylated heterocycle; or R11 and R12 may together form a five- to nine-membered optionally halogenated or alkylated heterocycle containing, in addition to a nitrogen atom, 1 to 3 oxygen atoms or sulfur atoms.

18. A compound selected from:

3-Furylmethyl N-(5-methyl-3-phenyl-4-isoxazolyl) carbamate;
Benzyl N-(5-methyl-3-phenyl-4-isoxazolyl)carbamate;
1-(2-Chlorophenyl)ethyl N-(3-methyl-5-phenyl-4-isoxazolyl)carbamate;
1-(2-Chlorophenyl)ethyl N-(5-methyl-3-phenyl-4-isoxazolyl)carbamate;
1-(2-Chlorophenyl)ethyl N-[5-methyl-3-(4-methylphenyl)-4-isoxazolyl]carbamate;
1-(2-Chlorophenyl)ethyl N-[5-methyl-3-(4-nitrophenyl)-4-isoxazolyl]carbamate;
Benzyl N-(3-methyl-5-phenyl-4-isoxazolyl)carbamate;
1-(2-Chlorophenyl)ethyl N-[3-[4-(hydroxymethyl)phenyl]-5-methyl-4-isoxazolyl]carbamate;
(1R)-1-Phenylethyl N-(5-methyl-3-phenyl-4-isoxazolyl) carbamate;
(1S)-1-Phenylethyl N-(5-methyl-3-phenyl-4-isoxazolyl) carbamate;
1-(2-Chlorophenyl)ethyl N-[5-methyl-3-[4-(trifluoromethoxy)phenyl]-4-isoxazolyl]carbamate;
1-Phenylethyl N-(5-methyl-3-phenyl-4-isoxazolyl) carbamate;
1-(2-Chlorophenyl)ethyl N-[3-(3-bromophenyl)-5-methyl-4-isoxazoly]carbamate;
1-(2-Methylphenyl)ethyl N-(5-methyl-3-phenyl-4-isoxazolyl)carbamate; 1-(2-Chlorophenyl)ethyl N-[5-methyl-3-[3-(trifluoromethyl)phenyl]-4-isoxazolyl] carbamate;
1-(2-Chlorophenyl)ethyl N-[3-(4-fluorophenyl)-5-methyl-4-isoxazolyl]carbamate;
(1R)-1-(2-Chlorophenyl)ethyl N-(5-methyl-3-phenyl-4-isoxazolyl)carbamate;
(1R)-1-(2-Chlorophenyl)ethyl N-(3-methyl-5-phenyl-4-isoxazolyl)carbamate;
1-(2-Fluorophenyl)ethyl N-(5-methyl-3-phenyl-4-isoxazolyl)carbamate;
1-(2-Chlorophenyl)ethyl N-[3-(2-fluorophenyl)-5-methyl-4-isoxazolyl]carbamate;
1-(2-Chlorophenyl)ethyl N-[3-(3-fluorophenyl)-5-methyl-4-isoxazolyl]carbamate;
(1R)-1-(2-Bromophenyl)ethyl N-(5-methyl-3-phenyl-4-isoxazolyl)carbamate;
1-(2-Bromophenyl)ethyl N-(5-methyl-3-phenyl-4-isoxazolyl)carbamate;
(1R)-1-(2-Bromophenyl)ethyl N-[3-chloro-5-(2-chlorophenyl)-4-isothiazolyl]carbamate;
1-Phenylethyl N-[3-chloro-5-(2-chlorophenyl)-4-isothiazolyl]carbamate;
1-(2-Fluorophenyl)ethyl N-[3-chloro-5-(2-chlorophenyl)-4-isothiazolyl]carbamate;
1-Phenylethyl N-[3-methyl-5-(3-methylphenyl)-4-isoxazolyl]carbamate;
1-(2-Chlorophenyl)ethyl N-[3-methyl-5-(3-methylphenyl)-4-isoxazoly]carbamate;
1-Phenylethyl N-(5-(3-fluorophenyl)-3-methyl-4-isoxazolyl]carbamate;
1-(2-Chlorophenyl)ethyl N-[5-(3-fluorophenyl)-3-methyl-4-isoxazolyl]carbamate;
1-Phenylethyl N-[5-(2-furyl)-3-methyl-4-isoxazolyl] carbamate;
1-(2-Chlorophenyl)ethyl N-[5-(2-furyl)-3-methyl-4-isoxazolyl]carbamate;
(1R)-1-(2-Bromophenyl)ethyl N-[5-(3-fluorophenyl)-3-methyl-4-isoxazolyl]carbamate;
1-(2-Fluorophenyl)ethyl N-[5-(3-fluorophenyl)-3-methyl-4-isoxazolyl]carbamate;
1-Phenylethyl N-[5-[4-(trifluoromethoxy)phenyl]-3-methyl-4-isoxazoly]carbamate;
1-(2-Chlorophenyl)ethyl N-[5-[4-(trifluoromethoxy)phenyl]-3-methyl-4-isoxazolyl]carbamate;
1-Phenylethyl N-[3-methyl-5-(4-methylphenyl)-4-isoxazolyl]carbamate;
1-(2-Chlorophenyl)ethyl N-[3-methyl-5-(4-methylphenyl)-4-isoxazolyl]carbamate;
1-(2-Chlorophenyl)ethyl N-[5-(3-chlorophenyl )-3-methyl-4-isoxazolyl]carbamate;
1-Phenylethyl N-[5-(4-fluorophenyl)-3-methyl-4-isoxazolyl]carbamate;
1-(2-Chlorophenyl)ethyl N-[5-(4-fluorophenyl )-3-methyl-4-isoxazolyl]carbamate;
1-Phenylethyl N-[5-(2-fluorophenyl)-3-methyl-4-isoxazolyl]carbamate;
1-(2-Chlorophenyl)ethyl N-[5-(2-fluorophenyl)-3-methyl-4-isoxazolyl]carbamate;
(1R)-1-(2-Bromophenyl)ethyl N-[3-methyl-5-[4-(trifluoromethoxy)phenyl]-4-isoxazolyl]carbamate;
1-(2-Fluorophenyl)ethyl N-[3-methyl-5-[4-(trifluoromethoxy)phenyl]-4-isoxazolyl]carbamate;
1-Phenylethyl N-[5-(4-cyanophenyl)-3-methyl-4-isoxazolyl]carbamate;
1-(2-Chlorophenyl)ethyl N-[5-(4-cyanophenyl)-3-methyl-4-isoxazolyl]carbamate;
(1R)-1-(2-Bromophenyl)ethyl N-[3-methyl-5-(4-methylphenyl)-4-isoxazolyl]carbamate;
1-(2-Fluorophenyl)ethyl N-[3-methyl-5-(4-methylphenyl)-4-isoxazolyl]carbamate;
1-(2-Chlorophenyl)ethyl N-[5-(4-methoxyphenyl)-3-methyl-4-isoxazolyl]carbamate;
1-(2-Chlorophenyl)ethyl N-[5-(2-bromophenyl)-3-methyl-4-isoxazolyl]carbamate;
1-(2-Chlorophenyl)ethyl N-[5-(1,3-benzodioxol-5-yl)-3-methyl-4-isoxazolyl]carbamate;
1-(2-Chlorophenyl)ethyl N-[3-methyl-5-[3-(trifluoromethoxy)phenyl]-4-isoxazolyl]carbamate;
1-Phenylethyl N-[3-methyl-5-(4-nitrophenyl)-4-isoxazolyl]carbamate;
1-(2-Chlorophenyl)ethyl N-[3-methyl-5-(4-nitrophenyl)-4-isoxazolyl]carbamate;
1-Phenylethyl N-[3-methyl-5-(2-thienyl)-4-isoxazolyl] carbamate;
1-(2-Chlorophenyl)ethyl N-[3-methyl-5-(2-thienyl)-4-isoxazolyl]carbamate;
1-Phenylethyl N-[3-methyl-5-(3-nitrophenyl)-4-isoxazolyl]carbamate;
1-(2-Chlorophenyl)ethyl N-[3-methyl-5-(3-nitrophenyl)-4-isoxazolyl]carbamate;
1-(2-Chlorophenyl)ethyl N-[5-(2,4-difluorophenyl)-3-methyl-4-isoxazolyl]carbamate;
1-Phenylethyl N-[3-methyl-5-(4-pyridyl)-4-isoxazolyl] carbamate;

1-(2-Chlorophenyl)ethyl N-[3-methyl-5-(4-pyridyl)-4-isoxazoly]carbamate;
1-(2-Chlorophenyl)ethyl N-[5-(6-chloro-3-pyridyl)-3-methyl-4-isoxazolyl]carbamate;
1-Phenylethyl N-[5-(4-butylphenyl)-3-methyl-4-isoxazolyl]carbamate;
1-(2-Chlorophenyl)ethyl N-[5-(4-butylphenyl)-3-methyl-4-isoxazolyl]carbamate;
1-Phenylethyl N-[3-methyl-5-(3-methyl-2-thienyl)-4-isoxazolyl]carbamate;
1-(2-Chlorophenyl)ethyl N-[3-methyl-5-(3-methyl-2-thienyl)-4-isoxazolyl]carbamate;
1-(2-Chlorophenyl)ethyl N-[5-(3-furyl)-3-methyl-4-isoxazolyl]carbamate;
1-(2-Chlorophenyl)ethyl N-[3-methyl-5-(5-methyl-2-thienyl)-4-isoxazolyl]carbamate;
1-(2-Chlorophenyl)ethyl N-[5-[3-(chloromethyl)phenyl]-3-methyl-4-isoxazolyl]carbamate;
1-(2-Chlorophenyl)ethyl N-[5-(2-chloro-4-pyridyl)-3-methyl-4-isoxazolyl]carbamate;
1-(2-Chlorophenyl)ethyl N-[5-(3-phenyl-5-methyl-4-isoxazolyl)-3-methyl-4-isoxazolyl]carbamate;
1-(2-Chlorophenyl)ethyl N-[5-(5-bromo-2-furyl)-3-methyl-4-isoxazolyl]carbamate;
1-(2-Chlorophenyl)ethyl N-[5-[4-(chloromethyl)phenyl]-3-methyl-4-isoxazolyl]carbamate;
1-(2-Chlorophenyl)ethyl N-[3-methyl-5-(3-thienyl)-4-isoxazolyl]carbamate;
1-(2-Chlorophenyl)ethyl N-(3-ethyl-5-phenyl-4-isoxazolyl)carbamate;
1-(2-Chlorophenyl)ethyl N-[5-(4-cyanophenyl)-3-ethyl-4-isoxazolyl]carbamate;
1-(2-Chlorophenyl)ethyl N-[3-(methoxymethyl)-5-phenyl-4-isoxazolyl]carbamate;
1-(2-Chlorophenyl)ethyl N-[3-methyl-5-[4-(phenoxymethyl)phenyl]-4-isoxazolyl]carbamate;
2,2,2-Trifluoro-1-phenylethyl N-(5-methyl-3-phenyl-4-isoxazolyl)carbamate;
1-Phenylallyl N-(5-methyl-3-phenyl-4-isoxazolyl)carbamate;
1-(2-Chlorophenyl)ethyl N-[5-(4-[[(4-fluorobenzyl)oxy]methyl]phenyl)-3-methyl-4-isoxazolyl]carbamate;
1-(2-Chlorophenyl)ethyl N-[5-(4-[[(2,6-difluorobenzyl)oxy]methyl]phenyl)-3-methyl-4-isoxazolyl]carbamate;
1-(2-Chlorophenyl)ethyl N-(5-[4-[(2-furylmethoxy)methyl]phenyl]-3-methyl-4-isoxazolyl)carbamate;
1-(2-Chlorophenyl)ethyl N-(5-[4-[(3-furylmethoxy)methyl]phenyl]-3-methyl-4-isoxazolyl)carbamate;
2,2,2-Trifluoro-1-phenylethyl N-[5-(4-cyanophenyl)-3-methyl-4-isoxazolyl]carbamate;
1-(2-Chlorophenyl)ethyl N-[5-[4-(methoxymethyl)phenyl]-3-methyl-4-isoxazolyl]carbamate;
1-(2-Chlorophenyl)ethyl N-[3-methyl-5-[4-(morpholinomethyl)phenyl]-4-isoxazolyl]carbamate;
1-(2-Chlorophenyl)ethyl N-(5-[4-[(2,6-dimethylmorpholino)methyl]phenyl]-3-methyl-4-isoxazolyl)carbamate;
1-(2-Chlorophenyl)ethyl N-(3-methyl-5-[4-[((2-(2-pyridyl)ethyl]amino)methyl]phenyl]-4-isoxazolyl)carbamate;
1-(2-Chlorophenyl)ethyl N-[3-methyl-5-(4-[[(tetrahydro-2-furanylmethyl)amino]-methyl]phenyl)-4-isoxazolyl]-carbamate;
1-(2-Chlorophenyl)ethyl N-[3-methyl-5-(4-[[(2-pyridylmethyl)amino]methyl]phenyl)-4-isoxazolyl]carbamate;
1-(2-Chlorophenyl)ethyl N-[5-(4-[[(2-furylmethyl)amino]methyl]phenyl)-3-methyl-4-isoxazolyl]carbamate;
2-cyclohexyl N-(5-methyl-3-phenyl-4-isoxazolyl)carbamate;
2-Methylphenethyl N-(5-methyl-3-phenyl-4-isoxazolyl)carbamate;
Phenethyl N-(5-methyl-3-phenyl-4-isoxazolyl)carbamate;
2,3-Dihydro-1H-1-indenyl N-(5-methyl-3-phenyl-4-isoxazolyl)carbamate;
1,2,3,4-Tetrahydro-2-naphthalenyl N-(5-methyl-3-phenyl-4-isoxazolyl)carbamate;
Pentyl N-(5-methyl-3-phenyl-4-isoxazolyl)carbamate;
Isopentyl N-(5-methyl-3-phenyl-4-isoxazolyl)carbamate;
1-Methylpentyl N-(5-methyl-3-phenyl-4-isoxazolyl)carbamate;
4-Pentenyl N-(5-methyl-3-phenyl-4-isoxazolyl)carbamate;
1-(2-Chlorophenyl)ethyl N-{3-methyl-5-[4-({[2-(2-pryidyl)ethyl]amino}methyl)phenyl]-4-isoxazolyl}carbamate;
1-(2-Chlorophenyl)ethyl N-[3-methyl-5-(4-{[(tetrahydro-2-furanylmethyl)amino]-methyl}phenyl)-4-isoxazolyl]carbamate;
1-(2-Chlorophenyl)ethyl N-[3-methyl-5-(4-{[(2-pyridylmethyl)amino]methyl}-phenyl)-4-isoxazolyl]carbamate;
1-(2-Chlorophenyl)ethyl N-[5-(4-{[(2-furylmethyl)amino]methyl}phenyl)-3-methyl-4-isoxazolyl]carbamate;
1-(2-Chlorophenyl)ethyl N-[5-(4-{[(2-furylmethyl)sulfanyl]methyl}phenyl)-3-methyl-4-isoxazolyl]carbamate;
1-(2-Chlorophenyl)ethyl N-(5-{4-[(ethylsulfanyl)methyl]phenyl}-3-methyl-4-isoxazolyl)carbamate;
1-(2-Chlorophenyl)ethyl N-(3-methyl-5-{4-[(pentylamino)methyl]phenyl}-4-isoxazolyl)carbamate;
1-(2-Chlorophenyl)ethyl N-{3-methyl-5-[4-({[2-(3-pyridyl)ethyl]amino}methyl)-phenyl]-4-isoxazolyl}carbamate;
1-(2-Chlorophenyl)ethyl N-{3-methyl-5-[4-({[2-(4-pyridyl)ethyl]amino}methyl)phenyl]-4-isoxazolyl}carbamate;
1-(2-Chlorophenyl)ethyl N-[5-(4-{[(2-fluoroethyl)amino]methyl}phenyl)-3-methyl-4-isoxazolyl]carbamate;
Ethyl 3-({4-[4-({[1-(2-chlorophenyl)ethoxy]carbonyl}amino)-3-methyl-5-isoxazolyl]-benzyl}amino)propanoate;
1-(2-Chlorophenyl)ethyl N-{3-methyl-5-[4-({[(5-methyl-2-pyrazyl)methyl]amino}-methyl)phenyl]-4-isoxazolyl}carbamate;
Methyl 3-({4-[4-({[1-(2-chlorophenyl)ethoxy]carbonyl}amino)-3-methyl-5-isoxazolyl]-benzyl}sulfanyl)propanoate;
1-(2-Chlorophenyl)ethyl N-(5-{4-[(ethylamino)methyl]phenyl}-3-methyl-4-isoxazolyl)-carbamate;
1-(2-Chlorophenyl)ethyl N-(3-methyl-5-{4-[(propylsulfanyl)methyl]phenyl}-4-isoxazolyl)carbamate;

Methyl 2-({4-[4-({[1-(2-chlorophenyl)ethoxy]carbonyl}-amino)-3-methyl-5-isoxazolyl]-benzyl}-sulfanyl)acetate;

Ethyl 2-({4-[4-({[1-(2-chlorophenyl)ethoxy]carbonyl}amino)-3-methyl-5-isoxazolyl]benzyl}-sulfanyl)acetate;

1-(2-Chlorophenyl)ethyl N-[5-(4-{[(2-hydroxyethyl)sulfanyl]methyl}phenyl)-3-methyl-4-isoxazolyl]carbamate;

2-({4-[4-({[1-(2-Chlorophenyl)ethoxy]carbonyl}amino)-3-methyl-5-isoxazolyl]benzyl}-sulfanyl)acetic acid;

1-(2-Chlorophenyl)ethyl N-{5-[4-({[(2R)-2-amino-3-ethyl-3-butenyl]sulfanyl}methyl)-phenyl]-3-methyl-4-isoxazolyl}carbamate;

1-(2-Chlorophenyl)ethyl N-(5-{4-[(allylsulfanyl)methyl]phenyl}-3-methyl-4-isoxazolyl)-carbamate;

1-(2-Chlorophenyl)ethyl N-(3-methyl-5-{4-[(phenethylsulfanyl)methyl]phenyl}-4-isoxazolyl)carbamate;

1-(2-Chlorophenyl)ethyl N-(5-{4-[(butylsulfanyl)methyl]phenyl}-3-methyl-4-isoxazolyl)-carbamate;

3-({4-[4-({[1-(2-Chlorophenyl)ethoxy]carbonyl}amino)-3-methyl-5-isoxazolyl]benzyl}-sulfanyl)propanoic acid;

N-[2-({4-[4-({[1-(2-Chlorophenyl)ethoxy]carbonyl}amino)-3-methyl-5-isoxazolyl]benzyl}-sulfanyl)propanoyl]carbamic acid;

1-(2-Chlorophenyl)ethyl N-{5-[3-(methoxymethyl)phenyl]-3-methyl-4-isoxazolyl}carbamate;

1-(2-Chlorophenyl)ethyl N-{5-[3-(ethoxymethyl)phenyl]-3-methyl-4-isoxazolyl}carbamate;

Methyl 2-({3-[4-({[1-(2-chlorophenyl)ethoxy]carbonyl}amino)-3-methyl-5-isoxazolyl]-benzyl}sulfanyl)acetate;

1-(2-Chlorophenyl)ethyl N-[5-(3-{[(2-hydroxyethyl)sulfanyl]methyl}phenyl)-3-methyl-4-isoxazolyl]carbamate;

1-(2-Chlorophenyl)ethyl N-(5-{3-[(ethylsulfanyl)methyl]phenyl}-3-methyl-4-isoxazolyl)carbamate;

Methyl 2-({4-[4-({[1-(2-chlorophenyl)ethoxy]carbonyl}amino)-3-methyl-5-isoxazolyl]-benzyl}-sulfonyl)acetate;

Methyl 2-({4-[4-({[1-(2-chlorophenyl)ethoxy]carbonyl}amino)-3-methyl-5-isoxazolyl]-benzyl}sulfinyl)acetate;

1(2-Chlorophenyl)ethyl N-[5-(4-{[(2,3-dihydroxypropyl)sufanyl]methyl}phenyl)-3-methyl-4-isoxazolyl]carbamate;

1-(2-Chlorophenyl)ethyl N-(3-methyl-5-{4-[(1H-1,2,4-triazol-3-ylsulfanyl)methyl]-phenyl}-4-isoxazolyl)carbamate;

1-(2-Chlorophenyl)ethyl N-[3-methyl-5-(4-{[(1-methyl-1H-1,2,3,4-tetrazol-5-yl)-sulfanyl]methyl}phenyl)-4-isoxazolyl]carbamate;

1-(2-Chlorophenyl)ethyl N-{3-methyl-5-[4-({[2-(methylamino)-2-oxoethyl]sulfanyl}-methyl)phenyl]-4-isoxazolyl}carbamate;

1-(2-Chlorophenyl)ethyl N-(5-{4-[({2-[(2-furylmethyl)amino]-2-oxoethyl}sulfanyl) -methyl]phenyl}-3-methyl-4-isoxazolyl)carbamate;

Ethyl 2-({3-[4-({[1-(2-chlorophenyl)ethoxy]carbonyl}amino)-3-methyl-5-isoxazolyl]benzyl}-sulfanyl)acetate;

1-(2-Chlorophenyl)ethyl N-(5-{3-[(allylsulfanyl)methyl]phenyl}-3-methyl-4-isoxazolyl)-carbamate;

1-(2-Chlorophenyl)ethyl N-(3-methyl-5-{3-[(phenethylsulfanyl)methyl]phenyl}-4-isoxazolyl)-carbamate;

1-(2-Chlorophenyl)ethyl N-(3-methyl-5-{3-[(1H-1,2,4-triazol-3-ylsulfanyl)methyl]phenyl}-4-isoxazolyl)carbamate;

4-[4-({[1-(2-Chlorophenyl)ethoxy]carbonyl}amino)-3-methyl-5-isoxazolyl]benzyl ethanethioate;

1-(2-Chlorophenyl)ethyl N-{5-[4-({[2-(acetylamino)ethyl]sulfanyl}methyl)phenyl]-3-methyl-4-isoxazolyl}carbamate;

Methyl 3-({4-[4-({[1-(2-chlorophenyl)ethoxy]carbonyl}amino)-3-ethyl-5-isoxazolyl]-benzyl}sulfanyl)propanoate;

3-({4-[4-({[1-(2-Chlorophenyl)ethoxy]carbonyl}amino)-3-ethyl-5-isoxazolyl]benzyl}-sulfanyl)propanoic acid;

2-({4-[4-({[1-(2-Chlorophenyl)ethoxy]carbonyl}amino)-3-methyl-5-isoxazolyl]benzyl}-sulfanyl)propanoic acid;

1-(2-Chlorophenyl)ethyl N-(3-methyl-5-{4-[({2-[(1H-2-pyrrolylcarbonyl)amino]ethyl}-sulfanyl)methyl]phenyl}-4-isoxazolyl)carbamate;

1-(2-Chlorophenyl)ethyl N-[5-(4-{[(2-chloroethyl)sulfanyl]methyl}phenyl)-3-methyl-4-isoxazolyl]carbamate;

2-({4-[4-({[1-(2-Chlorophenyl)ethoxy]carbonyl}amino)-3-methyl-5-isoxazolyl]benzyl}-sulfanyl)-1-ethanesulfonic acid;

3-({4-[4-({[1-(2-Chlorophenyl)ethoxy]carbonyl}amino)-3-methyl-5-isoxazolyl]benzyl}-sulfanyl)-1-propanesulfonic acid;

Methyl 2-({4-[4-({[1-(2-chlorophenyl)ethoxy]carbonyl}amino)-3-ethyl-5-isoxazolyl]benzyl}-sulfanyl)acetate;

2-({4-[4-({[1-(2-Chlorophenyl)ethoxy]carbonyl}amino)-3-ethyl-5-isoxazolyl]benzyl}-sulfanyl)acetic acid;

1-(2-Fluorophenyl)ethyl N-{5-[4-(chloromethyl)phenyl]-3-methyl-4-isoxazolyl}carbamate;

Methyl 3-({4-[4-({[1-(2-fluorophenyl)ethoxy]carbonyl}amino)-3-methyl-5-isoxazolyl]-benzyl}-sulfanyl)propanoate;

3-({4-[4-({[1-(2-Fluorophenyl)ethoxy]carbonyl}amino)-3-methyl-5-isoxazolyl]benzyl}-sulfanyl)propanoic acid;

2-({3-[4-({[1-(2-Chlorophenyl)ethoxy]carbonyl}amino)-3-methyl-5-isoxazolyl]benzyl}-sulfanyl)-1-ethanesulfonic acid;

3-({3-[4-({[1-(2-Chlorophenyl)ethoxy]carbonyl}amino)-3-methyl-5-isoxazolyl]benzyl}-sulfanyl)propanoic acid;

1-(2-Fluorophenyl)ethyl N-{5-[4-(chloromethyl)phenyl]-3-ethyl-4-isoxazolyl}carbamate;

2,2,2-Trifluoro-1-phenylethyl N-{5-[4-(chloromethyl)phenyl]-3-methyl-4-isoxazolyl}-carbamate;

Methyl 3-{[4-(3-methyl-4-[(2,2,2-trifluoro-1-phenylethoxy)carbonyl]amino}-5-isoxazolyl)-benzyl]-sulfanyl}propanoate;

3-{[4-(3-Methyl-4-{[(2,2,2-trifluoro-1-phenylethoxy)carbonyl]amino}-5-isoxazolyl)benzyl]-sulfanyl}propanoic acid;

2,2,2-Trifluoro-1-phenylethyl N-{5-[4-(chloromethyl)phenyl]-3-ethyl-4-isoxazolyl}carbamate;

Methyl 3-({4-[3-ethyl-4-({[1-(2-fluorophenyl)ethoxy]carbonyl}amino)-5-isoxazolyl]-benzyl}sulfanyl)propanoate;

Methyl 3-{[4-(3-ethyl-4-{[(2,2,2-trifluoro-1-phenylethoxy)carbonyl]amino}-5-isoxazolyl)-benzyl]sulfanyl}propanoate;

3-({4-[3-Ethyl-4-({[1-(2-fluorophenyl)ethoxy]carbonyl}amino)-5-isoxazolyl]benzyl}-sulfanyl)propanoic acid;

Ethyl 2-({4-[4-({[1-(2-chlorophenyl)ethoxy]carbonyl}amino)-3-methyl-5-isoxazolyl]-benzyl}oxy)acetate; and Ethyl 2-{[4-(3-methyl-4-{[(2,2,2-trifluoro-1-phenylethoxy)carbonyl]amino}-5-isoxazolyl)-benzyl]oxy}acetate;

or salt thereof.

* * * * *

UNITED STATES PATENT AND TRADEMARK OFFICE
CERTIFICATE OF CORRECTION

PATENT NO.        : 6,964,975 B2                                    Page 1 of 2
APPLICATION NO. : 10/204173
DATED             : November 15, 2005
INVENTOR(S)       : Akihiro Ueno et al.

It is certified that error appears in the above-identified patent and that said Letters Patent is hereby corrected as shown below:

IN THE CLAIMS

Column 80, Claim 5, lines 6 – 13, please change:

"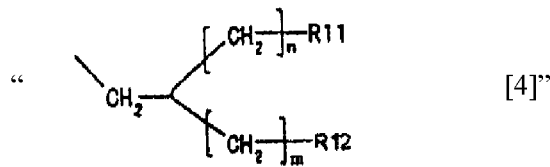 [4]"

to

-- 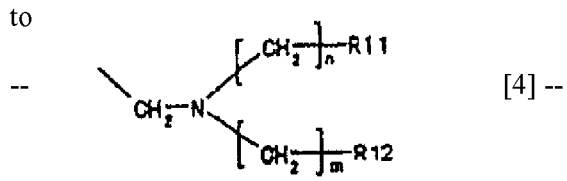 [4] --

Column 82, Claim 7, lines 23 – 30, please change:

"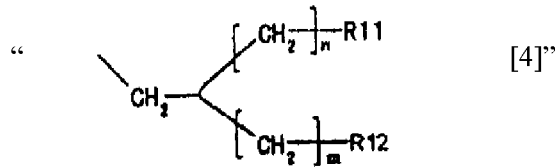 [4]"

to

-- 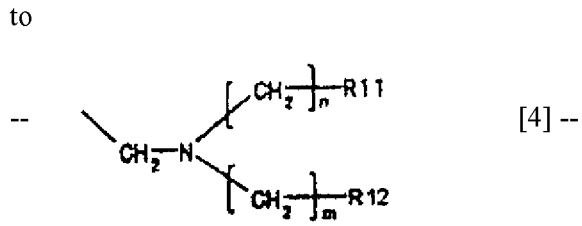 [4] --

UNITED STATES PATENT AND TRADEMARK OFFICE
CERTIFICATE OF CORRECTION

PATENT NO. : 6,964,975 B2  Page 2 of 2
APPLICATION NO. : 10/204173
DATED : November 15, 2005
INVENTOR(S) : Akihiro Ueno et al.

It is certified that error appears in the above-identified patent and that said Letters Patent is hereby corrected as shown below:

Column 84, Claim 17, lines 51 – 58, please change:

" 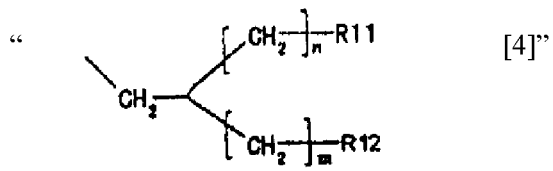 [4]"

to

-- 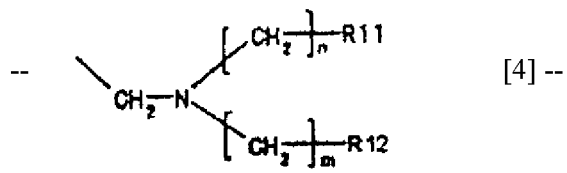 [4] --

Signed and Sealed this

Third Day of June, 2008

JON W. DUDAS
*Director of the United States Patent and Trademark Office*